US011944273B2

United States Patent
Talbert et al.

(10) Patent No.: US 11,944,273 B2
(45) Date of Patent: Apr. 2, 2024

(54) FLUORESCENCE VIDEOSTROBOSCOPY OF VOCAL CORDS

(71) Applicant: Cilag GmbH International, Zug (CH)

(72) Inventors: Joshua D. Talbert, Salt Lake City, UT (US); Donald M. Wichern, Ogden, UT (US)

(73) Assignee: Cilag GmbH International, Zug (CH)

( * ) Notice: Subject to any disclaimer, the term of this patent is extended or adjusted under 35 U.S.C. 154(b) by 259 days.

(21) Appl. No.: 16/812,009

(22) Filed: Mar. 6, 2020

(65) Prior Publication Data

US 2020/0397254 A1    Dec. 24, 2020

Related U.S. Application Data

(60) Provisional application No. 62/864,251, filed on Jun. 20, 2019.

(51) Int. Cl.
*A61B 1/04* (2006.01)
*A61B 1/00* (2006.01)
(Continued)

(52) U.S. Cl.
CPC .......... *A61B 1/043* (2013.01); *A61B 1/00004* (2013.01); *A61B 1/00006* (2013.01);
(Continued)

(58) Field of Classification Search
CPC ........ A61B 1/2673; A61B 2017/00172; A61B 1/043; A61B 1/00004; A61B 1/05;
(Continued)

(56) References Cited

U.S. PATENT DOCUMENTS

| 4,535,758 A | * | 8/1985 | Longacre, Jr. | ......... H04N 23/74 348/69 |
| 4,635,123 A | * | 1/1987 | Masunaga | .............. H04N 23/74 348/E5.038 |

(Continued)

FOREIGN PATENT DOCUMENTS

| CN | 111526775 A | 8/2020 |
| CN | 111565620 A | 8/2020 |

(Continued)

OTHER PUBLICATIONS

Frietz, Eric et al. "Endoscopic laser range scanner for minimally invasive, image guided kidney surgery." Proceedings of the SPIE vol. 8671, 2013, pp. 1 [online], [retrieved on Aug. 25, 2020]. Retrieved from <https://ui.adsabs.harvard.edu/abs/2013SPIE.8671E..05F/abstract>.

*Primary Examiner* — Anh Tuan T Nguyen
*Assistant Examiner* — Jae Woo
(74) *Attorney, Agent, or Firm* — TechLaw Ventures, PLLC; Terrence J. Edwards

(57) ABSTRACT

Fluorescence videostroboscopy imaging is described. A system includes an emitter for emitting pulses of electromagnetic radiation and an image sensor comprising a pixel array for sensing reflected electromagnetic radiation. The system includes a controller configured to cause the emitter to emit the pulses of electromagnetic radiation at a strobing frequency determined based on a vibration frequency of vocal cords of a user. The system is such that at least a portion of the pulses of electromagnetic radiation emitted by the emitter comprises electromagnetic radiation having a wavelength from about 770 nm to about 790 nm and from about 795 nm to about 815 nm.

25 Claims, 33 Drawing Sheets

(51) Int. Cl.
  *A61B 1/045* (2006.01)
  *A61B 1/05* (2006.01)
  *A61B 1/06* (2006.01)
  *A61B 1/267* (2006.01)
  *A61B 5/00* (2006.01)
  *G01N 21/64* (2006.01)
  *G01S 7/483* (2006.01)
  *G01S 17/89* (2020.01)
  *G06T 7/00* (2017.01)
  *H04N 23/72* (2023.01)
  *A61B 17/00* (2006.01)
  *H04N 23/50* (2023.01)

(52) U.S. Cl.
  CPC ...... *A61B 1/00039* (2013.01); *A61B 1/00042* (2022.02); *A61B 1/0005* (2013.01); *A61B 1/00087* (2013.01); *A61B 1/045* (2013.01); *A61B 1/05* (2013.01); *A61B 1/063* (2013.01); *A61B 1/0638* (2013.01); *A61B 1/0661* (2013.01); *A61B 1/267* (2013.01); *A61B 1/2673* (2013.01); *A61B 5/0033* (2013.01); *A61B 5/0071* (2013.01); *G01N 21/6456* (2013.01); *G01S 7/483* (2013.01); *G01S 17/89* (2013.01); *G06T 7/0012* (2013.01); *H04N 23/72* (2023.01); *A61B 1/000095* (2022.02); *A61B 2017/00154* (2013.01); *A61B 2017/00172* (2013.01); *A61B 2017/00194* (2013.01); *G06T 2207/10064* (2013.01); *G06T 2207/10068* (2013.01); *G06T 2207/30024* (2013.01); *H04N 23/555* (2023.01)

(58) Field of Classification Search
  CPC .................. A61B 1/063; A61B 1/0638; A61B 1/000095; A61B 2017/00154; G01S 7/483
  See application file for complete search history.

(56) References Cited

U.S. PATENT DOCUMENTS

| | | |
|---|---|---|
| 5,090,400 A | 2/1992 | Saito |
| 5,149,972 A | 9/1992 | Fay et al. |
| 5,318,024 A | 6/1994 | Kittrell et al. |
| 5,363,387 A | 11/1994 | Sinofsky |
| 5,749,830 A | 5/1998 | Kaneko et al. |
| 5,784,162 A | 7/1998 | Cabib et al. |
| 6,110,106 A | 8/2000 | MacKinnon et al. |
| 6,122,042 A | 9/2000 | Wunderman et al. |
| 6,236,879 B1 | 5/2001 | Konings |
| 6,276,798 B1 | 8/2001 | Gil et al. |
| 6,293,911 B1 * | 9/2001 | Imaizumi .......... A61B 1/000094 600/178 |
| 6,364,829 B1 | 4/2002 | Fulghum |
| 6,448,545 B1 | 9/2002 | Chen |
| 6,717,174 B2 | 4/2004 | Karellas |
| 6,975,898 B2 | 12/2005 | Seibel |
| 7,235,045 B2 | 6/2007 | Wang et al. |
| 7,375,311 B2 | 5/2008 | Wiklof et al. |
| 7,649,618 B2 | 1/2010 | Tuschel et al. |
| 7,865,230 B1 | 1/2011 | Sevivk-Muraca et al. |
| 8,185,176 B2 | 5/2012 | Mangat et al. |
| 8,706,184 B2 | 4/2014 | Mohr et al. |
| 8,718,351 B2 | 5/2014 | So et al. |
| 9,080,977 B2 | 7/2015 | Contag et al. |
| 9,435,993 B2 | 9/2016 | Kanarowski |
| 9,509,917 B2 | 11/2016 | Blanquart et al. |
| 9,777,913 B2 | 10/2017 | Talbert et al. |
| 10,041,833 B1 | 8/2018 | Chirayath |
| 10,080,484 B2 | 9/2018 | Yang et al. |
| 10,231,626 B2 | 3/2019 | Steinbach et al. |
| 10,247,672 B2 | 4/2019 | Betzig et al. |
| 10,341,593 B2 | 7/2019 | Blanquart et al. |
| 10,382,742 B2 | 8/2019 | Retterath |
| 10,395,382 B2 | 8/2019 | Bustan et al. |
| 10,447,936 B2 | 10/2019 | Motoki |
| 10,481,095 B2 | 11/2019 | Dimitriadis et al. |
| 10,517,483 B2 | 12/2019 | Wood et al. |
| 10,598,914 B2 | 3/2020 | Siegel et al. |
| 10,694,117 B2 | 6/2020 | Frangioni |
| 10,694,152 B2 | 6/2020 | Westwick et al. |
| 10,803,578 B2 | 10/2020 | Butte et al. |
| 10,902,572 B1 | 1/2021 | Kennedy |
| 10,980,420 B2 | 4/2021 | Fengler et al. |
| 11,178,340 B2 * | 11/2021 | Sato ................... A61B 1/0684 |
| 11,666,209 B2 * | 6/2023 | Bos ..................... A61B 1/2673 600/188 |
| 2001/0000317 A1 | 4/2001 | Yoneya et al. |
| 2002/0016533 A1 | 2/2002 | Marchitto et al. |
| 2002/0123666 A1 | 9/2002 | Matsumoto |
| 2002/0161282 A1 | 10/2002 | Fulghum |
| 2003/0100824 A1 | 5/2003 | Warren et al. |
| 2004/0186351 A1 | 9/2004 | Imaizumi et al. |
| 2004/0225222 A1 | 11/2004 | Zeng et al. |
| 2004/0234152 A1 | 11/2004 | Leige et al. |
| 2005/0020926 A1 | 1/2005 | Wiklof et al. |
| 2005/0107808 A1 | 5/2005 | Evans et al. |
| 2005/0219552 A1 | 10/2005 | Ackerman et al. |
| 2006/0069314 A1 | 3/2006 | Farr |
| 2006/0106317 A1 | 5/2006 | McConnell et al. |
| 2006/0239723 A1 | 10/2006 | Okuda et al. |
| 2006/0276966 A1 | 12/2006 | Cotton et al. |
| 2007/0016077 A1 | 1/2007 | Nakaoka et al. |
| 2007/0046778 A1 | 3/2007 | Ishihara et al. |
| 2007/0057211 A1 | 3/2007 | Bahlman et al. |
| 2007/0060792 A1 | 3/2007 | Draxinger et al. |
| 2007/0086495 A1 | 4/2007 | Sprague et al. |
| 2007/0160279 A1 | 7/2007 | Demos |
| 2007/0242330 A1 | 10/2007 | Rosman et al. |
| 2007/0276234 A1 | 11/2007 | Shahidi |
| 2008/0058629 A1 | 3/2008 | Seibel et al. |
| 2008/0081950 A1 | 4/2008 | Koenig et al. |
| 2008/0177139 A1 | 7/2008 | Courtney et al. |
| 2008/0180547 A1 * | 7/2008 | Hirose .................. H04N 23/84 348/229.1 |
| 2009/0067458 A1 | 3/2009 | Ji et al. |
| 2009/0240139 A1 | 9/2009 | Yi |
| 2009/0242797 A1 | 10/2009 | Yazdanfar et al. |
| 2009/0244521 A1 | 10/2009 | Yazdanfar et al. |
| 2009/0306478 A1 | 12/2009 | Mizuyoshi |
| 2009/0316116 A1 | 12/2009 | Melville et al. |
| 2010/0004513 A1 | 1/2010 | MacKinnon et al. |
| 2010/0049180 A1 | 2/2010 | Wells et al. |
| 2010/0056928 A1 | 3/2010 | Zuzak et al. |
| 2010/0063384 A1 | 3/2010 | Kornblau et al. |
| 2010/0073494 A1 * | 3/2010 | Hirose .................. H04N 23/71 348/208.4 |
| 2010/0128109 A1 | 5/2010 | Banks |
| 2010/0181497 A1 | 7/2010 | Hess et al. |
| 2010/0261958 A1 | 10/2010 | Webb et al. |
| 2010/0277087 A1 | 11/2010 | Ikeda |
| 2011/0087212 A1 | 4/2011 | Aldridge et al. |
| 2011/0176029 A1 | 7/2011 | Boydston et al. |
| 2011/0196355 A1 | 8/2011 | Mitchell et al. |
| 2011/0224541 A1 | 9/2011 | Yun et al. |
| 2012/0123205 A1 | 5/2012 | Nie et al. |
| 2012/0130258 A1 | 5/2012 | Taylor et al. |
| 2012/0253200 A1 | 10/2012 | Stolka et al. |
| 2012/0280144 A1 | 11/2012 | Guilfoyle et al. |
| 2012/0281071 A1 | 11/2012 | Bergman et al. |
| 2012/0293699 A1 * | 11/2012 | Blanquart ............ H04N 25/533 348/308 |
| 2012/0294498 A1 | 11/2012 | Popovic |
| 2012/0310098 A1 | 12/2012 | Popovic |
| 2013/0012794 A1 | 1/2013 | Zeng et al. |
| 2013/0176395 A1 | 7/2013 | Kazakevich |
| 2013/0286179 A1 | 10/2013 | Markle et al. |
| 2013/0286181 A1 | 10/2013 | Betzig et al. |
| 2014/0078277 A1 * | 3/2014 | Dai ..................... H04N 25/531 348/308 |
| 2014/0111623 A1 | 4/2014 | Zhao et al. |
| 2014/0114150 A1 | 4/2014 | Pogue et al. |

(56) References Cited

U.S. PATENT DOCUMENTS

| | | |
|---|---|---|
| 2014/0160259 A1 | 6/2014 | Blanquart et al. |
| 2014/0160318 A1* | 6/2014 | Blanquart .............. A61B 1/063 348/234 |
| 2014/0163319 A1 | 6/2014 | Blanquart et al. |
| 2014/0163389 A1 | 6/2014 | Kudenov et al. |
| 2014/0248576 A1 | 9/2014 | Tchouprakov et al. |
| 2014/0276093 A1 | 9/2014 | Zeien |
| 2014/0296644 A1 | 10/2014 | Zilberstein et al. |
| 2014/0300750 A1 | 10/2014 | Nagamune |
| 2014/0316196 A1 | 10/2014 | Wichern et al. |
| 2014/0336461 A1 | 11/2014 | Reiter et al. |
| 2014/0336501 A1 | 11/2014 | Matsumoto |
| 2015/0015879 A1 | 1/2015 | Papadopoulos et al. |
| 2015/0073209 A1 | 3/2015 | Ikeda |
| 2015/0223733 A1 | 8/2015 | Al-Alusi |
| 2015/0297324 A1 | 10/2015 | Tchouprakov et al. |
| 2015/0309284 A1 | 10/2015 | Kagawa et al. |
| 2016/0006914 A1 | 1/2016 | Neumann |
| 2016/0042513 A1 | 2/2016 | Yudovsky |
| 2016/0062103 A1 | 3/2016 | Yang et al. |
| 2016/0150963 A1 | 6/2016 | Roukes et al. |
| 2016/0183775 A1 | 6/2016 | Blanquart et al. |
| 2016/0195705 A1 | 7/2016 | Betzig et al. |
| 2016/0195706 A1 | 7/2016 | Fujii |
| 2016/0263402 A1 | 9/2016 | Zhang et al. |
| 2016/0287141 A1 | 10/2016 | Sidlesky |
| 2016/0330355 A1 | 11/2016 | Tchouprakov et al. |
| 2016/0364858 A1 | 12/2016 | Butte et al. |
| 2017/0202461 A1 | 7/2017 | Darty et al. |
| 2017/0209050 A1 | 7/2017 | Fengler et al. |
| 2017/0224272 A1 | 8/2017 | Liu et al. |
| 2017/0280029 A1 | 9/2017 | Steiner |
| 2017/0280970 A1 | 10/2017 | Sartor et al. |
| 2017/0307440 A1 | 10/2017 | Urban et al. |
| 2017/0347043 A1 | 11/2017 | Rephaeli et al. |
| 2017/0360275 A1 | 12/2017 | Yoshizaki |
| 2018/0000401 A1 | 1/2018 | Kang et al. |
| 2018/0088048 A1 | 3/2018 | Dong et al. |
| 2018/0116494 A1 | 5/2018 | Treado et al. |
| 2018/0146844 A1* | 5/2018 | Okazaki ........... A61B 1/000095 |
| 2018/0168455 A1 | 6/2018 | Tesar |
| 2018/0310828 A1 | 11/2018 | DiMaio et al. |
| 2018/0318033 A1 | 11/2018 | Tesar |
| 2018/0325604 A1 | 11/2018 | Atarot et al. |
| 2018/0367786 A1 | 12/2018 | Furst et al. |
| 2019/0046302 A1 | 2/2019 | Li et al. |
| 2019/0051409 A1 | 2/2019 | Petrossian et al. |
| 2019/0082936 A1* | 3/2019 | Yamazaki ................ H04N 7/18 |
| 2019/0125458 A1 | 5/2019 | Shelton, IV et al. |
| 2019/0133450 A1 | 5/2019 | Kannan et al. |
| 2019/0142265 A1* | 5/2019 | Bos .................... A61B 1/00045 600/188 |
| 2019/0191974 A1 | 6/2019 | Talbert et al. |
| 2019/0191975 A1 | 6/2019 | Talbert et al. |
| 2019/0191976 A1 | 6/2019 | Talbert et al. |
| 2019/0191978 A1 | 6/2019 | Talbert et al. |
| 2019/0197712 A1 | 6/2019 | Talbert et al. |
| 2019/0216325 A1 | 7/2019 | Ouyang |
| 2019/0227291 A1 | 7/2019 | Stokes et al. |
| 2019/0250394 A1 | 8/2019 | Ganapati et al. |
| 2019/0298151 A1 | 10/2019 | Frangioni |
| 2019/0350672 A1 | 11/2019 | Smith et al. |
| 2020/0015925 A1 | 1/2020 | Scheib |
| 2020/0026051 A1 | 1/2020 | Dixon et al. |
| 2020/0033584 A1 | 1/2020 | Jeong et al. |
| 2020/0054280 A1 | 2/2020 | Cohen et al. |
| 2020/0073100 A1 | 3/2020 | Gibson et al. |
| 2020/0214538 A1 | 7/2020 | Pesach et al. |
| 2020/0289205 A1 | 9/2020 | Scheib et al. |
| 2020/0289222 A1 | 9/2020 | Denlinger et al. |
| 2020/0305259 A1* | 9/2020 | Kojima .................... A61B 1/07 |
| 2020/0305721 A1 | 10/2020 | Chen et al. |
| 2020/0318810 A1 | 10/2020 | Tesar et al. |
| 2020/0330041 A1 | 10/2020 | Henley et al. |
| 2020/0342205 A1 | 10/2020 | Park et al. |
| 2020/0346041 A1 | 11/2020 | Krishnaswamy et al. |
| 2020/0383576 A1 | 12/2020 | Anwar et al. |
| 2020/0397261 A1* | 12/2020 | Talbert ................ G02B 6/0006 |
| 2020/0397266 A1 | 12/2020 | Hufford |
| 2020/0397275 A1 | 12/2020 | Talbert et al. |
| 2020/0397276 A1 | 12/2020 | Talbert et al. |
| 2020/0397277 A1 | 12/2020 | Talbert et al. |
| 2020/0404145 A1 | 12/2020 | Talbert et al. |
| 2020/0404146 A1 | 12/2020 | Talbert et al. |
| 2021/0015350 A1 | 1/2021 | Butte et al. |
| 2021/0068639 A1 | 3/2021 | Treado et al. |
| 2021/0082094 A1 | 3/2021 | McCall et al. |
| 2021/0110521 A1 | 4/2021 | Kennedy |

FOREIGN PATENT DOCUMENTS

| | | |
|---|---|---|
| CN | 111601536 A | 8/2020 |
| WO | 2014018951 A1 | 1/2014 |
| WO | 2015077493 A1 | 5/2015 |
| WO | 2017201093 A1 | 11/2017 |
| WO | 2018049215 A1 | 3/2018 |
| WO | 2019133736 A1 | 7/2019 |
| WO | 2019133737 A1 | 7/2019 |
| WO | 2019133739 A1 | 7/2019 |
| WO | 2019133741 A1 | 7/2019 |
| WO | 2019133750 A1 | 7/2019 |
| WO | 2019133753 A1 | 7/2019 |
| WO | 2020257339 A1 | 12/2020 |
| WO | 2020257340 A1 | 12/2020 |
| WO | 2020257341 A1 | 12/2020 |
| WO | 2020257343 A1 | 12/2020 |
| WO | 2020257345 A1 | 12/2020 |
| WO | 2020257346 A1 | 12/2020 |

* cited by examiner

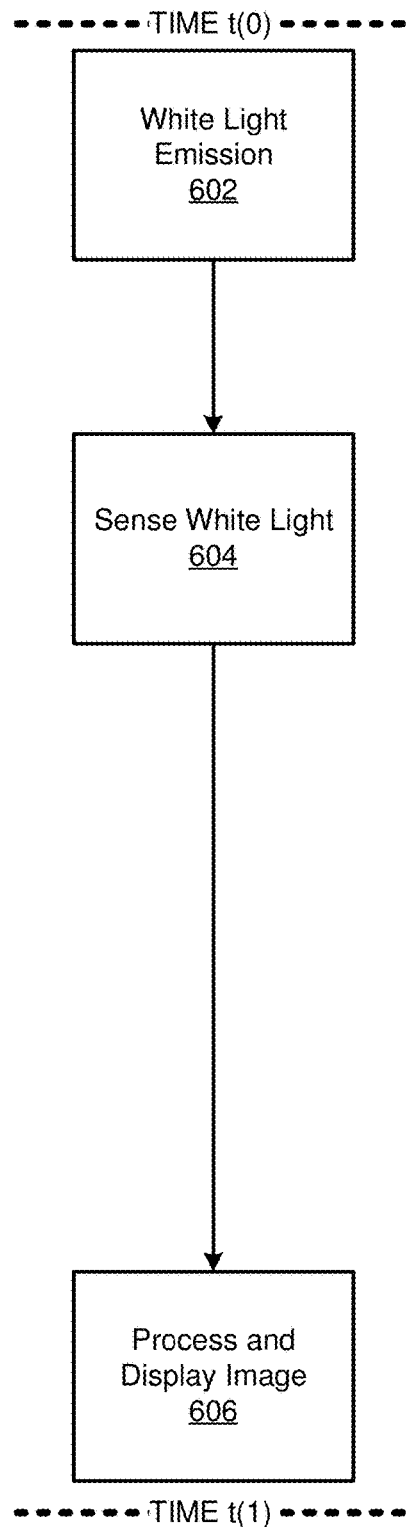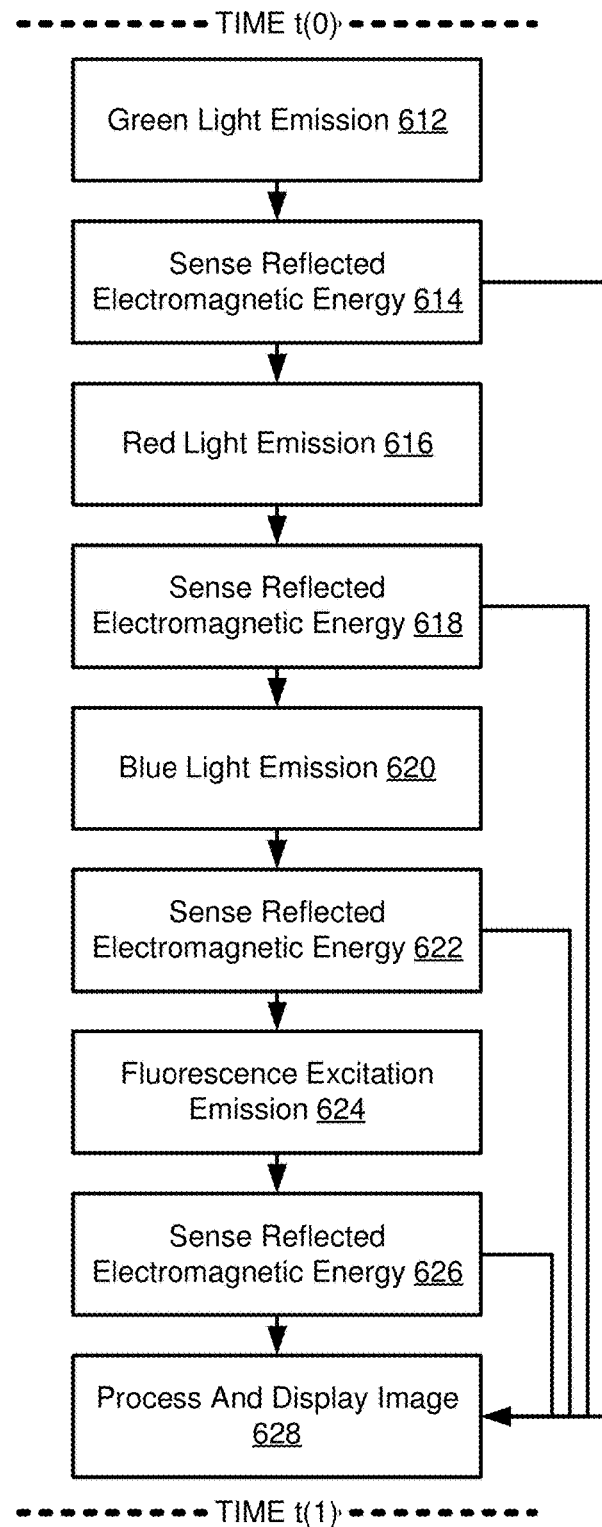
FIG. 6A
(Prior Art)
FIG. 6B

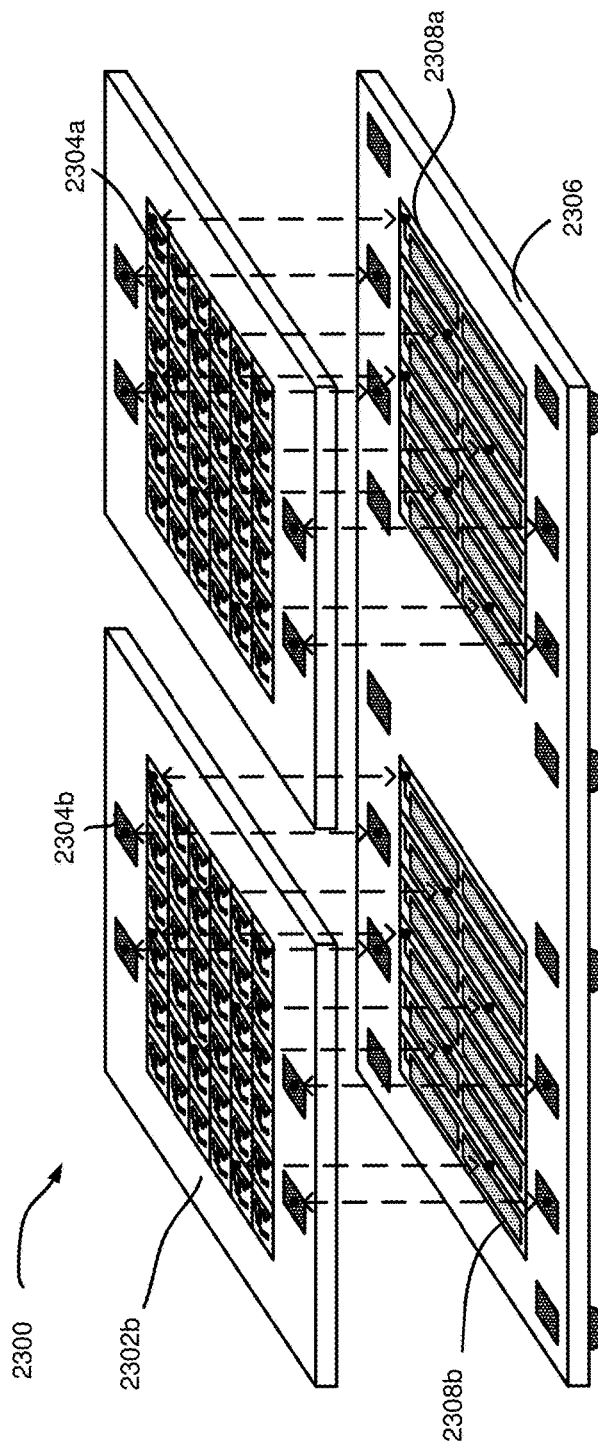
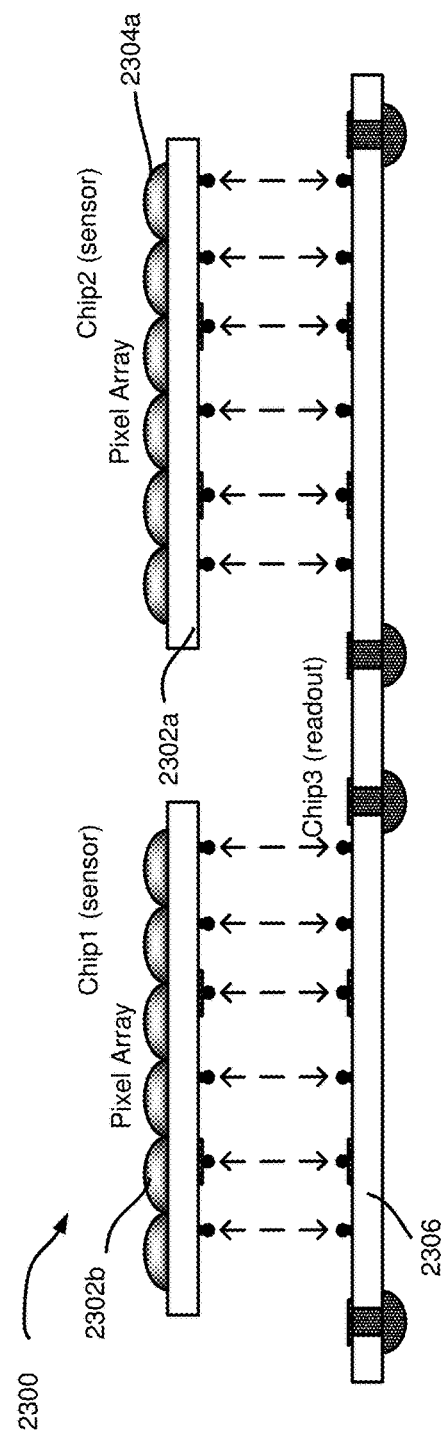
FIG. 23A
FIG. 23B 3D with double pixel array

FLUORESCENCE VIDEOSTROBOSCOPY OF VOCAL CORDS

CROSS-REFERENCE TO RELATED APPLICATIONS

This application claims the benefit of U.S. Provisional Patent Application No. 62/864,251, filed Jun. 20, 2019, titled "VIDEOSTROBOSCOPY OF VOCAL CORDS WITH CMOS SENSORS USING HYPERSPECTRAL AND FLUORESCENCE IMAGING," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

This disclosure is directed to digital imaging and is particularly directed to fluorescence imaging in a light deficient environment.

BACKGROUND

Advances in technology have provided advances in imaging capabilities for medical use. An endoscope may be used to look inside a body and examine the interior of an organ or cavity of the body. Endoscopes are used for investigating a patient's symptoms, confirming a diagnosis, or providing medical treatment. A medical endoscope may be used for viewing a variety of body systems and parts such as the gastrointestinal tract, the respiratory tract, the urinary tract, the abdominal cavity, and so forth. Endoscopes may further be used for surgical procedures such as plastic surgery procedures, procedures performed on joints or bones, procedures performed on the neurological system, procedures performed within the abdominal cavity, and so forth.

In some instances of endoscopic imaging, it may be beneficial or necessary to view a space in color. A digital color image includes at least three layers, or "color channels," that cumulatively form an image with a range of hues. Each of the color channels measures the intensity and chrominance of light for a spectral band. Commonly, a digital color image includes a color channel for red, green, and blue spectral bands of light (this may be referred to as a Red Green Blue or RGB image). Each of the red, green, and blue color channels include brightness information for the red, green, or blue spectral band of light. The brightness information for the separate red, green, and blue layers are combined to create the color image. Because a color image is made up of separate layers, a conventional digital camera image sensor includes a color filter array that permits red, green, and blue visible light wavelengths to hit selected pixel sensors. Each individual pixel sensor element is made sensitive to red, green, or blue wavelengths and will only return image data for that wavelength. The image data from the total array of pixel sensors is combined to generate the RGB image. The at least three distinct types of pixel sensors consume significant physical space such that the complete pixel array cannot fit in the small distal end of an endoscope.

Because a traditional image sensor cannot fit in the distal end of an endoscope, the image sensor is traditionally located in a handpiece unit of an endoscope that is held by an endoscope operator and is not placed within the body cavity. In such an endoscope, light is transmitted along the length of the endoscope from the handpiece unit to the distal end of the endoscope. This configuration has significant limitations. Endoscopes with this configuration are delicate and can be easily misaligned or damaged when bumped or impacted during regular use. This can significantly degrade the quality of the images and necessitate that the endoscope be frequently repaired or replaced.

The traditional endoscope with the image sensor placed in the handpiece unit is further limited to capturing only color images. However, in some implementations, it may be desirable to capture images with fluorescence image data in addition to color image data. Fluorescence is the emission of light by a substance that has absorbed light or other electromagnetic radiation. Certain fluorescent materials "glow" or emit a distinct color that is visible to the human eye when the fluorescent material is subjected to ultraviolet light or other wavelengths of electromagnetic radiation. Certain fluorescent materials will cease to glow nearly immediately when the radiation source stops.

Fluorescence occurs when an orbital electron of a molecule, atom, or nanostructure is excited by light or other electromagnetic radiation, and then relaxes to its ground state by emitting a photon from the excited state. The specific frequencies of electromagnetic radiation that excite the orbital electron, or are emitted by the photon during relaxation, are dependent on the atom, molecule, or nanostructure. Fluorescence imaging has numerous practical applications, including mineralogy, gemology, medicine, spectroscopy for chemical sensors, detecting biological processes or signals, and others. Fluorescence can be used in biochemistry and medicine as a non-destructive means for tracking or analyzing biological molecules. Some fluorescent reagents or dyes can be configured to attach to certain types of tissue and thereby draw attention to that type of tissue.

However, fluorescence imaging requires specialized emissions of electromagnetic radiation and specialized imaging sensors capable of reading the specific relaxation wavelength for a specific fluorescent reagent. Different reagents or dyes are sensitive to different wavelengths of electromagnetic radiation and emit different wavelengths of electromagnetic radiation when fluoresced. A fluorescent imaging system may be highly specialized and tuned for a certain reagent or dye. Such imaging systems are useful for limited applications and are not capable of fluorescing more than one reagent or structure during a single imaging session. It is very costly to use multiple distinct imaging systems that are each configured for fluorescing a different reagent. Additionally, it may be desirable to administer multiple fluorescent reagents in a single imaging session and view the multiple reagents in a single overlaid image.

In light of the foregoing, described herein are systems, methods, and devices for fluorescent imaging in a light deficient environment. Such systems, methods, and devices may provide multiple datasets for identifying critical structures in a body and providing precise and valuable information about the body cavity.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified.

Advantages of the disclosure will become better understood with regard to the following description and accompanying drawings where:

FIG. 6A is a schematic diagram of a process for recording a video with full spectrum light over a period of time from t(0) to t(1);

FIG. 6B is a schematic diagram of a process for recording a video by pulsing portioned spectrum light over a period of time from t(0) to t(1);

FIGS. 23A and 23B illustrate a perspective view and a side view, respectively, of an implementation of an imaging sensor having a plurality of pixel arrays for producing a three-dimensional image, wherein the plurality of pixel arrays and the image sensor are built on a plurality of substrates;

DETAILED DESCRIPTION

Figure 1:
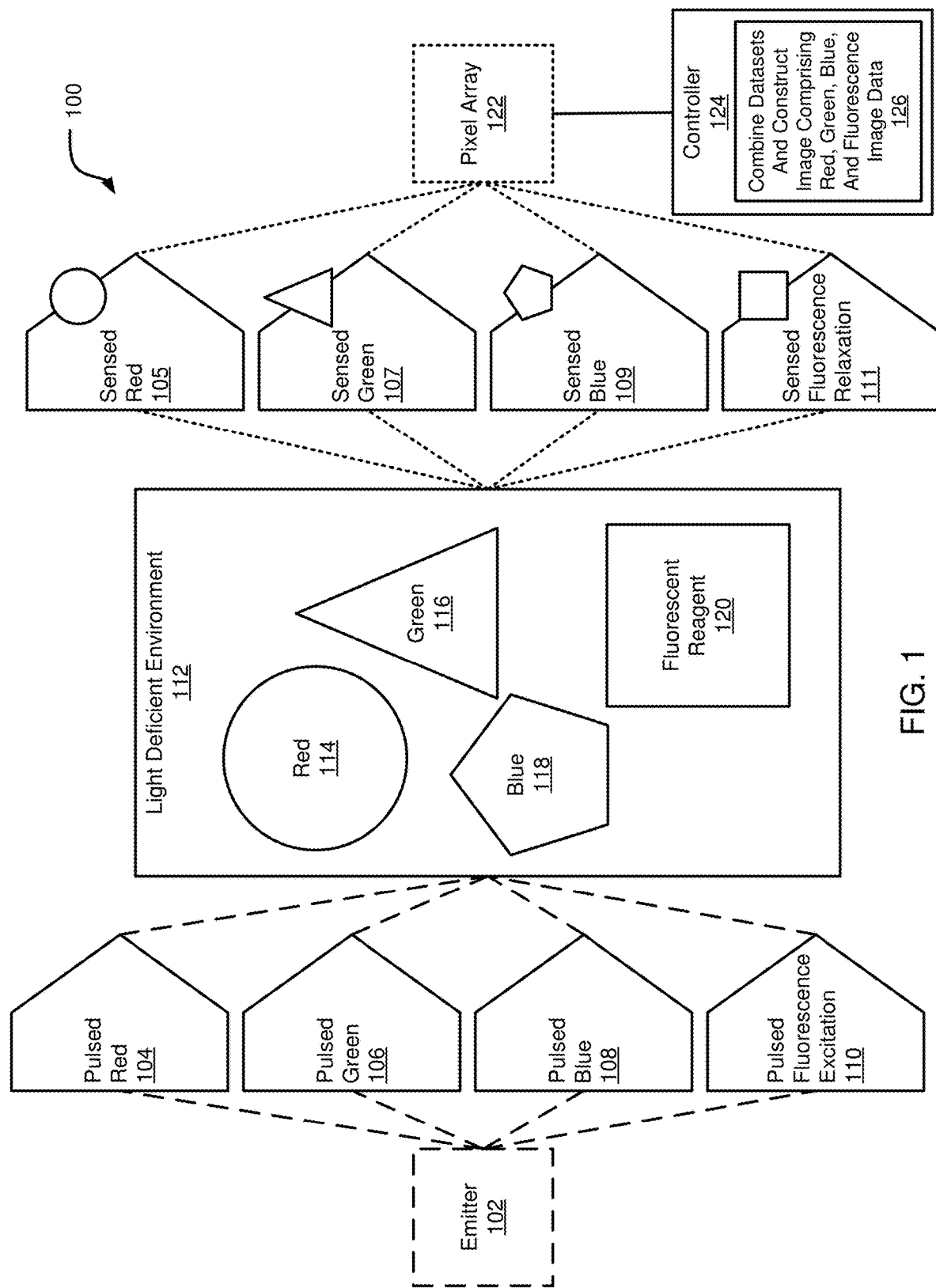
FIG. 1 is a schematic view of a system for digital imaging in a light deficient environment with a paired emitter and pixel array.

Disclosed herein are systems, methods, and devices for digital imaging that may be primarily suited to medical applications such as medical endoscopic imaging. An embodiment of the disclosure is an endoscopic system for fluorescence and color imaging in a light deficient environment. Such methods, systems, and computer-based products disclosed herein provide imaging or diagnostic capabilities for use in medical robotics applications, such as the use of robotics for performing imaging procedures, surgical procedures, and the like.

An embodiment of the disclosure is an endoscopic imaging system for videostroboscopy. Videostroboscopy is an imaging procedure for diagnosing vocal cord conditions and abnormalities. Videostroboscopy is performed with an endoscope, a light source capable of being strobed, and a microphone. During the procedure, an imaging end of the endoscope is brought into view of the patient's vocal cords and then the patient is asked to speak, repeat key phrases, or sing. The microphone is used to pick up the frequency of the patient's voice and the light source is strobed at a similar frequency. This provides a slow-motion view of the vocal cords in action. The endoscope operator may then use the slow-motion video stream of the vocal cords to identify vocal cord conditions and abnormalities.

Traditionally, charge-coupled device (CCD) type endoscopes are required for any application that requires light strobing. The basic approach is to continually strobe the light source at a desired frequency. Because the CCD sensors use global shuttering, the strobing may continue without any degradation in video quality. However, CCD sensors are substantially more expensive than Complementary Metal Oxide Semiconductor (CMOS) sensors and are known to be inferior to CMOS image sensor in key areas. CMOS image sensors have largely displaced conventional CCD images in modern camera applications such as endoscopy, owing to their greater ease of integration and operation, superior image quality, greater versatility, and lower cost. There is, therefore, a desire to implement CMOS image sensors in endoscopes for videostroboscopy. In light of the foregoing, described herein are systems, methods, and devices for videostroboscopy using a CMOS image sensor.

Conventional endoscopes are designed such that the image sensor is placed at a proximal end of the device within a handpiece unit. This configuration requires that incident light travel the length of the endoscope by way of precisely coupled optical elements. The precise optical elements can easily be misaligned during regular use, and this can lead to image distortion or image loss. Embodiments of the disclosure place an image sensor within the highly space-constrained environment in the distal end of the endoscope itself. This provides greater optical simplicity when compared with implementations known in the art. However, an acceptable solution to this approach is by no means trivial and introduces its own set of engineering challenges.

There can be a noticeable loss to image quality when the overall size of an image sensor is minimized such that the image sensor can fit within the distal tip of an endoscope. The area of the pixel array of the image sensor can be reduced by reducing the number of pixels and/or the sensing area of each individual pixel. Each of these modifications impacts the resolution, sensitivity, and dynamic range of the resultant images. Traditional endoscopic imaging systems are geared toward sensing steady broadband illumination and providing color information by virtue of segmented pixel arrays such as the Bayer pattern array. In light of the deficiencies associated with segmented pixel arrays, disclosed herein are alternative systems and methods that use a monochromatic (may be referred to as "color agnostic") pixel array that does not include individual pixel filters. In the embodiments disclosed herein, the color information is provided by pulsing an emitter with different wavelengths of electromagnetic radiation. The pulsed imaging system disclosed herein can generate color images with fluorescence imaging data overlaid thereon.

In an embodiment, the color information is determined by capturing independent exposure frames in response to pulses of different wavelengths of electromagnetic radiation. The alternative pulses may include red, green, and blue wavelengths for generating an RGB image frame consisting of a red exposure frame, a green exposure frame, and a blue exposure frame. In an alternative implementation, the alternative pulses may include luminance ("Y"), red chrominance ("Cr"), and blue chrominance "(Cb") pulses of light for generating a YCbCr image frame consisting of luminance data, red chrominance data, and blue chrominance data. The color image frame may further include data from a fluorescence exposure frame overlaid on the RGB or YCbCr image frame. The fluorescence pulse may include one or more pulses of electromagnetic radiation for eliciting a spectral response. In an embodiment, the fluorescence emission includes one or more of electromagnetic radiation having a wavelength from about 770 nm to about 790; or from about 795 nm to about 815 nm. Alternating the wavelengths of the pulsed electromagnetic radiation allows the full pixel array to be exploited and avoids the artifacts introduced by Bayer pattern pixel arrays.

In some instances, it is desirable to generate endoscopic imaging with multiple data types or multiple images overlaid on one another. For example, it may be desirable to generate a color (RGB or YCbCr) image that further includes fluorescence imaging data overlaid on the color image. An overlaid image of this nature may enable a medical practitioner or computer program to identify critical body structures based on the fluorescence imaging data. Historically, this would require the use of multiple sensor systems including an image sensor for color imaging and one or more additional image sensors for fluorescence imaging. In such systems, the multiple image sensors would have multiple types of pixel sensors that are each sensitive to distinct ranges of electromagnetic radiation. In systems known in the art, this includes the three separate types of pixel sensors for generating a color image along with additional pixel sensors for generating the fluorescence image data at different wavelengths of the electromagnetic spectrum. These multiple different pixel sensors consume a prohibitively large physical space and cannot be located at a distal tip of the endoscope. In systems known in the art, the camera or cameras are not placed at the distal tip of the endoscope and are instead placed in an endoscope handpiece or robotic unit. This introduces numerous disadvantages and causes the endoscope to be very delicate. The delicate endoscope may be damaged and image quality may be degraded when the endoscope is bumped or impacted during use. Considering the foregoing, disclosed herein are systems, methods, and devices for endoscopic imaging in a light deficient environment. The systems, methods, and devices disclosed herein provide means for employing multiple imaging techniques in a single imaging session while permitting one or more image sensors to be disposed in a distal tip of the endoscope.

Fluorescence Imaging

The systems, methods, and devices disclosed herein provide means for generating fluorescence imaging data in a light deficient environment. The fluorescence imaging data may be used to identify certain materials, tissues, components, or processes within a body cavity or other light deficient environment. In certain embodiments, fluorescence imaging is provided to a medical practitioner or computer-implemented program to enable the identification of certain structures or tissues within a body. Such fluorescence imaging data may be overlaid on black-and-white or RGB images to provide additional information and context.

Fluorescence is the emission of light by a substance that has absorbed light or other electromagnetic radiation. Certain fluorescent materials may "glow" or emit a distinct color that is visible to the human eye when the fluorescent material is subjected to ultraviolet light or other wavelengths of electromagnetic radiation. Certain fluorescent materials will cease to glow nearly immediately when the radiation source stops.

Fluorescence occurs when an orbital electron of a molecule, atom, or nanostructure is excited by light or other electromagnetic radiation, and then relaxes to its ground state by emitting a photon from the excited state. The specific frequencies of electromagnetic radiation that excite the orbital electron, or are emitted by the photon during relaxation, are dependent on the particular atom, molecule, or nanostructure. In most cases, the light emitted by the substance has a longer wavelength, and therefore lower energy, than the radiation that was absorbed by the substance. However, when the absorbed electromagnetic radiation is intense, it is possible for one electron to absorb two photons. This two-photon absorption can lead to emission of radiation having a shorter wavelength, and therefore higher energy, than the absorbed radiation. Additionally, the emitted radiation may also be the same wavelength as the absorbed radiation.

Fluorescence imaging has numerous practical applications, including mineralogy, gemology, medicine, spectroscopy for chemical sensors, detecting biological processes or signals, and so forth. Fluorescence may particularly be used in biochemistry and medicine as a non-destructive means for tracking or analyzing biological molecules. The biological molecules, including certain tissues or structures, may be tracked by analyzing the fluorescent emission of the biological molecules after being excited by a certain wavelength of electromagnetic radiation. However, relatively few cellular components are naturally fluorescent. In certain implementations, it may be desirable to visualize a certain tissue, structure, chemical process, or biological process that is not intrinsically fluorescent. In such an implementation, the body may be administered a dye or reagent that may include a molecule, protein, or quantum dot having fluorescent properties. The reagent or dye may then fluoresce after being excited by a certain wavelength of electromagnetic radiation. Different reagents or dyes may include different molecules, proteins, and/or quantum dots that will fluoresce at particular wavelengths of electromagnetic radiation. Thus, it may be necessary to excite the reagent or dye with a specialized band of electromagnetic radiation to achieve fluorescence and identify the desired tissue, structure, or process in the body.

Fluorescence imaging may provide valuable information in the medical field that may be used for diagnostic purposes and/or may be visualized in real-time during a medical procedure. Specialized reagents or dyes may be administered to a body to fluoresce certain tissues, structures, chemical processes, or biological processes. The fluorescence of the reagent or dye may highlight body structures such as blood vessels, nerves, particular organs, and so forth. Additionally, the fluorescence of the reagent or dye may highlight conditions or diseases such as cancerous cells or cells experiencing a certain biological or chemical process that may be associated with a condition or disease. The fluorescence imaging may be used in real-time by a medical practitioner or computer program for differentiating between, for example, cancerous and non-cancerous cells during a surgical tumor extraction. The fluorescence imaging may further be used as a non-destructive means for tracking and visualizing over time a condition in the body that would otherwise not be visible by the human eye or distinguishable in an RGB image.

The systems, methods, and devices for generating fluorescence imaging data may be used in coordination with reagents or dyes. Some reagents or dyes are known to attach to certain types of tissues and fluoresce at specific wavelengths of the electromagnetic spectrum. In an implementation, a reagent or dye is administered to a patient that is configured to fluoresce when activated by certain wavelengths of light. The endoscopic imaging system disclosed herein is used to excite and fluoresce the reagent or dye. The fluorescence of the reagent or dye is captured by the endoscopic imaging system to aid in the identification of tissues or structures in the body cavity. In an implementation, a patient is administered a plurality of reagents or dyes that are each configured to fluoresce at different wavelengths and/or provide an indication of different structures, tissues, chemical reactions, biological processes, and so forth. In such an implementation, the endoscopic imaging system emits each of the applicable wavelengths to fluoresce each of the applicable reagents or dyes. This may negate the need to perform individual imaging procedures for each of the plurality of reagents or dyes.

Imaging reagents can enhance imaging capabilities in pharmaceutical, medical, biotechnology, diagnostic, and medical procedure industries. Many imaging techniques such as X-ray, computer tomography (CT), ultrasound, magnetic resonance imaging (MRI), and nuclear medicine, mainly analyze anatomy and morphology and are unable to detect changes at the molecular level. Fluorescent reagents, dyes, and probes, including quantum dot nanoparticles and fluorescent proteins, assist medical imaging technologies by providing additional information about certain tissues, structures, chemical processes, and/or biological processes that are present within the imaging region. Imaging using fluorescent reagents enables cell tracking and/or the tracking of certain molecular biomarkers. Fluorescent reagents may be applied for imaging cancer, infection, inflammation, stem cell biology, and others. Numerous fluorescent reagents and dyes are being developed and applied for visualizing and tracking biological processes in a non-destructive manner. Such fluorescent reagents may be excited by a certain wavelength or band of wavelengths of electromagnetic radiation. Similarly, those fluorescent reagents may emit relaxation energy at a certain wavelength or band of wavelengths when fluorescing, and the emitted relaxation energy may be read by a sensor to determine the location and/or boundaries of the reagent or dye.

In an embodiment of the disclosure, an endoscopic imaging system pulses electromagnetic radiation for exciting an electron in a fluorescent reagent or dye. The endoscopic imaging system may pulse multiple different wavelengths of electromagnetic radiation for fluorescing multiple different reagents or dyes during a single imaging session. The endoscope includes an image sensor that is sensitive to the relaxation wavelength(s) of the one or more reagents or dyes. The imaging data generated by the image sensor can be used to identify a location and boundary of the one or more reagents or dyes. The endoscope system may further pulse electromagnetic radiation in red, green, and blue bands of visible light such that the fluorescence imaging can be overlaid on an RGB video stream.

Pulsed Imaging

Some implementations of the disclosure include aspects of a combined sensor and system design that allows for high definition imaging with reduced pixel counts in a controlled illumination environment. This is accomplished with frame-by-frame pulsing of a single-color wavelength and switching or alternating each frame between a single, different color wavelength using a controlled light source in conjunction with high frame capture rates and a specially designed corresponding monochromatic sensor. Additionally, electromagnetic radiation outside the visible light spectrum may be pulsed to enable the generation of a hyperspectral image. The pixels may be color agnostic such that each pixel generates data for each pulse of electromagnetic radiation, including pulses for red, green, and blue visible light wavelengths along with other wavelengths used for hyperspectral imaging.

A system of the disclosure is an endoscopic imaging system for use in a light deficient environment. The system includes an endoscope comprising an image sensor, wherein the image sensor is configured to sense reflected electromagnetic radiation for generating a plurality of exposure frames that can be combined to generate an RGB image frame with hyperspectral data overlaid thereon. The system includes an emitter for emitting pulses of electromagnetic radiation. The system includes a controller (may alternatively be referred to as a "control circuit" in electronic communication with the image sensor and the emitter. The controller controls a duty cycle of the emitter in response to signals corresponding to a duty cycle of the emitter. The image sensor includes bidirectional pads that can send and receive information. The bidirectional pads of the image sensor operate in a frame period divided into three defined states, including a rolling readout state, a service line state, and a configuration state. The system includes an oscillator disposed in the controller and a frequency detector connected to the controller. The frequency detector controls a clock frequency of the image sensor in response to signals from the controller that correspond to the frequency of the oscillator. The system is such that clock signal data is transmitted from the bidirectional pads of the image sensor to the controller during the service line phase and the configuration phase. The system is such that exposure frames are synchronized without the use of an input clock or a data transmission clock.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the structure, systems and methods for producing an image in a light deficient environment are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

As used herein, color sensors or multi spectrum sensors are those sensors known to have a color filter array (CFA) thereon to filter the incoming electromagnetic radiation into its separate components. In the visual range of the electromagnetic spectrum, such a CFA may be built on a Bayer pattern or modification thereon to separate green, red and blue spectrum components of the light.

As used herein, monochromatic sensor refers to an unfiltered imaging sensor. Since the pixels are color agnostic, the effective spatial resolution is appreciably higher than for their color (typically Bayer-pattern filtered) counterparts in conventional single-sensor cameras. Monochromatic sensors may also have higher quantum efficiency because fewer incident photons are wasted between individual pixels.

As used herein, an emitter is a device that is capable of generating and emitting electromagnetic pulses. Various embodiments of emitters may be configured to emit pulses and have very specific frequencies or ranges of frequencies from within the entire electromagnetic spectrum. Pulses may comprise wavelengths from the visible and non-visible ranges. An emitter may be cycled on and off to produce a pulse or may produce a pulse with a shutter mechanism. An emitter may have variable power output levels or may be controlled with a secondary device such as an aperture or filter. An emitter may emit broad spectrum or full spectrum electromagnetic radiation that may produce pulses through color filtering or shuttering. An emitter may comprise a plurality of electromagnetic sources that act individually or in concert.

It should be noted that as used herein the term "light" is both a particle and a wavelength and is intended to denote electromagnetic radiation that is detectable by a pixel array 122 and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

Referring now to the figures, FIG. 1 illustrates a schematic diagram of a system 100 for sequential pulsed imaging in a light deficient environment. The system 100 can be deployed to generate an RGB image with fluorescence imaging data overlaid on the RGB image. The system 100 includes an emitter 102 and a pixel array 122. The emitter 102 pulses a partition of electromagnetic radiation in the light deficient environment 112 and the pixel array 122 senses instances of reflected electromagnetic radiation. The emitter 102 and the pixel array 122 work in sequence such that one or more pulses of a partition of electromagnetic radiation results in image data sensed by the pixel array 122.

It should be noted that as used herein the term "light" is both a particle and a wavelength and is intended to denote electromagnetic radiation that is detectable by a pixel array 122 and may include wavelengths from the visible and non-visible spectrums of electromagnetic radiation. The term "partition" is used herein to mean a pre-determined range of wavelengths of the electromagnetic spectrum that is less than the entire spectrum, or in other words, wavelengths that make up some portion of the electromagnetic spectrum. As used herein, an emitter is a light source that may be controllable as to the portion of the electromagnetic spectrum that is emitted or that may operate as to the physics of its components, the intensity of the emissions, or the duration of the emission, or all the above. An emitter may emit light in any dithered, diffused, or collimated emission and may be controlled digitally or through analog methods or systems. As used herein, an electromagnetic emitter is a source of a burst of electromagnetic energy and includes light sources, such as lasers, LEDs, incandescent light, or any light source that can be digitally controlled.

A pixel array 122 of an image sensor may be paired with the emitter 102 electronically, such that the emitter 102 and the pixel array 122 are synced during operation for both receiving the emissions and for the adjustments made within the system. The emitter 102 may be tuned to emit electromagnetic radiation in the form of a laser, which may be pulsed to illuminate a light deficient environment 112. The emitter 102 may pulse at an interval that corresponds to the operation and functionality of the pixel array 122. The emitter 102 may pulse light in a plurality of electromagnetic partitions such that the pixel array receives electromagnetic energy and produces a dataset that corresponds in time with each specific electromagnetic partition. For example, FIG. 1 illustrates an implementation wherein the emitter 102 emits four different partitions of electromagnetic radiation, including red 104, green 106, blue 108, and a fluorescence excitation 110 wavelength. The fluorescence excitation 110 wavelength may include a plurality of different partitions of electromagnetic radiation that are selected to fluoresce a plurality of fluorescent reagents that are present within the light deficient environment 112. The fluorescent excitation 110 wavelength may be selected to fluoresce a particular fluorescent reagent that is present in the light deficient environment 112.

In an alternative embodiment not illustrated in FIG. 1, the pulsed emissions of light include a luminance ("Y") emission, a red chrominance ("Cr") emission, and a blue chrominance ("Cb") emission in place of the pulsed red 104, pulsed green 106, and pulsed blue 108 emissions. In an embodiment, the controller or the emitter 102 modules the pulses of electromagnetic radiation to provide luminance and/or chrominance information according to color transformation coefficients that convert light energy from red, green, and blue light energy spaces to luminance, red chrominance, and blue chrominance light energy space. The pulsed emissions of light may further include modulated blue chrominance ("Y+Cb") pulses and/or modulated red chrominance ("Y+Cr") pulses.

The light deficient environment 112 includes structures, tissues, and other elements that reflect a combination of red 114, green 116, and/or blue 118 light. A structure that is perceived as being red 114 will reflect back pulsed red 104 light. The reflection off the red structure results in sensed red 105 by the pixel array 122 following the pulsed red 104 emission. The data sensed by the pixel array 122 results in a red exposure frame. A structure that is perceived as being green 116 will reflect back pulsed green 106 light. The reflection off the green structure results in sensed green 107 by the pixel array 122 following the pulsed green 106 emission. The data sensed by the pixel array 122 results in a green exposure frame. A structure that is perceived as being blue 118 will reflect back pulsed blue 108 light. The reflection off the blue structure results in sensed blue 109 by the pixel array 122 following the pulsed blue 108 emission. The data sensed by the pixel array 122 results in a blue exposure frame.

When a structure is a combination of colors, the structure will reflect back a combination of the pulsed red 104, pulsed green 106, and/or pulsed blue 108 emissions. For example, a structure that is perceived as being purple will reflect back light from the pulsed red 104 and pulsed blue 108 emissions. The resulting data sensed by the pixel array 122 will indicate that light was reflected in the same region following the pulsed red 104 and pulsed blue 108 emissions. When the resultant red exposure frame and blue exposure frames are combined to form the RGB image frame, the RGB image frame will indicate that the structure is purple.

In an embodiment where the light deficient environment 112 includes a fluorescent reagent or dye or includes one or more fluorescent structures, tissues, or other elements, the pulsing scheme may include the emission of a certain fluorescence excitation wavelength. The certain fluorescence excitation wavelength may be selected to fluoresce a known fluorescent reagent, dye, or other structure. The fluorescent structure will be sensitive to the fluorescence excitation wavelength and will emit a fluorescence relaxation wavelength. The fluorescence relaxation wavelength will be sensed by the pixel array 122 following the emission of the fluorescence excitation wavelength. The data sensed by the pixel array 122 results in a fluorescence exposure frame. The fluorescence exposure frame may be combined with multiple other exposure frames to form an image frame. The data in the fluorescence exposure frame may be overlaid on an RGB image frame that includes data from a red exposure frame, a green exposure frame, and a blue exposure frame.

In an embodiment where the light deficient environment 112 includes structures, tissues, or other materials that emit a spectral response to certain partitions of the electromagnetic spectrum, the pulsing scheme may include the emission of a hyperspectral partition of electromagnetic radiation for the purpose of eliciting the spectral response from the structures, tissues, or other materials present in the light deficient environment 112. The spectral response includes the emission or reflection of certain wavelengths of electromagnetic radiation. The spectral response can be sensed by the pixel array 122 and result in a hyperspectral exposure frame. The hyperspectral exposure frame may be combined with multiple other exposure frames to form an image frame. The data in the hyperspectral exposure frame may be overlaid on an RGB image frame that includes data from a red exposure frame, a green exposure frame, and a blue exposure frame.

In an embodiment, the pulsing scheme includes the emission of a laser mapping or tool tracking pattern. The reflected electromagnetic radiation sensed by the pixel array 122 following the emission of the laser mapping or tool tracking pattern results in a laser mapping exposure frame. The data in the laser mapping exposure frame may be provided to a corresponding system to identify, for example, distances between tools present in the light deficient environment 112, a three-dimensional surface topology of a scene in the light deficient environment 112, distances, dimensions, or positions of structures or objects within the scene, and so forth. This data may be overlaid on an RGB image frame or otherwise provided to a user of the system.

The emitter 102 may be a laser emitter that is capable of emitting pulsed red 104 light for generating sensed red 105 data for identifying red 114 elements within the light deficient environment 112. The emitter 102 is further capable of emitting pulsed green 106 light for generating sensed green 107 data for identifying green 116 elements within the light deficient environment. The emitter 102 is further capable of emitting pulsed blue 108 light for generating sensed blue 109 data for identifying blue 118 elements within the light deficient environment. The emitter 102 is further capable of emitting pulsed fluorescence excitation 110 wavelength(s) of electromagnetic radiation for identifying a fluorescent reagent 120 within the light deficient environment 112. The fluorescent reagent 120 is identified by exciting the fluorescent reagent 120 with the pulsed fluorescence excitation 110 light and then sensing (by the pixel array 122) the fluorescence relaxation 111 wavelength for that particular fluorescent reagent 120. The emitter 102 is capable of emitting the pulsed red 104, pulsed green 106, pulsed blue 108, and pulsed fluorescence excitation 110 wavelengths in any desired sequence.

The pixel array 122 senses reflected electromagnetic radiation. Each of the sensed red 105, the sensed green 107, the sensed blue 109, and the sensed fluorescence relaxation 111 data can be referred to as an "exposure frame." Each exposure frame is assigned a specific color or wavelength partition, wherein the assignment is based on the timing of the pulsed color or wavelength partition from the emitter 102. The exposure frame in combination with the assigned specific color or wavelength partition may be referred to as a dataset. Even though the pixels 122 are not color-dedicated, they can be assigned a color for any given dataset based on a priori information about the emitter.

For example, during operation, after pulsed red 104 light is pulsed in the light deficient environment 112, the pixel array 122 senses reflected electromagnetic radiation. The reflected electromagnetic radiation results in an exposure frame, and the exposure frame is catalogued as sensed red 105 data because it corresponds in time with the pulsed red 104 light. The exposure frame in combination with an indication that it corresponds in time with the pulsed red 104 light is the "dataset." This is repeated for each partition of electromagnetic radiation emitted by the emitter 102. The data created by the pixel array 122 includes the sensed red 105 exposure frame identifying red 114 components in the light deficient environment and corresponding in time with the pulsed red 104 light. The data further includes the sensed green 107 exposure frame identifying green 116 components in the light deficient environment and corresponding in time with the pulsed green 106 light. The data further includes the sensed blue 109 exposure frame identifying blue 118 components in the light deficient environment and corresponding in time with the pulsed blue 108 light. The data further includes the sensed fluorescence relaxation 111 exposure frame identifying the fluorescent reagent 120 and corresponding in time with the pulsed fluorescence excitation 110 wavelength(s) of light.

In one embodiment, three datasets representing RED, GREEN and BLUE electromagnetic pulses are combined to form a single image frame. Thus, the information in a red exposure frame, a green exposure frame, and a blue exposure frame are combined to form a single RGB image frame. One or more additional datasets representing other wavelength partitions may be overlaid on the single RGB image frame. The one or more additional datasets may represent, for example, fluorescence imaging responsive to the pulsed excitation 110 wavelength between 770 nm and 790 nm and between 795 nm and 815 nm.

It will be appreciated that the disclosure is not limited to any particular color combination or any particular electromagnetic partition, and that any color combination or any electromagnetic partition may be used in place of RED, GREEN and BLUE, such as Cyan, Magenta and Yellow; Ultraviolet; infrared; any combination of the foregoing, or any other color combination, including all visible and non-visible wavelengths, without departing from the scope of the disclosure. In the figure, the light deficient environment 112 to be imaged includes red 114, green 116, and blue 118 portions, and further includes a fluorescent reagent 120. As illustrated in the figure, the reflected light from the electromagnetic pulses only contains the data for the portion of the object having the specific color that corresponds to the pulsed color partition. Those separate color (or color interval) datasets can then be used to reconstruct the image by combining the datasets at 126. The information in each of the multiple exposure frames (i.e., the multiple datasets) may be combined by a controller 124, a control unit, a camera control unit, the image sensor, an image signal processing pipeline, or some other computing resource that is configurable to process the multiple exposure frames and combine the datasets at 126. The datasets may be combined to generate the single image frame within the endoscope unit itself or offsite by some other processing resource.

Figure 2:
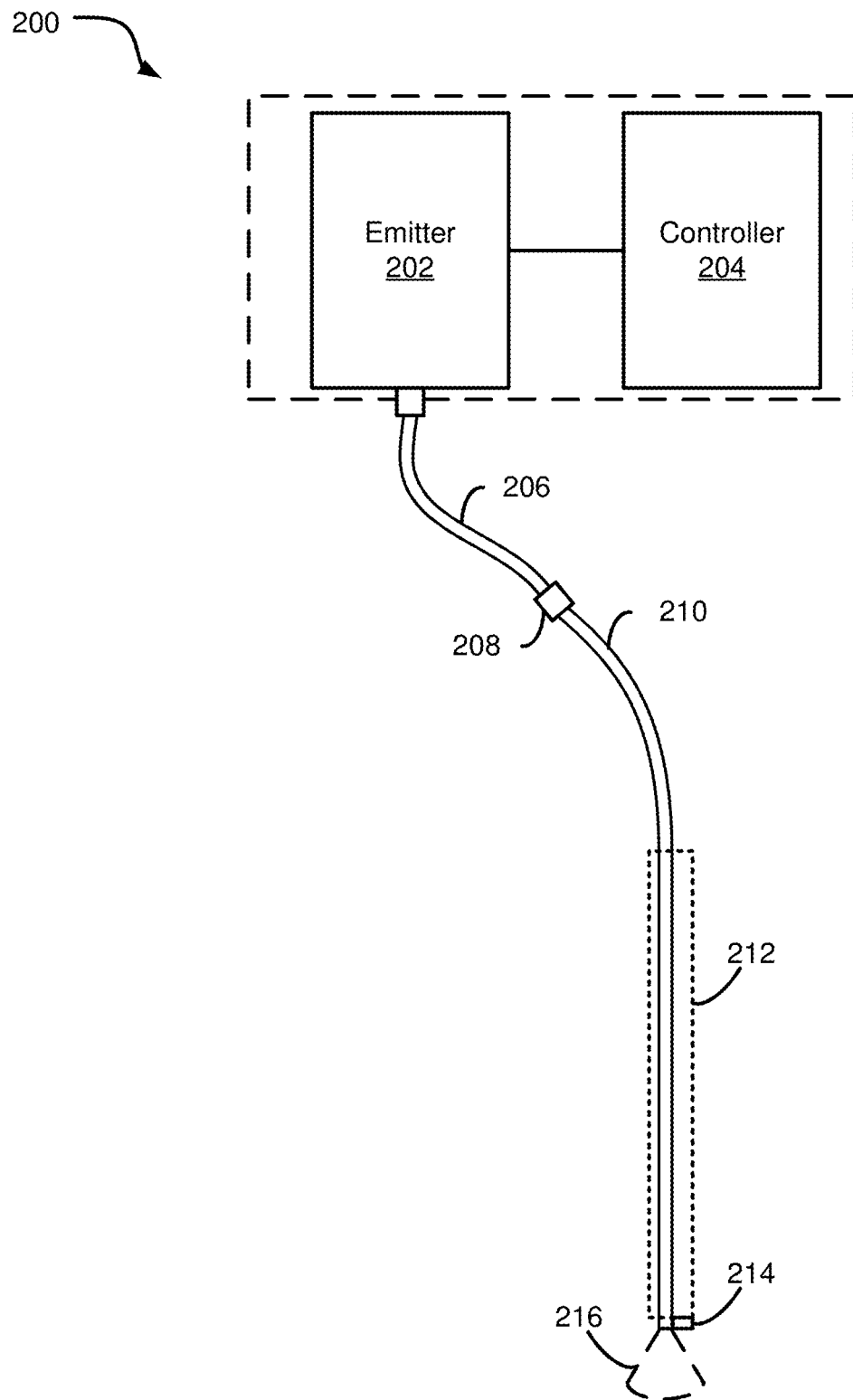
FIG. 2 is a system for providing illumination to a light deficient environment for endoscopic imaging.

FIG. 2 is a system 200 for providing illumination to a light deficient environment, such as for endoscopic imaging. The system 200 may be used in combination with any of the systems, methods, or devices disclosed herein. The system 200 includes an emitter 202, a controller 204, a jumper waveguide 206, a waveguide connector 208, a lumen waveguide 210, a lumen 212, and an image sensor 214 with accompanying optical components (such as a lens). The emitter 202 (may be generically referred to as a "light source") generates light that travels through the jumper waveguide 206 and the lumen waveguide 210 to illuminate a scene at a distal end of the lumen 212. The emitter 202 may be used to emit any wavelength of electromagnetic energy including visible wavelengths, infrared, ultraviolet, hyperspectral, fluorescence excitation, laser mapping pulsing schemes, or other wavelengths. The lumen 212 may be inserted into a patient's body for imaging, such as during a procedure or examination. The light is output as illustrated by dashed lines 216. A scene illuminated by the light may be captured using the image sensor 214 and displayed for a doctor or some other medical personnel. The controller 204 may provide control signals to the emitter 202 to control when illumination is provided to a scene. In one embodiment, the emitter 202 and controller 204 are located within a camera control unit (CCU) or external console to which an endoscope is connected. If the image sensor 214 includes a CMOS sensor, light may be periodically provided to the scene in a series of illumination pulses between readout periods of the image sensor 214 during what is known as a blanking period. Thus, the light may be pulsed in a controlled manner to avoid overlapping into readout periods of the image pixels in a pixel array of the image sensor 214.

In one embodiment, the lumen waveguide 210 includes one or more optical fibers. The optical fibers may be made of a low-cost material, such as plastic to allow for disposal of the lumen waveguide 210 and/or other portions of an endoscope. In one embodiment, the lumen waveguide 210 is a single glass fiber having a diameter of 500 microns. The jumper waveguide 206 may be permanently attached to the emitter 202. For example, a jumper waveguide 206 may receive light from an emitter within the emitter 202 and provide that light to the lumen waveguide 210 at the location of the connector 208. In one embodiment, the jumper waveguide 106 includes one or more glass fibers. The jumper waveguide may include any other type of waveguide for guiding light to the lumen waveguide 210. The connector 208 may selectively couple the jumper waveguide 206 to the lumen waveguide 210 and allow light within the jumper waveguide 206 to pass to the lumen waveguide 210. In one embodiment, the lumen waveguide 210 is directly coupled to a light source without any intervening jumper waveguide 206.

The image sensor 214 includes a pixel array. In an embodiment, the image sensor 214 includes two or more pixel arrays for generating a three-dimensional image. The image sensor 214 may constitute two more image sensors that each have an independent pixel array and can operate independent of one another. The pixel array of the image sensor 214 includes active pixels and optical black ("OB") or optically blind pixels. The active pixels may be clear "color agnostic" pixels that are capable of sensing imaging data for any wavelength of electromagnetic radiation. The optical black pixels are read during a blanking period of the pixel array when the pixel array is "reset" or calibrated. In an embodiment, light is pulsed during the blanking period of the pixel array when the optical black pixels are being read. After the optical black pixels have been read, the active pixels are read during a readout period of the pixel array. The active pixels may be charged by the electromagnetic radiation that is pulsed during the blanking period such that the active pixels are ready to be read by the image sensor during the readout period of the pixel array.

Figure 2A:
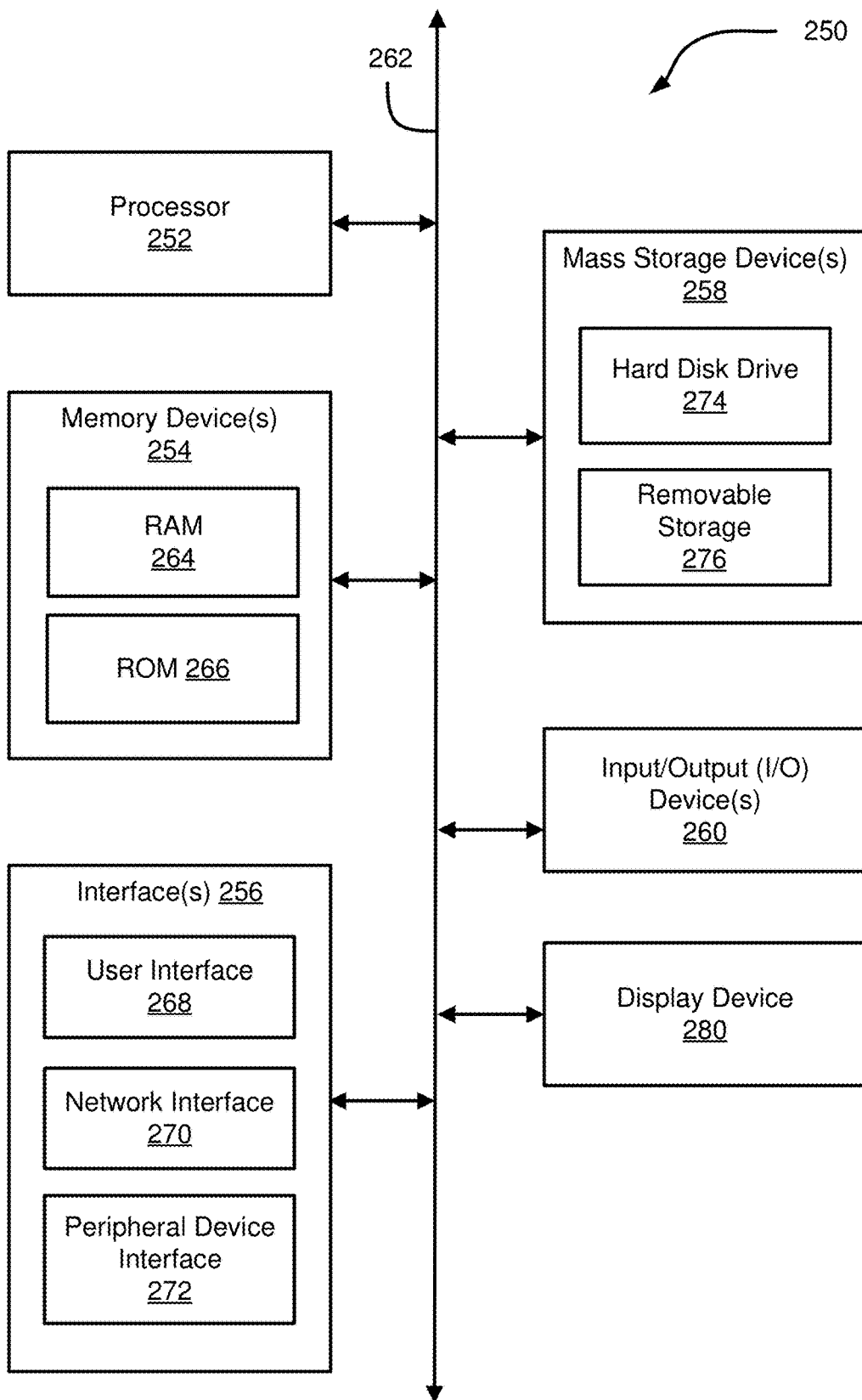
FIG. 2A is a schematic diagram of complementary system hardware.

FIG. 2A is a schematic diagram of complementary system hardware such as a special purpose or general-purpose computer. Implementations within the scope of the present disclosure may also include physical and other non-transitory computer readable media for carrying or storing computer executable instructions and/or data structures. Such computer readable media can be any available media that can be accessed by a general purpose or special purpose computer system. Computer readable media that stores computer executable instructions are computer storage media (devices). Computer readable media that carry computer executable instructions are transmission media. Thus, by way of example, and not limitation, implementations of the disclosure can comprise at least two distinctly different kinds of computer readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer executable instructions or data structures and which can be accessed by a general purpose or special purpose computer. Combinations of the above should also be included within the scope of computer readable media.

Further, upon reaching various computer system components, program code means in the form of computer executable instructions or data structures that can be transferred automatically from transmission media to computer storage media (devices) (or vice versa). For example, computer executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered storage, such as FusionIO). Thus, it should be understood that computer storage media (devices) can be included in computer system components that also (or even primarily) utilize transmission media.

Computer executable instructions comprise, for example, instructions and data which, when executed by one or more processors, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above-mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 2A is a block diagram illustrating an example computing device 250. Computing device 250 may be used to perform various procedures, such as those discussed herein. Computing device 250 can function as a server, a client, or any other computing entity. Computing device 250 can perform various monitoring functions as discussed herein, and can execute one or more application programs, such as the application programs described herein. Computing device 250 can be any of a wide variety of computing devices, such as a desktop computer, a notebook computer, a server computer, a handheld computer, camera control unit, tablet computer and the like.

Computing device 250 includes one or more processor(s) 252, one or more memory device(s) 254, one or more interface(s) 256, one or more mass storage device(s) 258, one or more Input/Output (I/O) device(s) 260, and a display device 280 all of which are coupled to a bus 262. Processor(s) 252 include one or more processors or controllers that execute instructions stored in memory device(s) 254 and/or mass storage device(s) 258. Processor(s) 252 may also include various types of computer readable media, such as cache memory.

Memory device(s) 254 include various computer readable media, such as volatile memory (e.g., random access memory (RAM) 264) and/or nonvolatile memory (e.g., read-only memory (ROM) 266). Memory device(s) 254 may also include rewritable ROM, such as Flash memory.

Mass storage device(s) 258 include various computer readable media, such as magnetic tapes, magnetic disks, optical disks, solid-state memory (e.g., Flash memory), and so forth. As shown in FIG. 2, a particular mass storage device is a hard disk drive 274. Various drives may also be included in mass storage device(s) 258 to enable reading from and/or writing to the various computer readable media. Mass storage device(s) 258 include removable media 276 and/or non-removable media.

I/O device(s) 260 include various devices that allow data and/or other information to be input to or retrieved from computing device 250. Example I/O device(s) 260 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 280 includes any type of device capable of displaying information to one or more users of computing device 250. Examples of display device 280 include a monitor, display terminal, video projection device, and the like.

Interface(s) 256 include various interfaces that allow computing device 250 to interact with other systems, devices, or computing environments. Example interface(s) 256 may include any number of different network interfaces 270, such as interfaces to local area networks (LANs), wide area networks (WANs), wireless networks, and the Internet. Other interface(s) include user interface 268 and peripheral device interface 272. The interface(s) 256 may also include one or more user interface elements 268. The interface(s) 256 may also include one or more peripheral interfaces such as interfaces for printers, pointing devices (mice, track pad, etc.), keyboards, and the like.

Bus 262 allows processor(s) 252, memory device(s) 254, interface(s) 256, mass storage device(s) 258, and I/O device(s) 260 to communicate with one another, as well as other devices or components coupled to bus 262. Bus 262 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 250 and are executed by processor(s) 252. Alternatively, the systems and procedures described herein can be implemented in hardware, or a combination of hardware, software, and/or firmware. For example, one or more application specific integrated circuits (ASICs) or field programmable gate arrays (FPGAs) can be programmed to carry out one or more of the systems and procedures described herein.

Figure 3A:
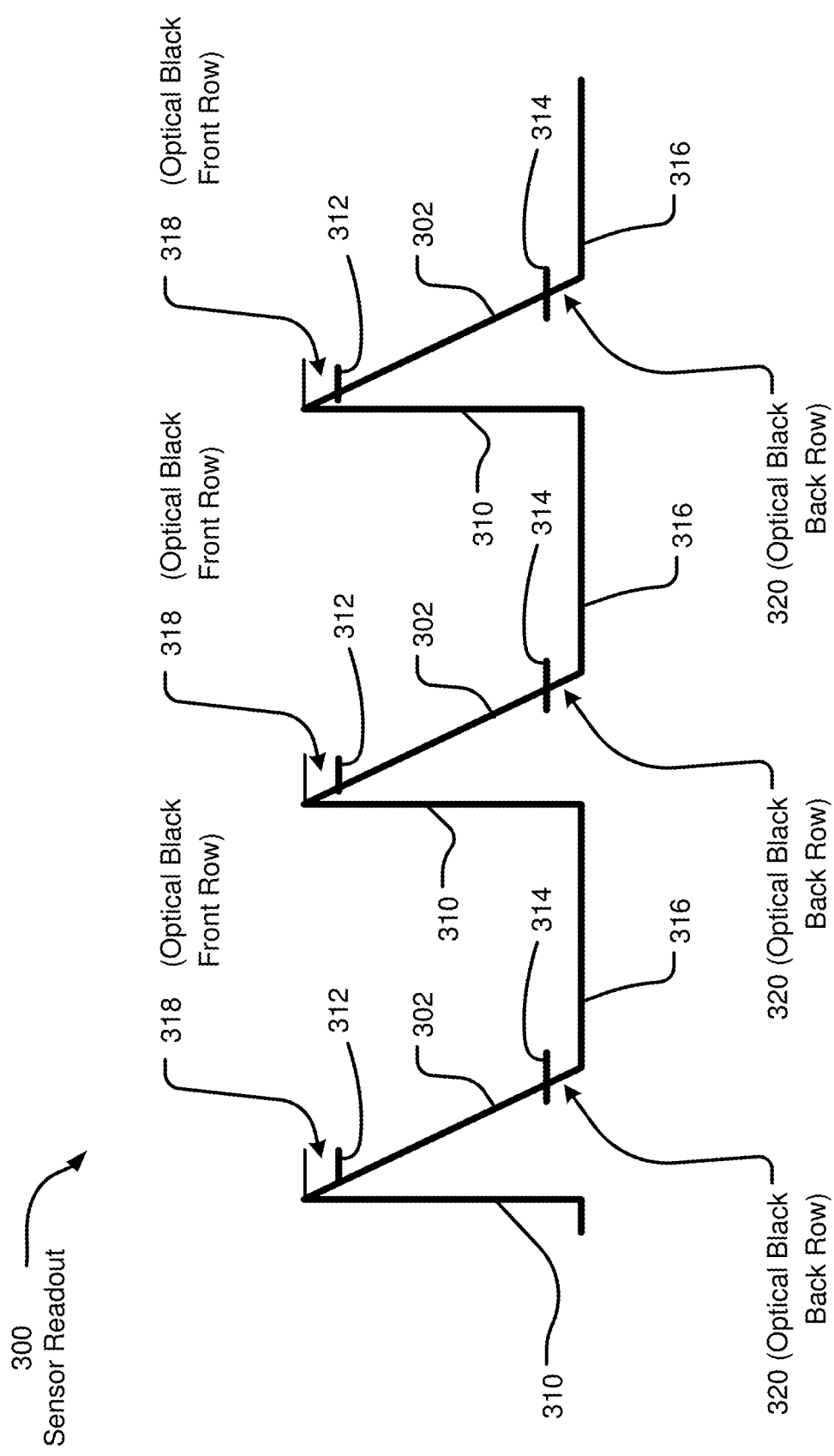
FIGS. 3A to 3D are illustrations of the operational cycles of a sensor used to construct an exposure frame.

FIG. 3A illustrates the operational cycles of a sensor used in rolling readout mode or during the sensor readout 300. The frame readout period may start at and may be represented by vertical line 310. The readout period 302 is represented by the diagonal or slanted line. The sensor may be read out on a row by row basis, the top of the downwards slanted edge being the sensor top row 312 and the bottom of the downwards slanted edge being the sensor bottom row 314. The time between the last row readout and the next readout period may be called the blanking period 316. It should be noted that some of the sensor pixel rows might be covered with a light shield (e.g., a metal coating or any other substantially black layer of another material type). These covered pixel rows may be referred to as optical black rows 318 and 320. Optical black rows 318 and 320 may be used as input for correction algorithms. As shown in FIG. 3A, these optical black rows 318 and 320 may be located on the top of the pixel array or at the bottom of the pixel array or at the top and the bottom of the pixel array.

Figure 3B:
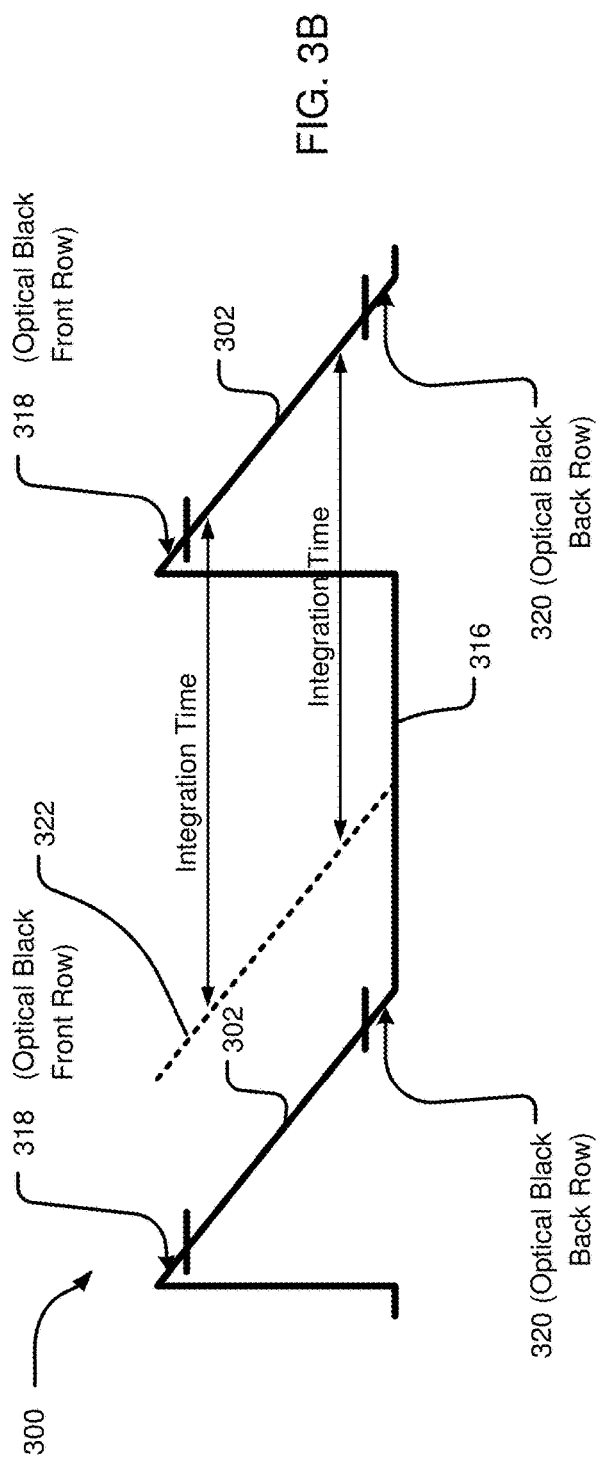

FIG. 3B illustrates a process of controlling the amount of electromagnetic radiation, e.g., light, that is exposed to a pixel, thereby integrated or accumulated by the pixel. It will be appreciated that photons are elementary particles of electromagnetic radiation. Photons are integrated, absorbed, or accumulated by each pixel and converted into an electrical charge or current. An electronic shutter or rolling shutter (shown by dashed line 322) may be used to start the integration time by resetting the pixel. The light will then integrate until the next readout period. The position of the electronic shutter 322 can be moved between two readout periods 302 to control the pixel saturation for a given amount of light. It should be noted that this technique allows for a constant integration time between two different lines but introduces a delay when moving from top to bottom rows.

Figure 3C:
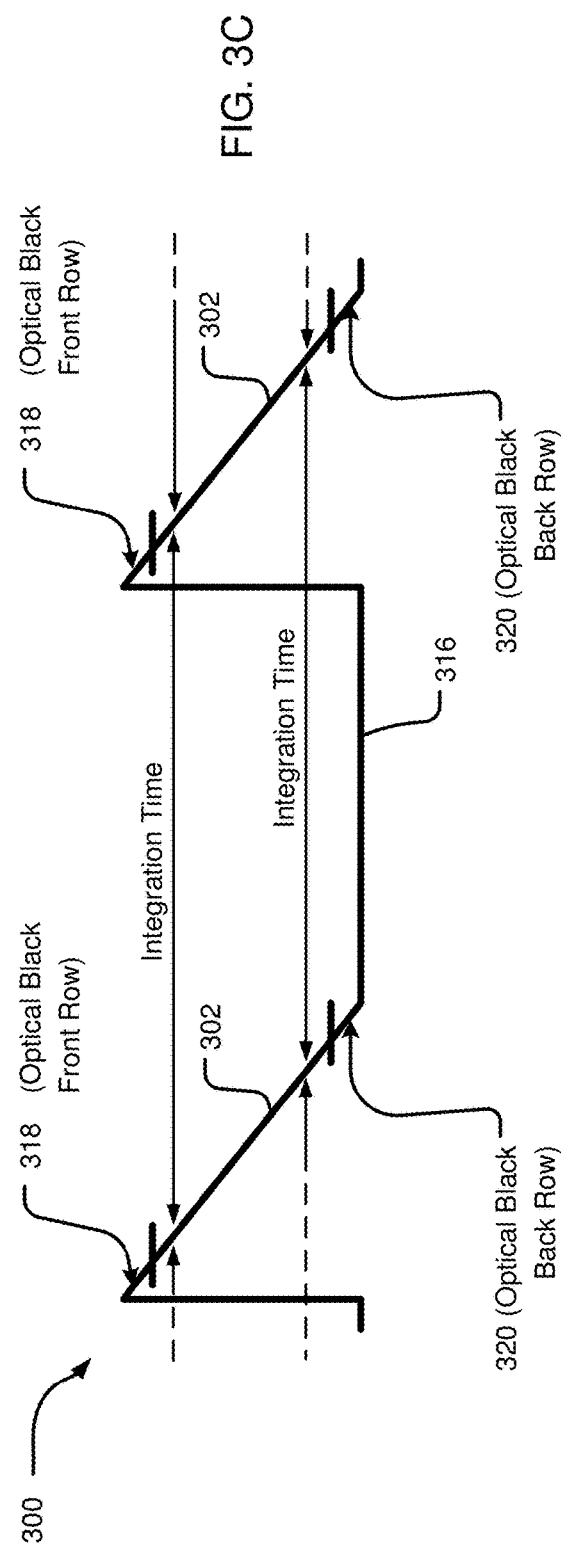

FIG. 3C illustrates the case where the electronic shutter 322 has been removed. In this configuration, the integration of the incoming light may start during the readout period 302 and may end at the next readout period 302, which also defines the start of the next integration.

Figure 3D:
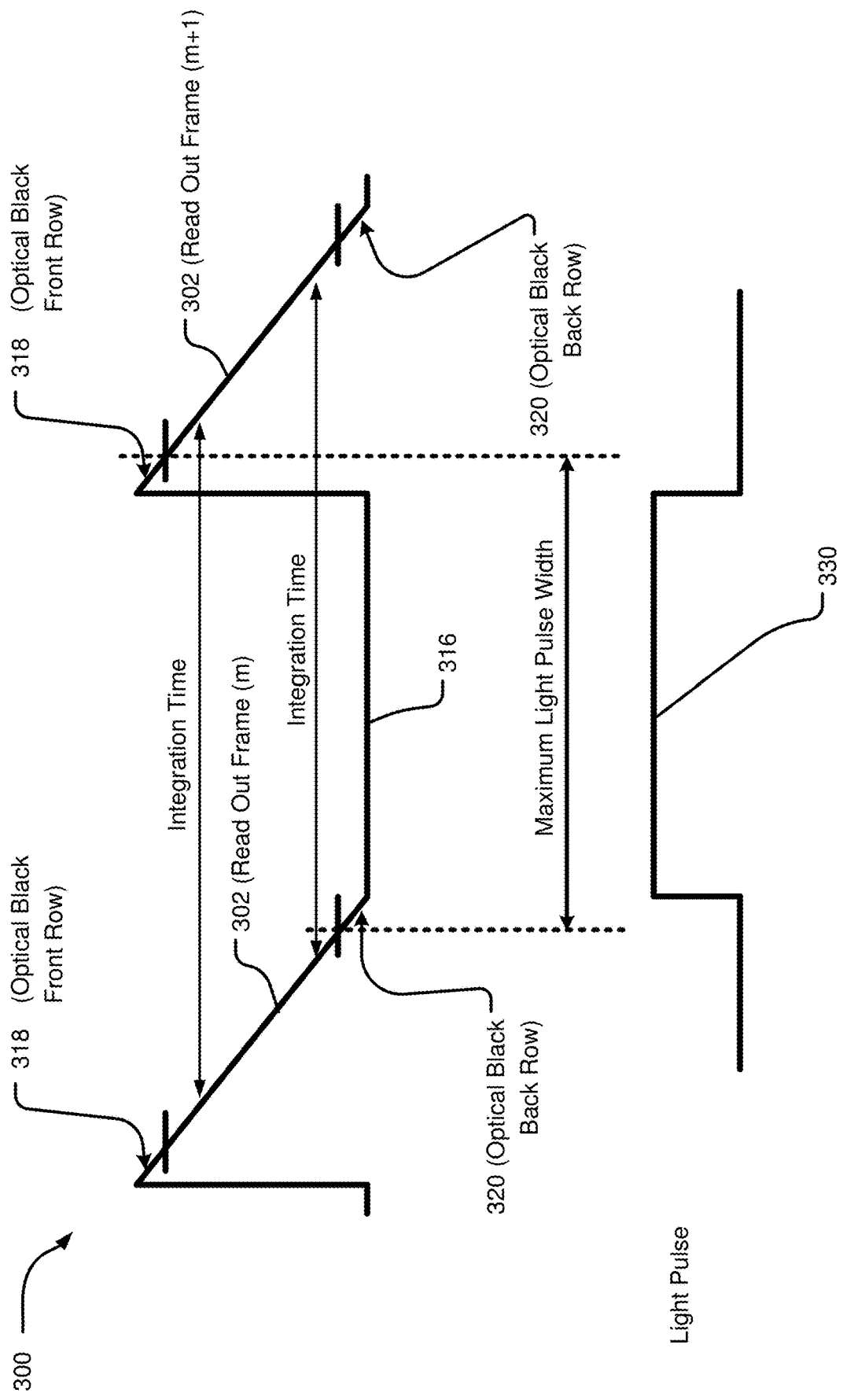

FIG. 3D shows a configuration without an electronic shutter 322, but with a controlled and pulsed light 330 during the blanking period 316. This ensures that all rows see the same light issued from the same light pulse 330. In other words, each row will start its integration in a dark environment, which may be at the optical black back row 320 of read out frame (m) for a maximum light pulse width, and will then receive a light strobe and will end its integration in a dark environment, which may be at the optical black front row 318 of the next succeeding read out frame (m+1) for a maximum light pulse width. In the FIG. 3D example, the image generated from the light pulse will be solely available during frame (m+1) readout without any interference with frames (m) and (m+2). It should be noted that the condition to have a light pulse to be read out only in one frame and not interfere with neighboring frames is to have the given light pulse firing during the blanking period 316. Because the optical black rows 318, 320 are insensitive to light, the optical black back rows 320 time of frame (m) and the optical black front rows 318 time of frame (m+1) can be added to the blanking period 316 to determine the maximum range of the firing time of the light pulse 330.

As illustrated in the FIG. 3A, a sensor may be cycled many times to receive data for each pulsed color or wavelength (e.g., Red, Green, Blue, or other wavelength on the electromagnetic spectrum). Each cycle may be timed. In an embodiment, the cycles may be timed to operate within an interval of 16.67 ms. In another embodiment, the cycles may be timed to operate within an interval of 8.3 ms. It will be appreciated that other timing intervals are contemplated by the disclosure and are intended to fall within the scope of this disclosure.

Figure 4A:
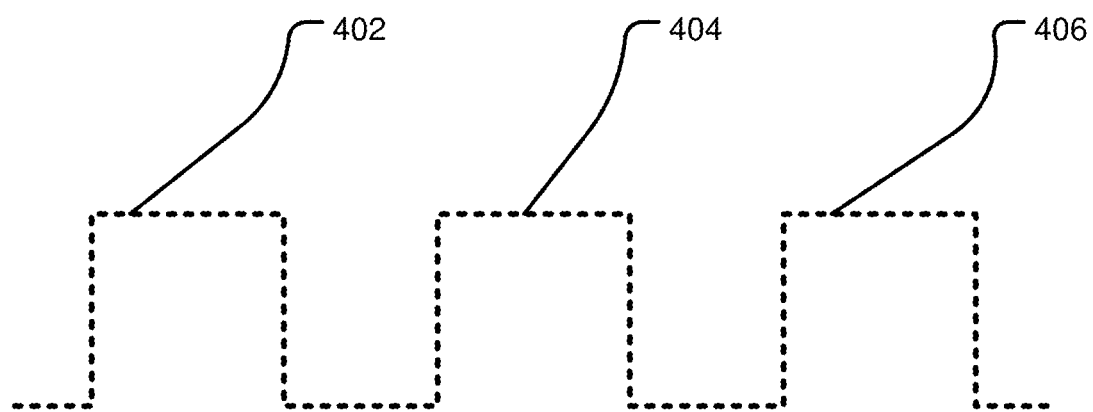
FIG. 4A is a graphical representation of the operation of an embodiment of an electromagnetic emitter.

FIG. 4A graphically illustrates the operation of an embodiment of an electromagnetic emitter. An emitter may be timed to correspond with the cycles of a sensor, such that electromagnetic radiation is emitted within the sensor operation cycle and/or during a portion of the sensor operation cycle. FIG. 4A illustrates Pulse 1 at 402, Pulse 2 at 404, and Pulse 3 at 406. In an embodiment, the emitter may pulse during the readout period 302 of the sensor operation cycle. In an embodiment, the emitter may pulse during the blanking period 316 of the sensor operation cycle. In an embodiment, the emitter may pulse for a duration that is during portions of two or more sensor operational cycles. In an embodiment, the emitter may begin a pulse during the blanking period 316, or during the optical black portion 320 of the readout period 302, and end the pulse during the readout period 302, or during the optical black portion 318 of the readout period 302 of the next succeeding cycle. It will be understood that any combination of the above is intended to fall within the scope of this disclosure as long as the pulse of the emitter and the cycle of the sensor correspond.

Figure 4B:
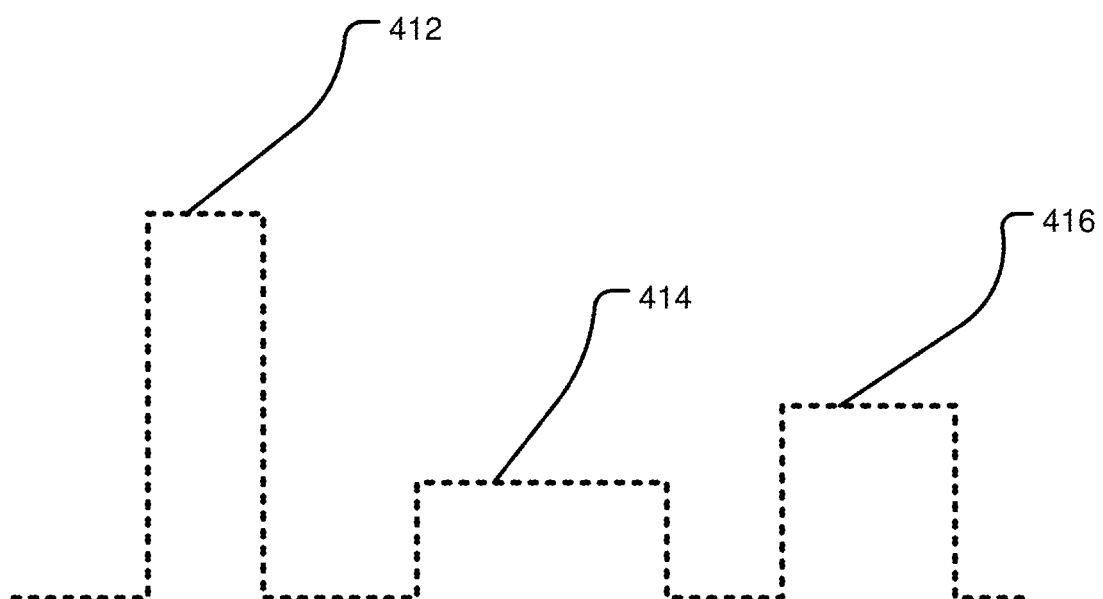
FIG. 4B is a graphical representation of varying the duration and magnitude of the emitted electromagnetic pulse to provide exposure control.

FIG. 4B graphically represents varying the duration and magnitude of the emitted electromagnetic pulse (e.g., Pulse 1 at 412, Pulse 2 at 414, and Pulse 3 at 416) to control exposure. An emitter having a fixed output magnitude may be pulsed during any of the cycles noted above in relation to FIGS. 3D and 4A for an interval to provide the needed electromagnetic energy to the pixel array. An emitter having a fixed output magnitude may be pulsed at a longer interval of time, thereby providing more electromagnetic energy to the pixels or the emitter may be pulsed at a shorter interval of time, thereby providing less electromagnetic energy. Whether a longer or shorter interval time is needed depends upon the operational conditions.

In contrast to adjusting the interval of time the emitter pulses a fixed output magnitude, the magnitude of the emission itself may be increased to provide more electromagnetic energy to the pixels. Similarly, decreasing the magnitude of the pulse provides less electromagnetic energy to the pixels. It should be noted that an embodiment of the system may have the ability to adjust both magnitude and duration concurrently, if desired. Additionally, the sensor may be adjusted to increase its sensitivity and duration as desired for optimal image quality. FIG. 4B illustrates varying the magnitude and duration of the pulses. In the illustration, Pulse 1 at 412 has a higher magnitude or intensity than either Pulse 2 at 414 or Pulse 3 at 416. Additionally, Pulse 1 at 412 has a shorter duration than Pulse 2 at 414 or Pulse 3 at 416, such that the electromagnetic energy provided by the pulse is illustrated by the area under the pulse shown in the illustration. In the illustration, Pulse 2 at 414 has a relatively low magnitude or intensity and a longer duration when compared to either Pulse 1 at 412 or Pulse 3 at 416. Finally, in the illustration, Pulse 3 at 416 has an intermediate magnitude or intensity and duration, when compared to Pulse 1 at 412 and Pulse 2 at 414.

Figure 5:
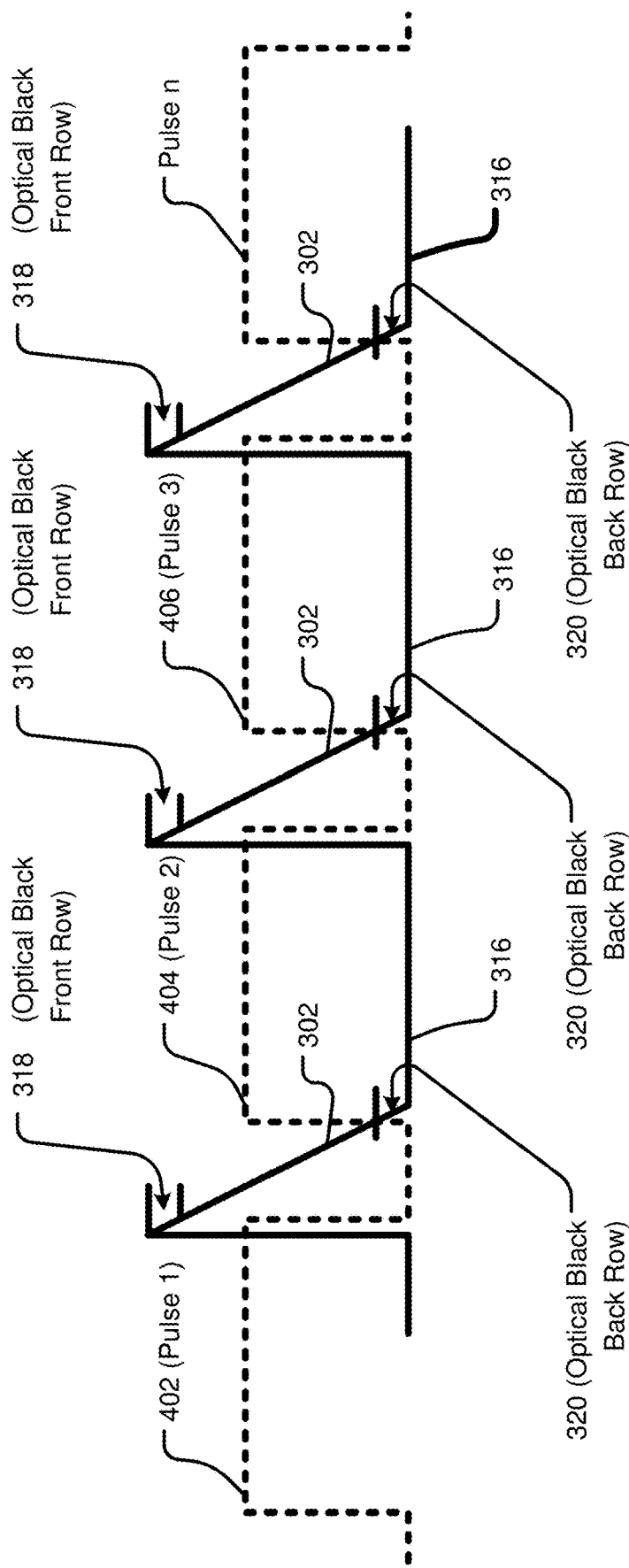
FIG. 5 is a graphical representation of an embodiment of the disclosure combining the operational cycles of a sensor, the electromagnetic emitter, and the emitted electromagnetic pulses of FIGS. 3A-4B, which demonstrate the imaging system during operation.

FIG. 5 is a graphical representation of an embodiment of the disclosure combining the operational cycles, the electromagnetic emitter, and the emitted electromagnetic pulses of FIGS. 3A-3D and 4A to demonstrate the imaging system during operation in accordance with the principles and teachings of the disclosure. As can be seen in the figure, the electromagnetic emitter pulses the emissions primarily during the blanking period 316 of the image sensor such that the pixels will be charged and ready to read during the readout period 302 of the image sensor cycle. The dashed lines in FIG. 5 represent the pulses of electromagnetic radiation (from FIG. 4A). The pulses of electromagnetic radiation are primarily emitted during the blanking period 316 of the image sensor but may overlap with the readout period 302 of the image sensor.

An exposure frame includes the data read by the pixel array of the image sensor during a readout period 302. The exposure frame may be combined with an indication of what type of pulse was emitted by the emitter prior to the readout period 302. The combination of the exposure frame and the indication of the pulse type may be referred to as a dataset. Multiple exposure frames may be combined to generate a black-and-white or RGB color image. Additionally, hyperspectral, fluorescence, and/or laser mapping imaging data may be overlaid on a black-and-white or RGB image.

In an embodiment, an exposure frame is the data sensed by the pixel array during the readout period 302 that occurs subsequent to a blanking period 316. The emission of electromagnetic radiation is emitted during the blanking period 316. In an embodiment, a portion of the emission of electromagnetic radiation overlaps the readout period 302. The blanking period 316 occurs when optical black pixels of the pixel array are being read and the readout period 302 occurs when active pixels of the pixel array are being read. The blanking period 316 may overlap the readout period 302.

FIGS. 6A and 6B illustrate processes for recording an image frame. Multiple image frames may be strung together to generate a video stream. A single image frame may include data from multiple exposure frames, wherein an exposure frame is the data sensed by a pixel array subsequent to an emission of electromagnetic radiation. FIG. 6A illustrates a traditional process that is typically implemented with a color image sensor having a color filter array (CFA) for filtering out certain wavelengths of light per pixel. FIG. 6B is a process that is disclosed herein and can be implemented with a monochromatic "color agnostic" image sensor that is receptive to all wavelengths of electromagnetic radiation.

The process illustrated in FIG. 6A occurs from time t(0) to time t(1). The process begins with a white light emission 602 and sensing white light 604. The image is processed and displayed at 606 based on the sensing at 604.

The process illustrated in FIG. 6B occurs from time t(0) to time t(1). The process begins with an emission of green light 612 and sensing reflected electromagnetic radiation 614 subsequent to the emission of green light 612. The process continues with an emission of red light 616 and sensing reflected electromagnetic radiation 618 subsequent to the emission of red light 616. The process continues with an emission of blue light 620 and sensing reflected electromagnetic radiation 622 subsequent to the emission of blue light 620. The process continues with one or more emissions of a fluorescence excitation wavelengths 624 and sensing reflected electromagnetic energy 626 subsequent to each of the one or more emissions of fluorescence excitation wavelengths of electromagnetic radiation 624. The image is processed and displayed at 628 based on each of the sensed reflected electromagnetic energy instances 614, 618, 622, and 626.

The process illustrated in FIG. 6B provides a higher resolution image and provides a means for generating an RGB image that further includes fluorescence imaging data. When partitioned spectrums of light are used, (as in FIG. 6B) a sensor can be made sensitive to all wavelengths of electromagnetic energy. In the process illustrated in FIG. 6B, the monochromatic pixel array is instructed that it is sensing electromagnetic energy from a predetermined partition of the full spectrum of electromagnetic energy in each cycle. Therefore, to form an image the sensor need only be cycled with a plurality of differing partitions from within the full spectrum of light. The final image is assembled based on the multiple cycles. Because the image from each color partition frame cycle has a higher resolution (compared with a CFA pixel array), the resultant image created when the partitioned light frames are combined also has a higher resolution. In other words, because each and every pixel within the array (instead of, at most, every second pixel in a sensor with a CFA) is sensing the magnitudes of energy for a given pulse and a given scene, just fractions of time apart, a higher resolution image is created for each scene.

As can be seen graphically in the embodiments illustrated in FIGS. 6A and 6B between times t(0) and t(1), the sensor for the partitioned spectrum system in FIG. 6B has cycled at least four times for every one of the full spectrum system in FIG. 6A. In an embodiment, a display device (LCD panel) operates at 50-60 frames per second. In such an embodiment, the partitioned light system in FIG. 6B may operate at 200-240 frames per second to maintain the continuity and smoothness of the displayed video. In other embodiments, there may be different capture and display frame rates. Furthermore, the average capture rate could be any multiple of the display rate.

In an embodiment, it may be desired that not all partitions be represented equally within the system frame rate. In other words, not all light sources have to be pulsed with the same regularity so as to emphasize and de-emphasize aspects of the recorded scene as desired by the users. It should also be understood that non-visible and visible partitions of the electromagnetic spectrum may be pulsed together within a system with their respective data value being stitched into the video output as desired for display to a user.

An embodiment may comprise a pulse cycle pattern as follows:
  i. Green pulse;
  ii. Red pulse;
  iii. Blue pulse;
  iv. Green pulse;
  v. Red pulse;
  vi. Blue pulse;
  vii. Fluorescence excitation pulse;
  viii. (Repeat)

An embodiment may comprise a pulse cycle pattern as follows:
  i. Luminance pulse;
  ii. Red chrominance pulse;
  iii. Luminance pulse;
  iv. Blue Chrominance pulse;
  v. Fluorescence excitation pulse;
  vi. (Repeat)

An embodiment may comprise a pulse cycle pattern as follows:
  i. Luminance pulse;
  ii. Red chrominance pulse;
  iii. Luminance pulse;
  iv. Blue Chrominance pulse;
  v. Luminance pulse;
  vi. Red chrominance pulse;
  vii. Luminance pulse;
  viii. Blue Chrominance pulse;
  ix. Fluorescence excitation pulse;
  x. (Repeat)

As can be seen in the example, a fluorescence excitation partition may be pulsed at a rate differing from the rates of the other partition pulses. This may be done to emphasize a certain aspect of the scene, with the fluorescence imaging data simply being overlaid with the other data in the video output to make the desired emphasis. It should be noted that the addition of a fluorescence partition on top of the RED, GREEN, and BLUE partitions does not necessarily require the serialized system to operate at four times the rate of a full spectrum non-serial system because every partition does not have to be represented equally in the pulse pattern. As seen in the embodiment, the addition of a partition pulse that is represented less in a pulse pattern (fluorescence excitation in the above example), would result in an increase of less than 20% of the cycling speed of the sensor to accommodate the irregular partition sampling.

In various embodiments, the pulse cycle pattern may further include any of the following wavelengths in any suitable order. Such wavelengths may be particularly suited for exciting a fluorescent reagent to generate fluorescence imaging data by sensing the relaxation emission of the fluorescent reagent based on a fluorescent reagent relaxation emission:
  i. 770±20 nm;
  ii. 770±10 nm;

iii. 770±5 nm;
iv. 790±20 nm;
v. 790±10 nm;
vi. 790±5 nm;
vii. 795±20 nm;
viii. 795±10 nm;
ix. 795±5 nm;
x. 815±20 nm;
xi. 815±10 nm;
xii. 815±5 nm;
xiii. 770 nm to 790 nm; and/or
xiv. 795 nm to 815 nm.

The partition cycles may be divided so as to accommodate or approximate various imaging and video standards. In an embodiment, the partition cycles comprise pulses of electromagnetic energy in the Red, Green, and Blue spectrum as follows as illustrated best in FIGS. 7A-7D. The timing relationship between the emission of pulses of electromagnetic radiation by the emitter, and the readout of the pixel array is further illustrated in FIGS. 7A-7D.

In an embodiment, the emitter emits one or more hyperspectral emissions for eliciting a spectral response. The hyperspectral emissions include one or more of electromagnetic radiation having a wavelength from about 513-545 nm, from about 565-585 nm, and/or from about 900-1000 nm. In such an embodiment, the coherent light source 802 includes at least one laser emitter for the 513-545 nm partition, at least one laser emitter for the 565-585 partition, and at least one laser emitter for the 900-1000 nm partition. It should be appreciated that additional hyperspectral emissions for eliciting a spectral response can be emitted without departing from the scope of the disclosure.

In an embodiment, the emitter emits one or more fluorescence excitation emissions for fluorescing a reagent. The fluorescence excitation emissions include one or more of electromagnetic radiation having a wavelength from about 460-470 nm, 529-537 nm. 633-643 nm, 775-785 nm, 800-810 nm, 970-980 nm, 575-579 nm, 519-527 nm, 770-790 nm, and/or 795-815 nm. In such an embodiment, the coherent light source 802 may include at least one laser emitter for each of the aforementioned partitions of electromagnetic radiation. It should be appreciated that additional fluorescence excitation emissions for fluorescing a reagent can be emitted without departing from the scope of the disclosure.

Figure 7A:
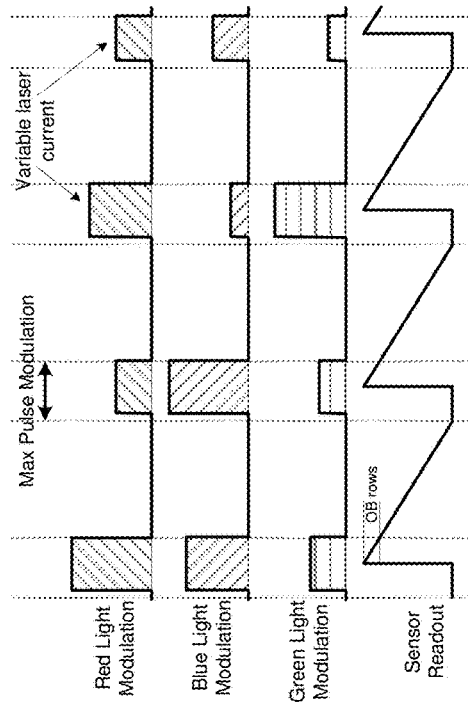
FIGS. 7A-7E illustrate schematic views of the processes over an interval of time for recording a frame of video for both full spectrum light and partitioned spectrum light.

In FIG. 7A, the different light intensities have been achieved by modulating the light pulse width or duration within the working range shown by the vertical grey dashed lines. FIG. 7A illustrates the general timing relationships within a four-frame cycle, between pulsed mixtures of three wavelengths and the readout cycle of the pixel array of the image sensor. In an embodiment, there are three monochromatic pulsed light sources under the control of the controller. Periodic sequences of monochromatic red, monochromatic green, and monochromatic blue exposure frames are captured, e.g. with an R-G-B-G pulsing pattern and assembled into an sRGB image frame by the image signal processor chain.

Figure 7C:
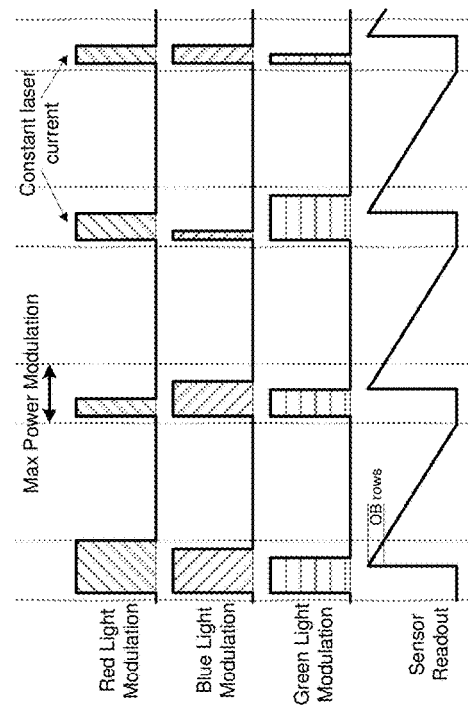
Figure 7B:
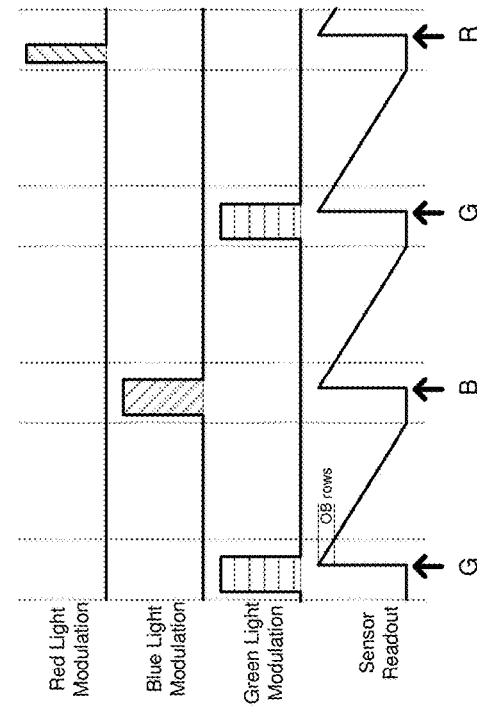

In FIG. 7B, the different light intensities have been achieved by modulating the light power or the power of the electromagnetic emitter, which may be a laser or LED emitter, but keeping the pulse width or duration constant.

FIG. 7C shows the case where both the light power and the light pulse width are being modulated, leading to greater flexibility. The partition cycles may use Cyan Magenta Yellow (CMY), infrared, ultraviolet, hyperspectral, and fluorescence using a non-visible pulse source mixed with visible pulse sources and any other color space required to produce an image or approximate a desired video standard that is currently known or yet to be developed. It should also be understood that a system may be able to switch between the color spaces on the fly to provide the desired image output quality.

Figure 7D:
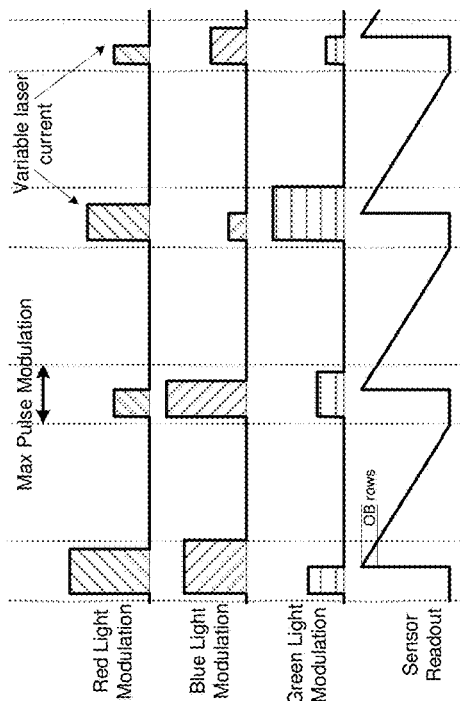

In an embodiment using color spaces Green-Blue-Green-Red (as seen in FIG. 7D) it may be desirous to pulse the luminance components more often than the chrominance components because users are generally more sensitive to light magnitude differences than to light color differences. This principle can be exploited using a monochromatic image sensor as illustrated in FIG. 7D. In FIG. 7D, green, which contains the most luminance information, may be pulsed more often or with more intensity in a (G-B-G-R-G-B-G-R . . . ) scheme to obtain the luminance data. Such a configuration would create a video stream that has perceptively more detail, without creating and transmitting unperceivable data.

In an embodiment, all three sources of light are pulsed in unison with light energies that are modulated to provide pure luminance information in the same exposure frame. The light energies may be modulated according to color transformation coefficients that convert from RGB color space to YCbCr color space. It should be appreciated that the color transformation may be implemented according to any suitable standard such as the ITU-R BT.709 HD standard, the ITU-R BT.601 standard, the ITU-R BT.2020 standard, or any other suitable standard or formula. The conversion may be performed according to the ITU-R BT.709 HD standard as follows:

$$\begin{bmatrix} Y \\ Cb \\ Cr \end{bmatrix} = \begin{bmatrix} R \\ G \\ B \end{bmatrix} \begin{bmatrix} 0.183 & 0.614 & 0.062 \\ -0.101 & -0.339 & 0.439 \\ 0.439 & -0.399 & -0.040 \end{bmatrix}$$

In addition to the modulation of luminance information, a full color image further requires the red chrominance and blue chrominance components. However, the algorithm applied for the luminance component cannot be directly applied for chrominance competence because the algorithm is signed as reflected in the fact that some of the RGB coefficients are negative. In an embodiment, a degree of luminance is added so that all of the final pulse energies are a positive value. As long as the color fusion process in the image signal processor is aware of the composition of the chrominance exposure frames, they can be decoded by subtracting the appropriate amount of luminance from a neighboring frame. The pulse energy proportions are given by:

$$Y = 0.183 \cdot R + 0.614 \cdot G + 0.062 \cdot B$$
$$Cb = \lambda \cdot Y - 0.101 \cdot R - 0.339 \cdot G + 0.439 \cdot B$$
$$Cr = \delta \cdot Y + 0.439 \cdot R - 0.399 \cdot G - 0.040 \cdot B$$

where $$\lambda \geq \frac{0.339}{0.614} = 0.552$$
$$\delta \geq \frac{0.399}{0.614} = 0.650$$

If the λ factor is equal to 0.552, the red and green components are cancelled. In the case, the blue chrominance information can be provided with pure blue light. Similarly, if the δ factor is equal to 0.650, the blue and green components are cancelled, and the red chrominance information can be provided with pure red light. This embodiment is a convenient approximation for digital frame reconstruction.

In an embodiment where white balance is performed in the illumination domain, then the modulation is imposed in addition to the white balance modulation.

Figure 7E:
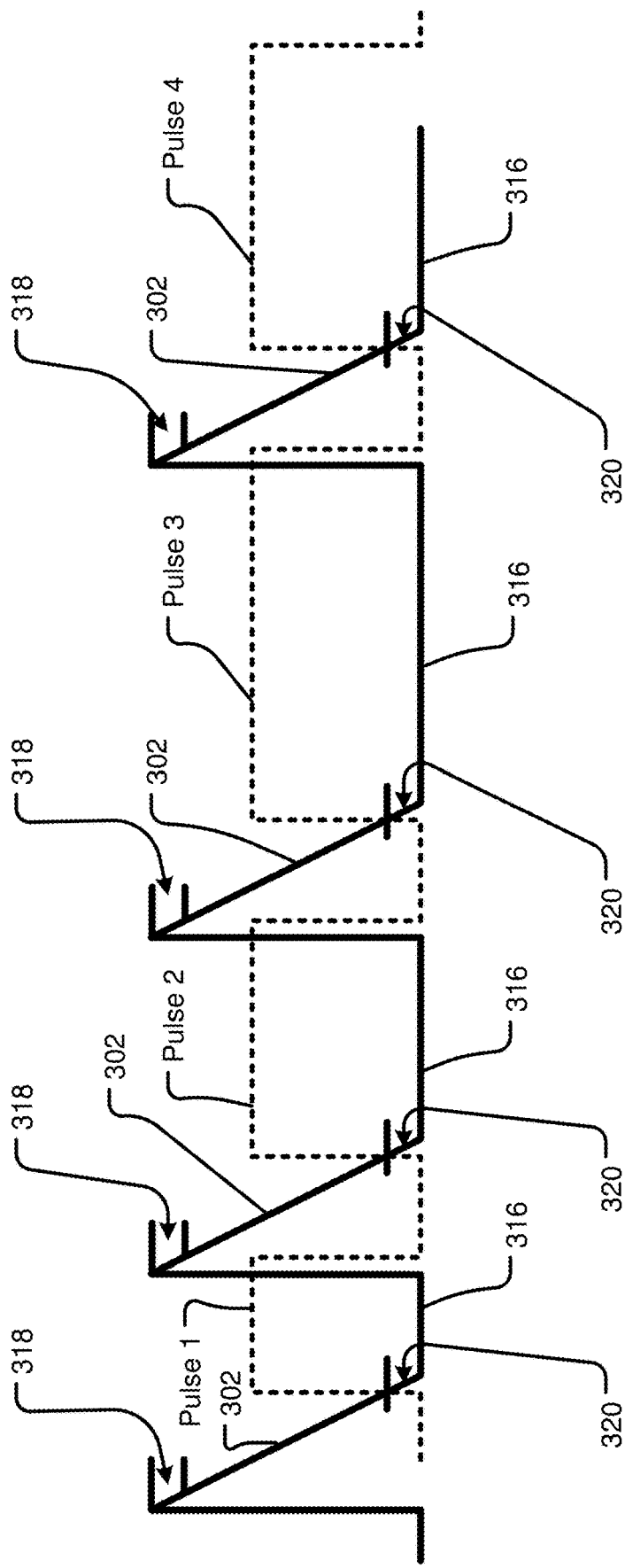

In an embodiment, duplicating the pulse of a weaker partition may be used to produce an output that has been adjusted for the weaker pulse. For example, blue laser light is considered weak relative to the sensitivity of silicon-based pixels and is difficult to produce in comparison to the red or green light, and therefore may be pulsed more often during a frame cycle to compensate for the weakness of the light. These additional pulses may be done serially over time or by using multiple lasers that simultaneously pulse to produce the desired compensation effect. It should be noted that by pulsing during a blanking period (time during which the sensor is not reading out the pixel array), the sensor is insensitive to differences/mismatches between lasers of the same kind and simply accumulates the light for the desired output. In another embodiment, the maximum light pulse range may be different from frame to frame. This is shown in FIG. 7E, where the light pulses are different from frame to frame. The sensor may be built to be able to program different blanking periods with a repeating pattern of two or three or four or n frames.

In FIG. 7E, four different light pulses are illustrated, and Pulse 1 may repeat for example after Pulse 4 and may have a pattern of four frames with different blanking periods. This technique can be used to place the most powerful partition on the smallest blanking period and therefore allow the weakest partition to have wider pulse on one of the next frames without the need of increasing the readout speed. The reconstructed frame can still have a regular pattern from frame to frame as it is constituted of many pulsed frames.

Figure 8:
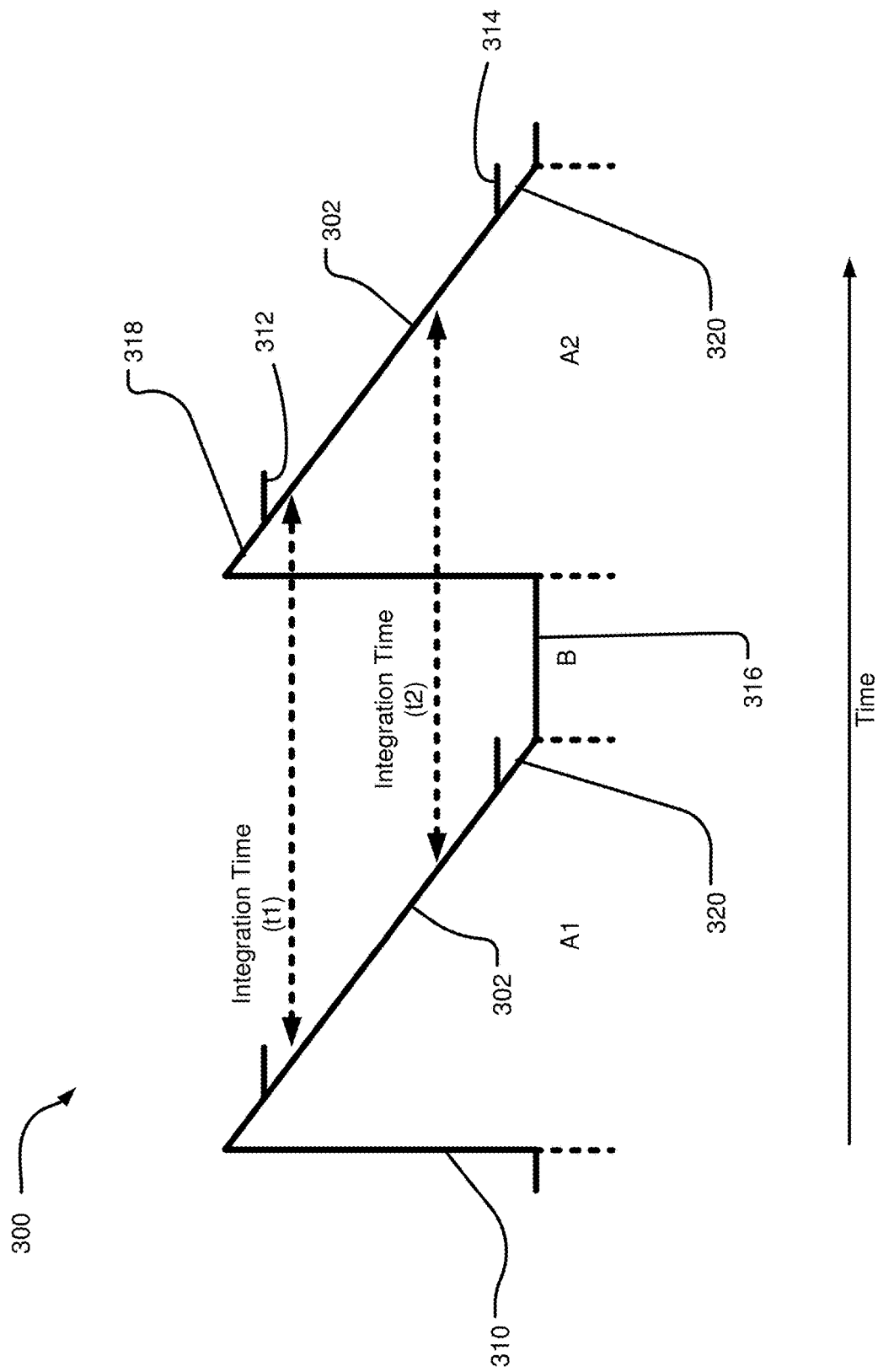
FIG. 8 is a schematic diagram of a readout sequence of an image sensor where an electronic shutter is switched off and light is integrated from readout period to readout period.

FIG. 8 is a schematic diagram of a sensor readout 300 sequence for a full frame integration operation. In an embodiment, the full frame integration is implemented when an electronic shutter is switched off. This might occur when there is no extra reset pointer within the frame. In the full frame integration, the emitted electromagnetic radiation is integrated from readout to readout as shown in FIG. 8. The sensor readout 300 is partitioned into two readout periods 302 notated A1 and A2, and one blanking period 316, notated B. In such an embodiment, a single exposure frame may be generated based on the data captured during each of the readout periods A1 and A2. In some instances, the readout periods A1 and A2 are too short in duration to read the data captured by each pixel in the pixel array. In such an instance, the readout periods A1 and A2 return data from only a portion of the pixel array, and therefore the data from the readout periods A1 and A2 must be combined to generate a single, complete exposure frame.

In an embodiment, the pixels of the pixel array are read out during the readout period 302 represented by time A1 and A2 and pixels are not read out during the blanking period 316 represented by time B. In such an embodiment, pixels in the pixel array of the image sensor are always collecting electromagnetic radiation. The integration times t1 and t2 represent the light collection periods for two different pixels of the pixel array. The integration time t1 represents the time period for collecting electromagnetic radiation for a first illustrative pixel, and the integration time t2 represents the time period for collecting electromagnetic radiation for a second illustrative pixel. As shown, a pixel collects light information from a certain timestamp within a readout period A1 until that same timestamp within a subsequent readout period A2.

In an embodiment, the light levels change over the course of the readout period 302. When this occurs, the pixels read during the later portion of the readout period 302 will gather a different amount of electromagnetic radiation than the pixels read earlier in the readout period 302. Because one exposure comprises data gathered by all pixels read over the course of the readout period 302, the exposure frame is then skewed by the changing light levels.

Figure 9:
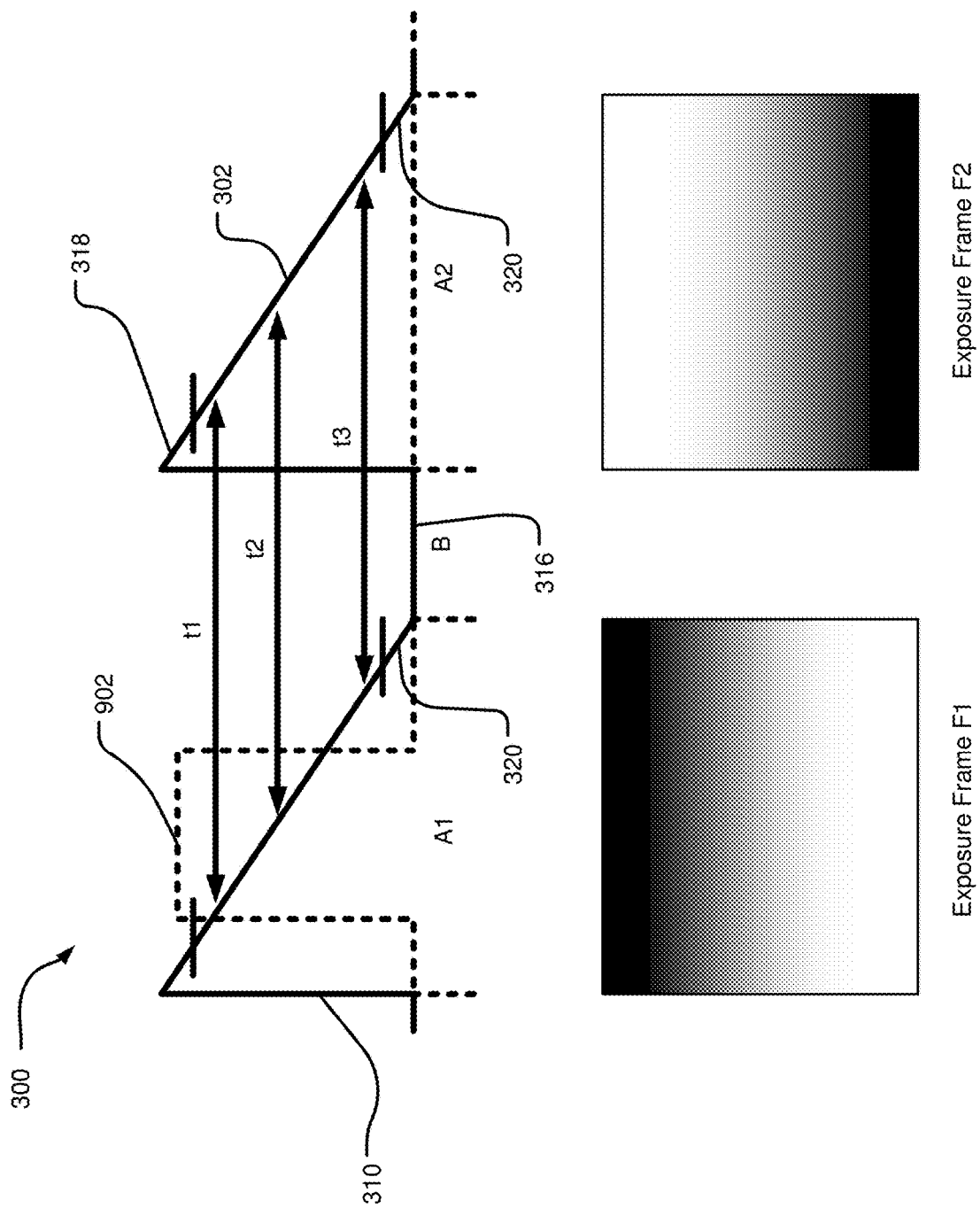
FIG. 9 is a schematic diagram of a readout sequence of an image sensor timed with a pulse of electromagnetic radiation occurring during a readout period of the image sensor, wherein the pixel array of the image sensor continuously gathers light information to generate a first exposure frame during the first readout period and a second exposure frame during the second readout period.

FIG. 9 is a schematic diagram of a readout sequence 300 for a pixel array in which a pulse 902 of electromagnetic radiation occurs during the readout period A1. The embodiment illustrated in FIG. 9 might be a common occurrence in a videostroboscopy implementation, where the frequency of the pulses of electromagnetic radiation are timed to mimic the frequency of the vibrations of the patient's vocal cords. This may cause the pulses of electromagnetic radiation to be emitted at a higher frequency than the cycling of the image sensor (from readout period 302 to blanking period 316). When this occurs, one or more pulses of electromagnetic radiation may occur during a readout period 302 rather than only during a blanking period 316.

In the embodiment, the blanking period 316 between readout periods A1, A2 is represented by blanking period B. The boxes labeled F1 and F2 represent exposure frames generated by the pixel array in response to the pulse 902 of electromagnetic radiation and the two readout periods A1, A2 illustrated in the readout sequence 300. Intuitively, one would expect to see a lighter colored bar in the exposure frame F1 related to readout period A1 and expect exposure frame F2 to contain no light information at all. Instead, because the pixels are continually capturing light information, exposure frame F1 is black until the pulse 902 of electromagnetic radiation begins. As the pulse 902 persists in the exposure frame, there is a gradient of light collected between A1.t1 and A1.t2. This gradient continues until the pulse 902 finishes, after which every pixel read out contains the same amount of light in formation. At A2.t1, the pixels have collected part of the pulse information from the previous exposure frame F1 and so a second gradient is seen in the exposure frame F2. This phenomenon creates flickering or rolling noise on the video stream. This occurs when the image sensor is exposed to pulsing or strobing light.

In an embodiment, the pulses 902 of electromagnetic radiation occur during the blanking period 316 to mitigate the flickering or rolling noise on the video stream. In one implementation of the disclosure, the readout period 302 is suspended when the emitter is emitting a pulse 902 of electromagnetic radiation. In one implementation of the disclosure, the light deficit or light excess of each line is mapped and a specific digital gain per row of pixels is applied.

The typical range for light strobing is 60 Hz to 1000 Hz, and in an embodiment, the pulses of electromagnetic radiation emitted by the emitter are emitted within that frequency range. However, it should be appreciated that any other frequency outside this range falls within the scope of the disclosure.

Figure 10:
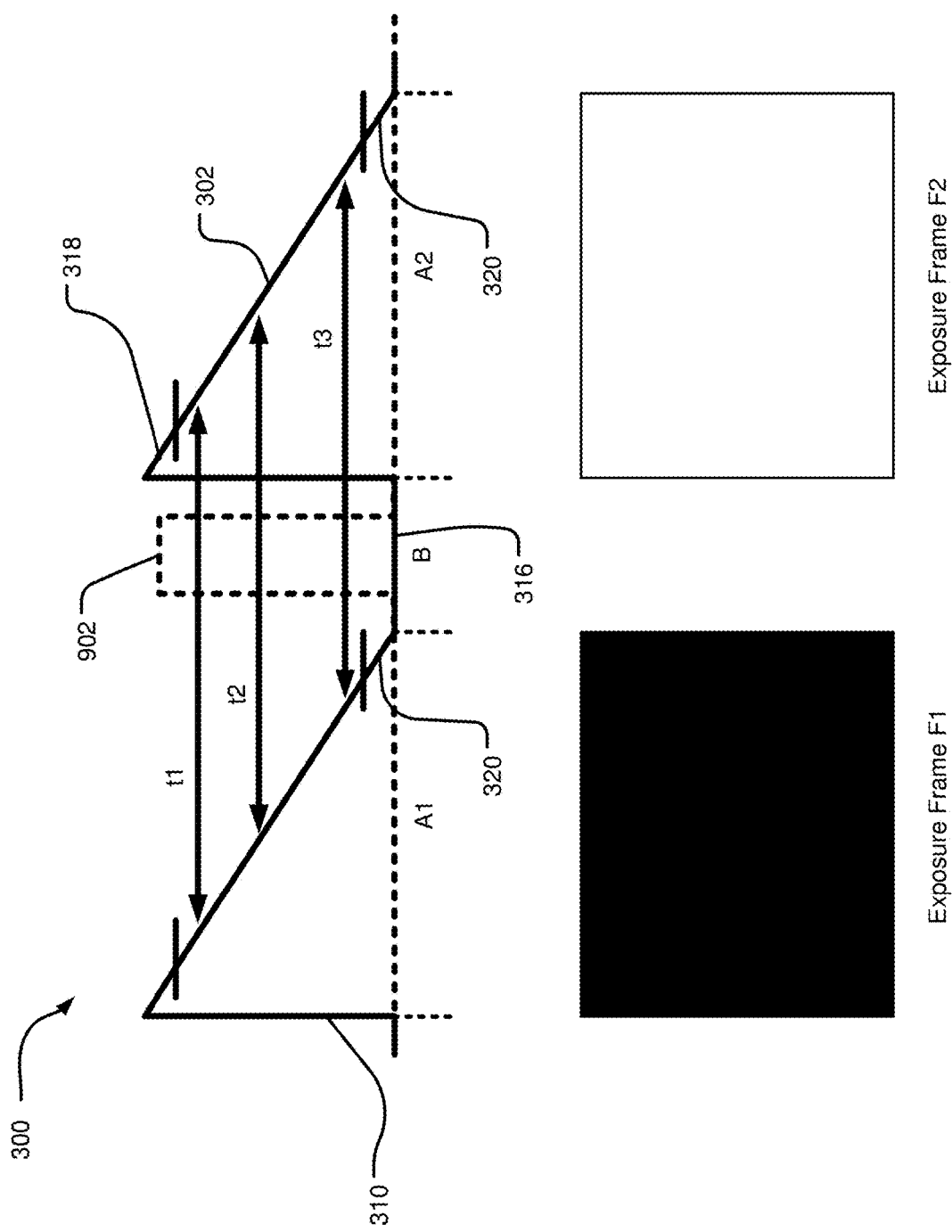
FIG. 10 is a schematic diagram of a readout sequence of an image sensor timed with a pulse of electromagnetic radiation occurring during a blanking period of the image sensor, wherein a first exposure frame captured during the first readout period is black because the pixel array collected no light information, and a second exposure frame captured during a second readout period is fully exposed by the same amount of light.

FIG. 10 is a schematic diagram of a readout sequence 300 for a pixel array in an embodiment where electromagnetic radiation is pulsed during the blanking period 316. The embodiment illustrated in FIG. 10 might be a common occurrence in a videostroboscopy implementation, where the frequency of the pulses of electromagnetic radiation are timed to mimic the frequency of the vibrations of the patient's vocal cords. In such an embodiment, the exposure frame F1 captured during the readout period A1 is completely black because no light information is collected by the pixel array during the readout period A1. The exposure frame F2 indicates that all pixels are exposed by the same amount of electromagnetic radiation. As illustrated, B.t1, B.t2 and B.t3 have all been exposed to the same amount of electromagnetic radiation, and this results in the exposure frame F2.

Figure 11A:
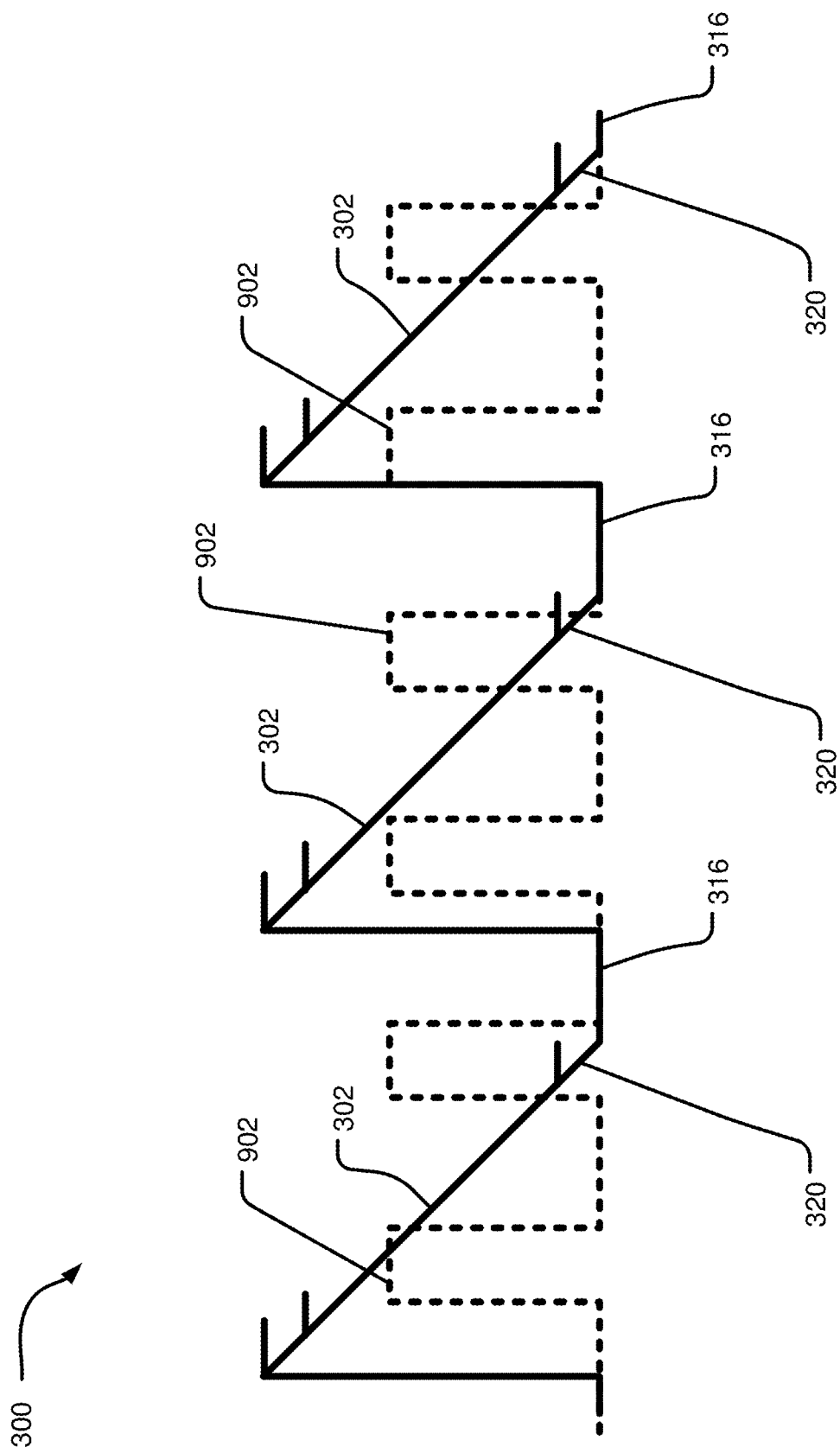
FIG. 11A is a schematic diagram of a readout sequence of an image sensor timed with regular pulses of electromagnetic radiation, wherein the pulses may be timed according to the frequency of a patient's vocal cord vibrations for videostroboscopy, and wherein the pulses occur during readout periods and blanking periods of the image sensor.
Figure 11B:
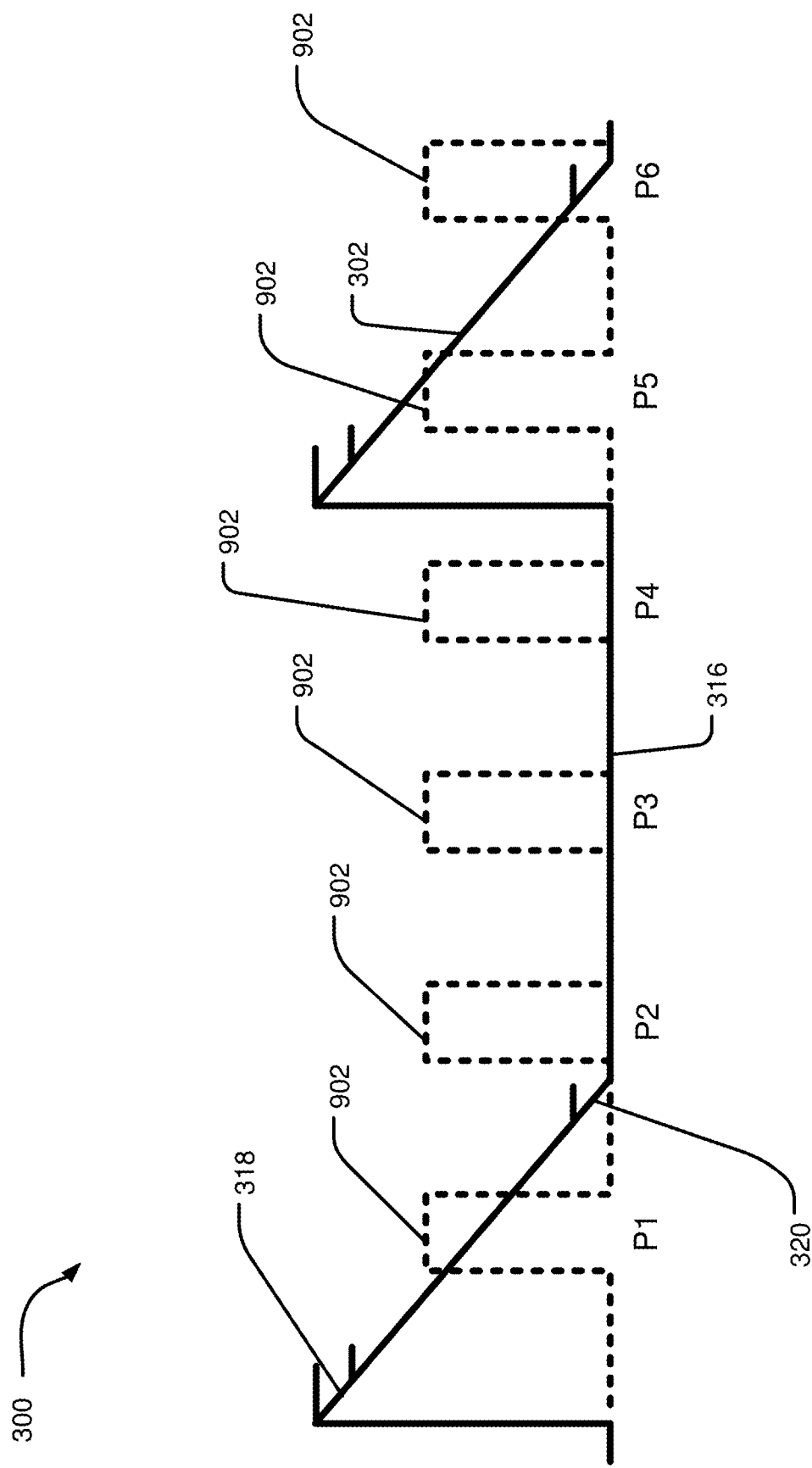
FIG. 11B is a schematic diagram of a readout sequence of an image sensor timed with regular pulses of electromagnetic radiation, wherein the duration of the blanking period of the image sensor is lengthened relative to the duration of the readout period.
Figure 11C:
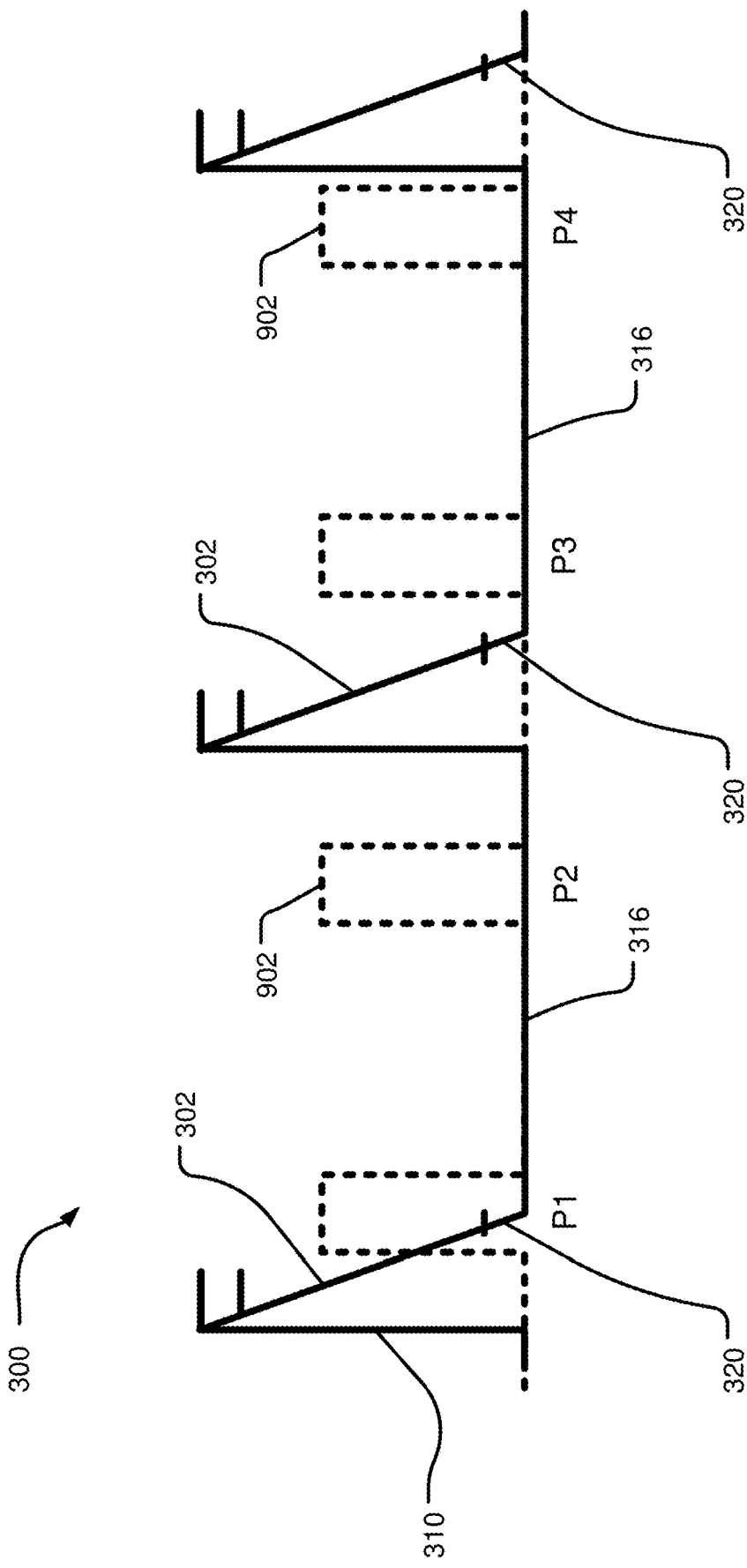
FIG. 11C is a schematic diagram of a readout sequence of an image sensor timed with regular pulses of electromagnetic radiation, wherein one or more of the pulses and resultant exposure frames may be suppressed to reducing flickering or rolling noise in a resultant video stream.

FIGS. 11A-11C are schematic diagrams of implementations of a readout sequence 300 of a pixel array (illustrated by the bold line) timed with pulses of electromagnetic radiation emitted by an emitter (illustrated by the dotted line). In the embodiments, the pulses of electromagnetic radiation are emitted at a regular frequency, and the frequency may be determined based on the vibration frequency of a patient's vocal cords for purposes of videostroboscopy. When the frequency of the pulses of electromagnetic radiation are constrained by the frequency of the vibrations of the patient's vocal cords, the controller cannot ensure that pulses are only emitted during the blanking period of the image sensor. When a pulse of electromagnetic radiation is emitted during the readout period of the image sensor, the resultant video stream may have flickering or noise that is undesirable to an end user. In the embodiments illustrated in FIGS. 11A-11C, one or more pulses of electromagnetic radiation may need to be suppressed from the final video stream to avoid flickering or noise in the resultant video stream.

FIG. 11A illustrates an implementation wherein pulses 902 of electromagnetic radiation are emitted in regular succession at a certain frequency. In this implementation, some pulses are emitted during the readout periods 302, the blanking periods 316, and/or straddle a readout period 302 and a blanking period 316. Most sensor communication sequences have long readout periods 302 and short blanking periods 316. When a pulse of electromagnetic radiation is emitted during a readout period, and if the data from that readout period is not suppressed in the final video stream, then the final video stream will exhibit flickering or noise that is undesirable to an end user. FIG. 11A represents the complications associated with using a pulsed endoscopic imaging system (as described herein) for videostroboscopy purposes.

FIG. 11B illustrates an embodiment in which the pulses 902 of electromagnetic radiation are emitted in regular succession and the duration of the blanking period 316 is extended relative to the duration of the readout period 302. In some embodiments wherein the duration of the blanking period 316 is extended, the duration of the readout periods 302 must be proportionally shortened. When the duration of the readout period 302 is shortened, the pixel array must be read at a higher data rate and/or the number of pixels read by the pixel array (or present in the pixel array) must be reduced.

In the embodiment illustrated in FIG. 11B, the pulses P1, P5, and P6 must be suppressed to prevent flickering or rolling noise in the resultant video stream. In an embodiment, the optical block front 318 and optical black back 320 rows are considered a portion of the blanking period 316 because optical black pixels will not integrate light. Therefore, a pulse 902 beginning immediately after the beginning of an optical black row 320 readout or ending immediately before the end of an optical black front 318 row readout can be considered a good pulse 902 and does not need to be rejected. After suppression of pulses P1, P5, and P6 that occur during a readout period 302 of the pixel array, the next step is to ensure the same number of pulses 902 are captured during each blanking period 316 and then one pulse during a subsequent blanking period 316. In such an embodiment, the exposure frame may still flicker because successive exposure frames have differing light levels due to a different number of pulses received during each blanking period 316.

FIG. 11C illustrates an embodiment in which the pulses 902 of electromagnetic radiation are suppressed such that electromagnetic radiation is not emitted during a readout period 302 of the pixel array. The pulses P2, P3, and P4 are not suppressed because those pulses occur during a blanking period 316 of the pixel array. However, the first blanking period 316 includes pulse P2 and the second blanking period 316 includes two pulses P3 and P4. One of the pulses P3 or P4 must also be suppressed to maintain consistent light exposure. In some embodiments, a pulse 902 straddles a readout period 302 and a blanking period 316. This is illustrated in FIG. 11C with pulse P1. The straddling pulse P1 may also be suppressed and the next full pulse P2 may be used instead.

In an embodiment, the decision process to determine when to allow or suppress a pulse 902 in the final exposure frames selected for the video stream can be executed by selecting pulse duty cycles based on pulse frequency and blanking period duration. This ensures consistent levels of electromagnetic radiation reach the image sensor. For example, if the pulse train frequency is 150 Hz and the duty cycle is 10%, then the electromagnetic radiation may be strobed for 0.6 ms per pulse. In a further example, if the frequency is adjusted to 500 Hz, then the duty cycle may be selected based on the maximum and minimum number of pulses of electromagnetic radiation that could occur during a blanking period 316 while ensuring the image sensor is still pulsed for 0.6 ms. In such an example, the exposure time may be spread over multiple pulses of electromagnetic radiation.

In some embodiments, it is difficult to significantly extend the blanking period 316 because this decreases the frame rate if the same number of pixels are ready during the readout period 302. A decreased frame rate increases the number of superimposed exposure frames available during videostroboscopy, and this can blur the resultant video stream. In turn, reducing the duration of the readout period 302 may be accomplished by reducing the image resolution by readout out fewer pixel. This may have a negative impact on the quality of the final image frames. Accordingly, if too many pulses are rejected, each image frame will not appear as crisp because of lower occurrence at the sensor frame rate. This may lead for low frequency flickering if the pulse rejection reaches a certain threshold.

Figure 12A:
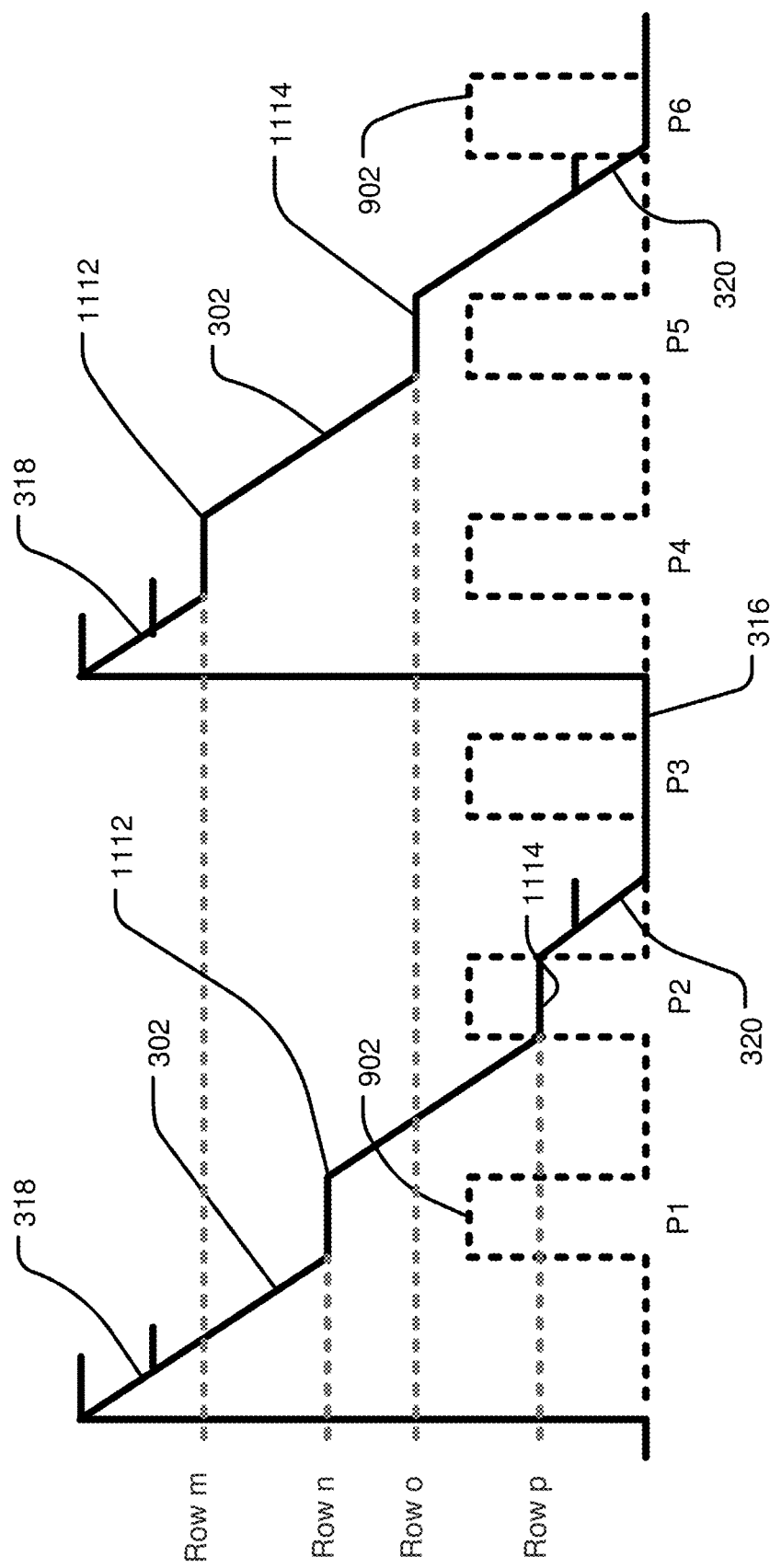
FIG. 12A is a schematic diagram of a readout sequence of an image sensor timed with regular pulses of electromagnetic radiation, wherein readout periods of the image sensor are suspended when a pulse of electromagnetic radiation is emitted during the readout period.
Figure 12B:
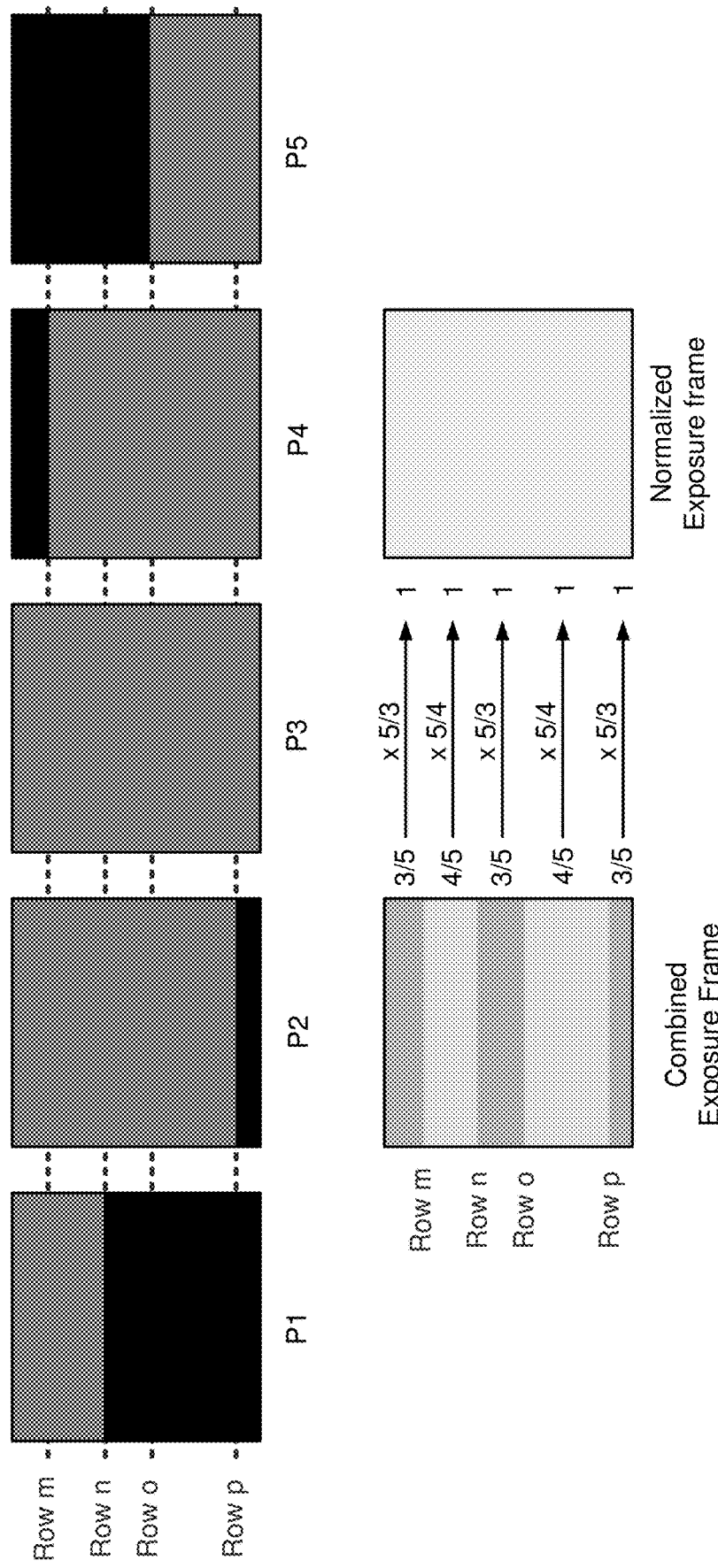
FIG. 12B illustrates multiple partial exposure frame contributions captured by the image sensor in response to each pulse of electromagnetic radiation, and the resultant combined exposure frame generated in response to the pulses P1, P2, P3, P4, and P5 of electromagnetic radiation as illustrated in FIG. 12A.

FIG. 12A is a schematic diagram of a readout sequence of a pixel array timed with a pulsing sequence of an emitter. FIG. 12B illustrates the resultant exposure frame F2 generated by the readout sequence and pulsing sequence illustrated in FIG. 12A. The embodiment illustrated in FIGS. 12A-12B is timed such that no pulses of electromagnetic radiation need to be rejected during sensor readout 302. This maintains image crispness, image resolution, and the frame rate. The readout period 302 is suspended during a pulse of electromagnetic radiation (see P1 and P4). The sensor readout 302 may be suspended by freezing the sensor clock, freezing the sensor vertical decoder, and/or freezing the horizontal readout of the pixel array. It should be noted that there are multiple other methods to freeze the sensor readout and all such methods fall within the scope of this disclosure.

FIGS. 12A and 12B illustrate the contributions of each light pulse P1, P2, P3, P4, and P5 on the exposure frame F2. The pulses occurring during the exposure frame F1 generate a lit top exposure and a black bottom exposure on the exposure frame F2. In contrast, pulses 902 occurring during the exposure frame F2 generate a black top exposure and a lit bottom exposure on the exposure frame F2. As demonstrated in FIG. 10, a pulse 902 during the blanking period 316 results in a fully lit exposure on the subsequent exposure frame. Because the readout 302 may be suspended during strobing, there is no gradient of light in the exposure frame relative to one pulse and a clear cut is seen at the physical row being readout right before the light pulse 902 starts. For example, the exposure frame from the pulse P1 sees the illumination relative to pulse P1 from the top of the image until Row n. Thereafter, the image is black. The resultant image is the superimposition of all images relative to the relevant pulses 902 (P1 through P5 in the example).

FIG. 12B illustrates the processed combined exposure frame composed by the five exposure frames relative to pulses P1, P2, P3, P4, and P5. There are five distinct stripes that correspond to areas between rows m, n, o and p, which have been exposed to different number of light strobes or pulses 902. For example, during the pulses P1 thru P5, the stripe of rows between row m and row n has been exposed four times out of the five possible exposures. The stripe of rows between row n and row o has been exposed three times out of the five possible exposures. The normalized exposure frame represents the result of processing the image frame to be substantially artifact free. In an embodiment, the combined exposure frame is processed by normalization using digital gain. In the example illustrated in FIG. 12B, for example, a digital gain of 5/3 is applied to the stripe between the top of the pixel array and row m, the stripe between row n and row o, and the stripe between row p and the bottom of the pixel array. A digital gain of 5/4 is applied to the stripe between row m and row n and the stripe between row o and row p.

In an embodiment, the rows of the pixel array that have integrated light originating from a certain pulse of electromagnetic radiation are read out and tracked. Upon readout of the exposure frame, digital gain is applied to different row sections within the exposure frame to normalize the exposure. This compensates for areas of light deficiency of areas with excess light with respect to a computed reference level. Because of the slow motion used in videostroboscopy, this embodiment eliminates motion artifacts in the resultant video stream.

Figure 13A:
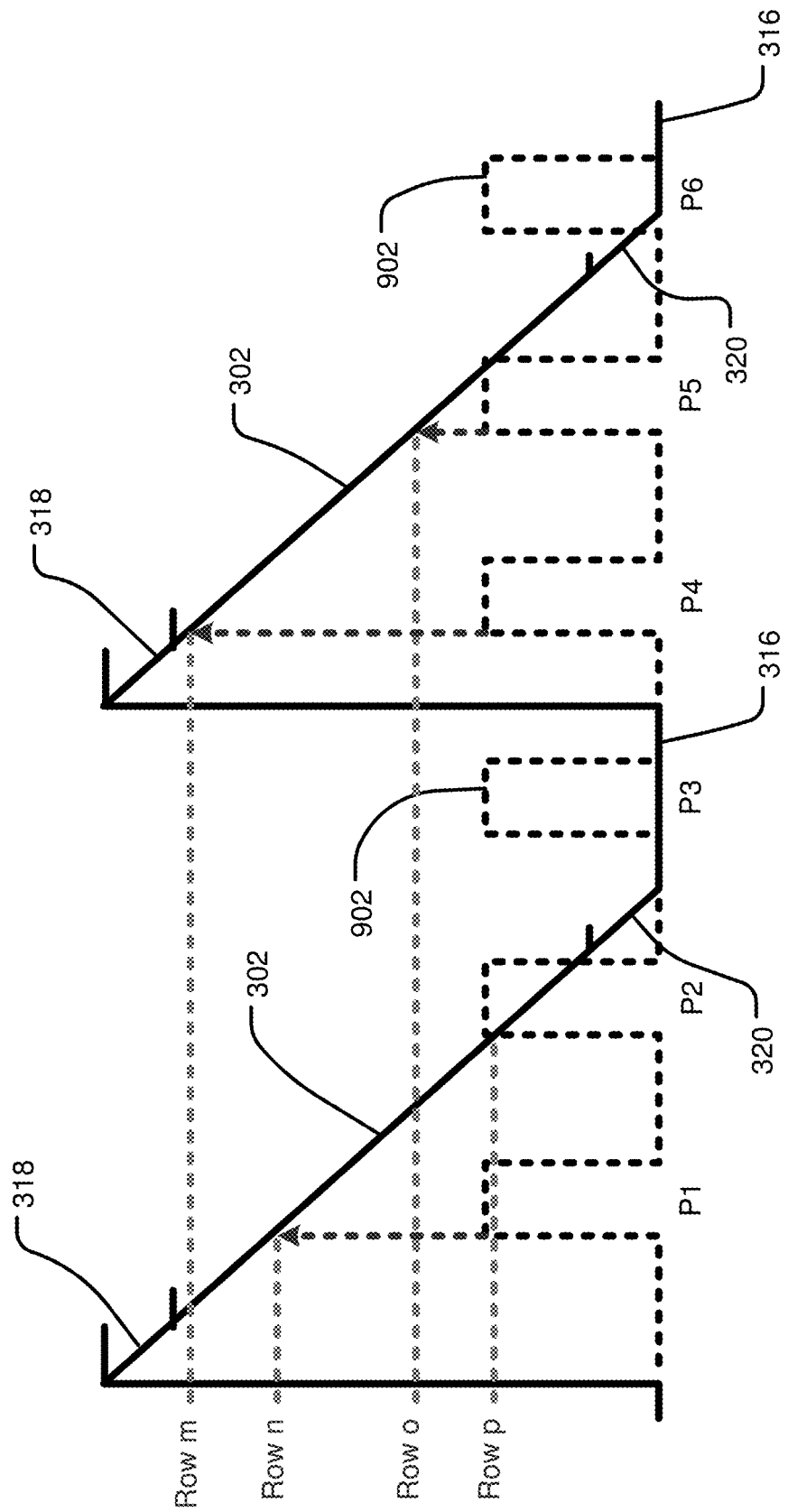
FIG. 13A is a schematic diagram of a readout sequence of an image sensor timed with pulses of electromagnetic radiation occurring during the readout periods and the blanking periods of the image sensor.
Figure 13B:
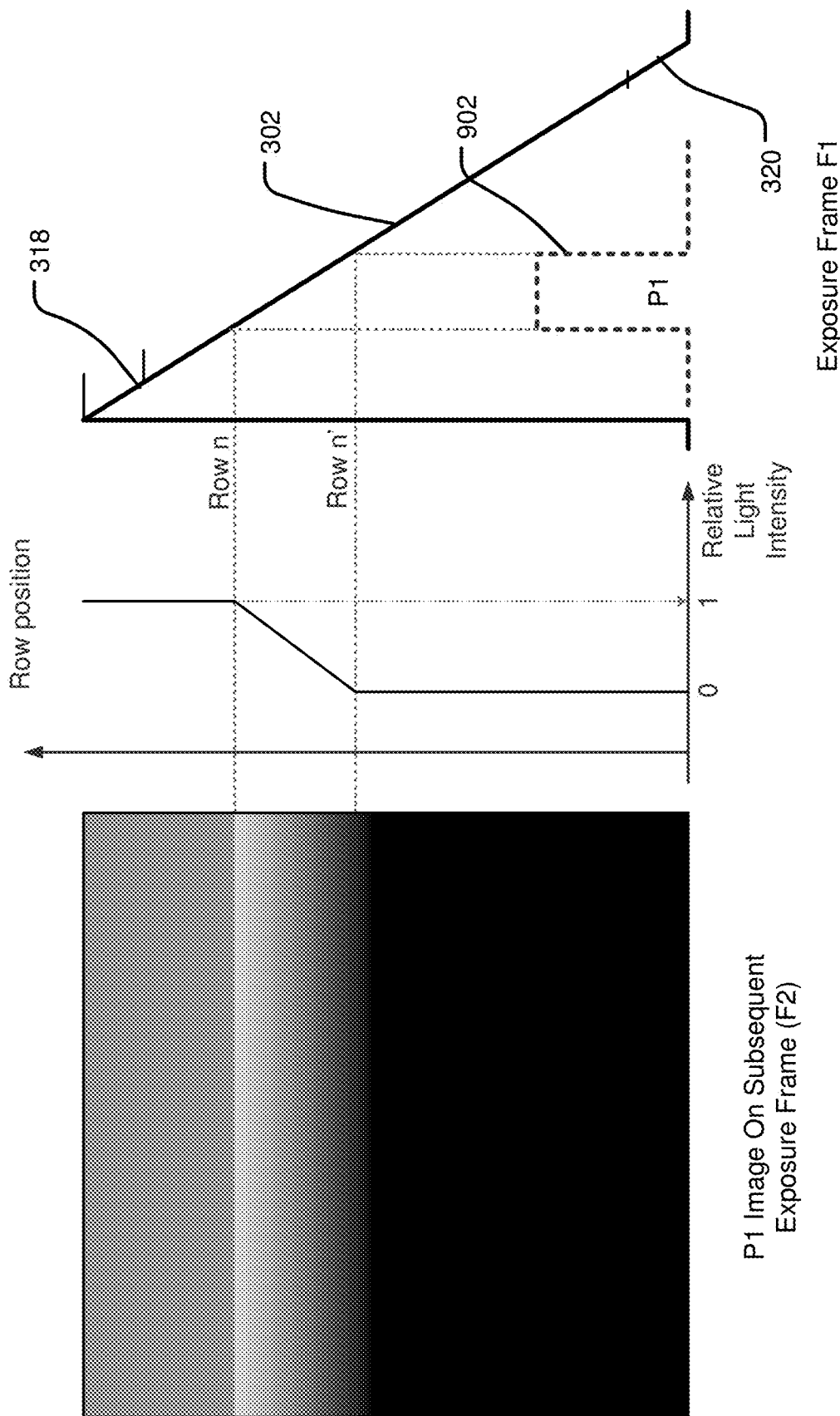
FIG. 13B illustrates an example of a resultant exposure frame captured in response to a single pulse P1 that was emitted during the readout period of the image sensor.
Figure 13C:
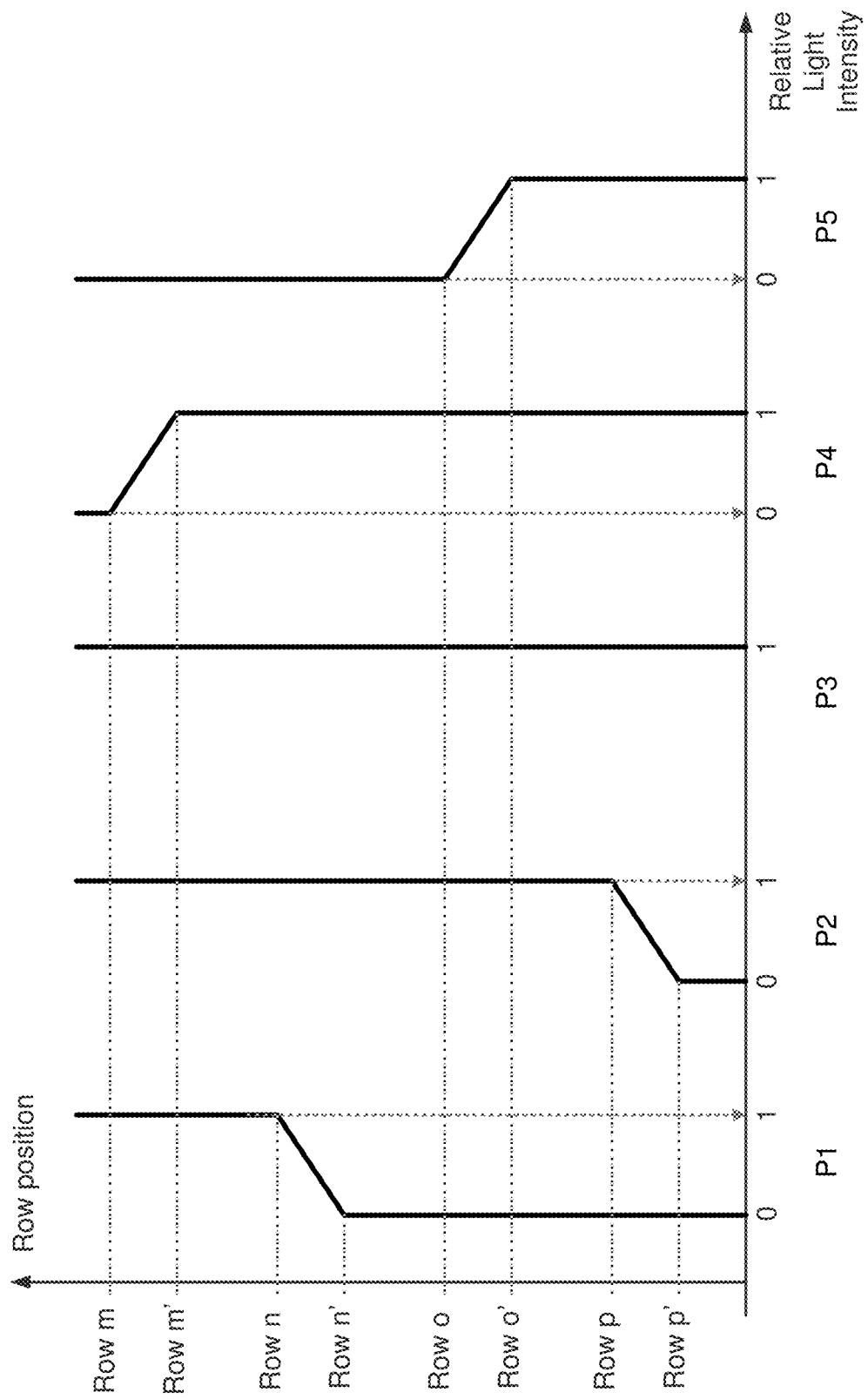
FIG. 13C is a schematic representation of row position versus relative light intensity for each of the pulses of electromagnetic radiation P1, P2, P3, P4, and P5 illustrated in FIG. 13A.

FIGS. 13A-13C illustrate an embodiment of a readout sequence of an image sensor matched with a pulsing sequence of an emitter, along with the resultant exposure frames and combined exposure frame. The pulsing sequence may be emitted in consistent intervals determined based on the vocal cord frequency of a patient being examined with videostroboscopy.

FIG. 13A is a schematic diagram of a sensor readout sequence timed against pulses P1, P2, P3, P4, P5, and P6. In the embodiment, pulses P1, P2, P4, and P6 occur largely or entirely during a readout period 302. Specifically, pulses P1 and P2 occur largely or entirely during the readout period 302 for exposure frame F1. Pulses P4 and P5 occur entirely during the readout period 302 for exposure frame F2. Pulses P3 and P6 occur during a blanking period 316. Specifically, pulse P3 occurs during the blanking period 316 beginning at the end of the readout period 302 for exposure frame F1 and ending at the beginning of the readout period 302 for exposure frame F2. Pulse P6 occurs at the end of the readout period 302 for exposure frame F2.

FIG. 13B illustrates the resultant exposure frame F2 that is generated based on the light emitted by pulse P1 as shown in FIG. 13A. The readout for a certain pulse is read out on the next subsequent readout period 302. The readout of the top row (for example row 0) until row n will happen prior to pulse P1. As such, the entire light energy generated by pulse P1 is held on these rows until the next readout period 302. When pulse P1 and the readout period 302 occur concurrently, the part of the light that is generated between the start of the strobe and the exposure frame F1 readout of a given row is read out on the exposure frame F1. The light of the remaining part of the light pulse (after the exposure frame F1 readout of the given row) will be seen during the exposure frame F2 readout for that given row. The rows that are concerned with the splitting of the light are between row n and row n'.

By way of example, if it is supposed that the fifth row after the start of pulse P1 (i.e., row n+5) is being read out (during exposure frame F1 readout), then an equivalent of 5-line times of the light pulse has been integrated and read out during the exposure frame F1 readout. The remaining part of the pulse 902, which is the pulse width minus 5-line times, will be read out on the exposure frame F2 readout. Because the exposure frame F1 readout occurs after the pulse P1 strobe, the light information generated on the pixels from row n' to the end of the pixel array will be read out during the exposure frame F1 readout and nothing relative to pulse P1 will be present at the time of the exposure frame F2 readout, leading to a black area within exposure frame F2.

Because the line time of the sensor (Tline) and the pulse width (Tpulse) are precisely controlled and timed, the light deficit on the rows between row n and row n' at the exposure frame F2 readout can be calculated as a function of line position. First, one needs to calculate the number of rolling rows (Δ) during strobe width, wherein in the FIG. 17B example n'=n+Δ:

$$\Delta = \frac{Tpulse}{Tline}$$

For pulses 902 occurring during the exposure frame F1 readout (e.g., pulse P1), the relative illumination (I) of a row x collected in the F2 frame can be expressed by:

$$x < n \to I = 1$$
$$n \leq x \leq n + \Delta \to I = 1 - \frac{x-n}{\Delta}$$
$$x > n + \Delta \to I = 0$$

This is illustrated in the graph (row position) versus (relative light intensity). With very similar reasoning, the expression of the relative illumination (I) of a row x collected during the exposure frame F2 readout for pulses occurring during the exposure frame F2 readout is:

$$x < o \to I = 0$$
$$o \leq x \leq o + \Delta \to I = \frac{x-o}{\Delta}$$
$$x > o + \Delta \to I = 1$$

FIG. 13C is a representation of (row position) versus (relative light intensity) for each of the pulses P1, P2, P3, P4, and P5 from the example in FIG. 13A. As explained above, pulse P1 and pulse P2 occur during the exposure frame F1 readout and have the full light illumination for the top rows and have black bottom rows. In turn, pulses P4 and P5 occur during the exposure frame F2 readout and have black top rows and fully illuminated bottom rows. In all cases, a linear transition happens when the exposure frame F1 and exposure frame F2 readouts are concurrent. The image from pulse P3 has full illumination because pulse P3 is positioned during the sensor blanking period 316.

In an embodiment, a resultant combined exposure frame is generated by superimposing all exposure frames relative to the relevant pulses of electromagnetic radiation. In such an embodiment, the combined exposure frame represents a single exposure frame for a certain wavelength of electromagnetic radiation. The combined exposure frame may include data from multiple partial exposure frames captured over several readout periods of the image sensor. It may be necessary to capture multiple partial exposure frames depending on the frequency of the patient's vocal cords, and therefore the matching frequency of the pulses of electromagnetic radiation emitted by the emitter. In an embodiment where multiple partial exposure frames are combined to generate a combined exposure frame, the image signal processor (ISP) pipeline can keep track of the light deficiency for each row and then apply a row-wise digital gain to normalize the resultant image into an artifact-free image. In an implementation, the intensity of the emitter is controlled during each pulse of electromagnetic radiation to maintain a desired constant output level at any pulsing frequency.

It will be appreciated that the disclosure may be used with any image sensor, whether a CMOS image sensor or CCD image sensor, without departing from the scope of the disclosure. Further, the image sensor may be located in any location within the overall system, including, but not limited to, the tip of the endoscope, the hand piece of the imaging device or camera, the control unit, or any other location within the system without departing from the scope of the disclosure.

Figure 14:
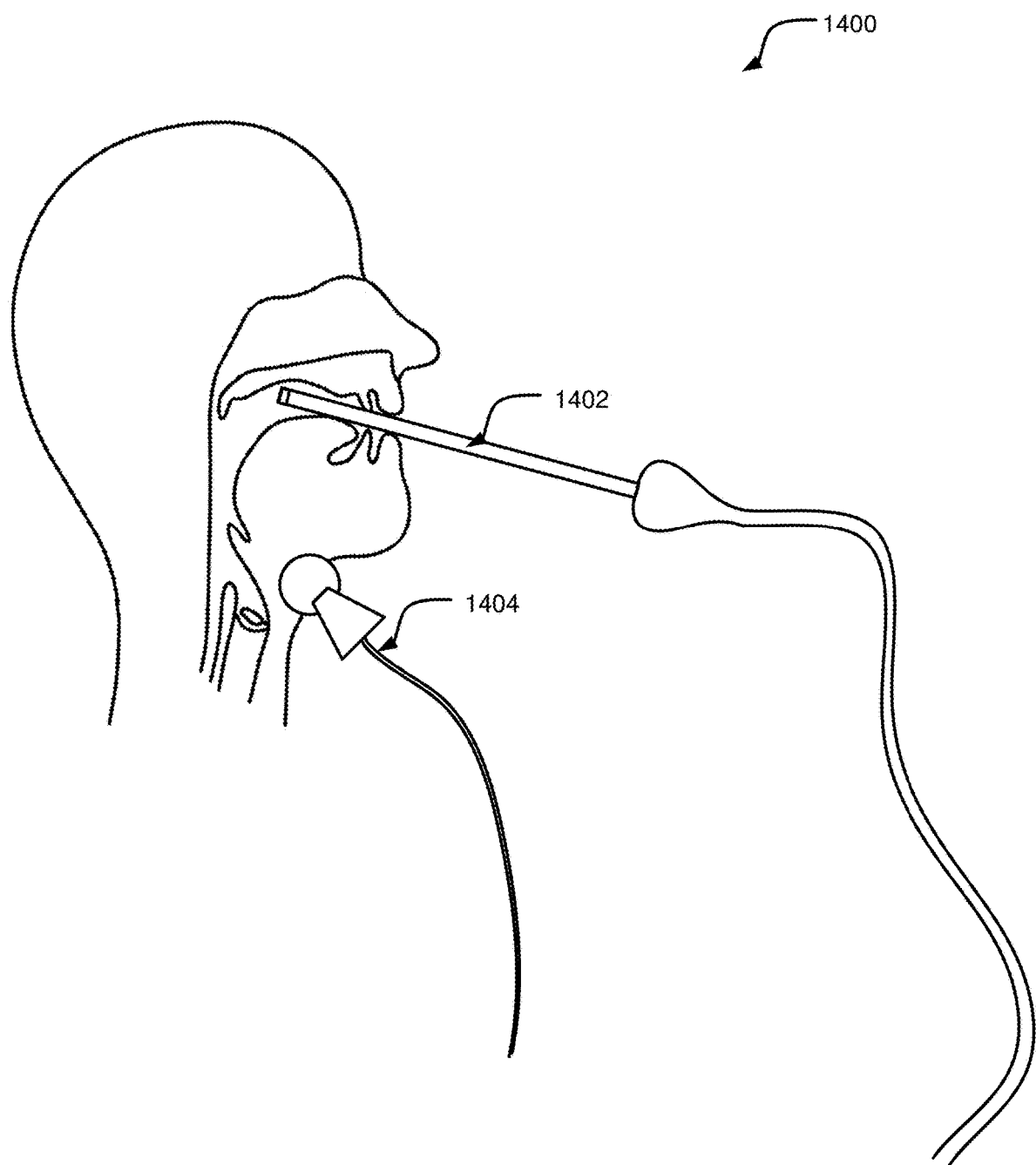
FIG. 14 illustrates an example system for videostroboscopy.

FIG. 14 illustrates an embodiment of a system 1400 for videostroboscopy. The system 1400 includes an endoscopic imaging device 1402 and a microphone 1404. In an embodiment, the endoscopic imaging device 1402 includes the components of the system 200 illustrated in FIG. 2. The endoscopic imaging device 1402 may be inserted into the mouth of a patient at the back of the patient's throat. The endoscopic imaging device 1402 may bend or include a mirror to enable the image sensor to capture images of the patient's vocal cords and larynx.

The system 1400 includes a microphone that may be placed against the patient's neck. In an embodiment, the microphone 1404 is attached to a band that is secured around the patient's neck such that the microphone 1404 is in contact with the patient's neck skin. It should be appreciated that any suitable microphone may be used, and the microphone is not necessarily in contact with the patient's neck. In an embodiment, the patient is instructed to make a sound, and the microphone 1404 captures the sound emitted by the patient's vocal cords. The sound captured by the microphone 1404 may be fed to a processor, such as the controller 1604 or some other processor 1604 configured to calculate the frequency of the sound emitted by the patient. During conversational speech, the vocal cords of a typical male patient may vibrate an average of 100-130 Hz while the vocal cords of a typical female patient may vibrate 190-220 Hz. The frequency of the pulses of electromagnetic radiation emitted by the emitter 202 of the endoscopic imaging device 1402 may be timed to match the frequency of the patient's vocal cords. For example, if the patient's vocal cords are vibrating at a frequency of 120 cycles per second, then the emitter may pulse an emission of electromagnetic radiation at a frequency of 120 times per second. The typical for the light strobing by the emitter may be 60 Hz to 1000 Hz, and this may depend on the frequency of vibrations performed by the patient's vocal cords.

In an embodiment, the microphone 1404 is in communication with one or more processors configured to process the sound captured by the microphone 1404 to detect the frequency of the sound waves. In an embodiment, the microphone 1404 is in direct communication with the same controller 204 configured to time the emitter 202 and the image sensor 214. In an embodiment, the microphone 1404 is in direct communication with a different computing device, and that computing device then provides the frequency of the patient's vocal cords to the controller 204.

In an embodiment, the strobing of pulses of electromagnetic radiation by the emitter 202 of the endoscopic imaging device 1402 includes a plurality of different wavelengths of electromagnetic radiation as discussed herein. In some embodiments and depending on the frequency of the patient's vocal cords, the emitter 202 may pulse the same wavelength of electromagnetic radiation in succession, and multiple partial exposure frames may be generated and then combined to form a single combined exposure frame for that wavelength of electromagnetic radiation. Then, multiple combined exposure frames for different wavelengths of electromagnetic radiation may be combined to form an image frame. Therefore, in some embodiments, a single color image frame may include a combined red exposure frame, a combined green exposure frame, and a combined blue exposure frame. Each of the combined red exposure frame, combined green exposure frame, and combined blue exposure frame may be generated with data from multiple partial exposure frames captured in response to pulses of red, green, or blue wavelengths of electromagnetic radiation. This can also be applied to one or more of a hyperspectral exposure frame, a fluorescence exposure frame, and/or a laser mapping exposure frame.

In an embodiment, the emitter emits pulses of electromagnetic radiation at a higher frequency than the cycles of readout periods and blanking periods for the image sensor. Said another way, the duration of a pulse of electromagnetic radiation (as determined based on the frequency of the patient's vocal cords) may be so short that the entire pixel array of the image sensor cannot be read in a single readout period following a single pulse of electromagnetic radiation during the prior blanking period. In such an embodiment, the pixel array of the image sensor must be read over the course of multiple pulses of electromagnetic radiation of the same wavelength in order to capture data across the entire pixel array for that wavelength of electromagnetic radiation.

Figure 15:
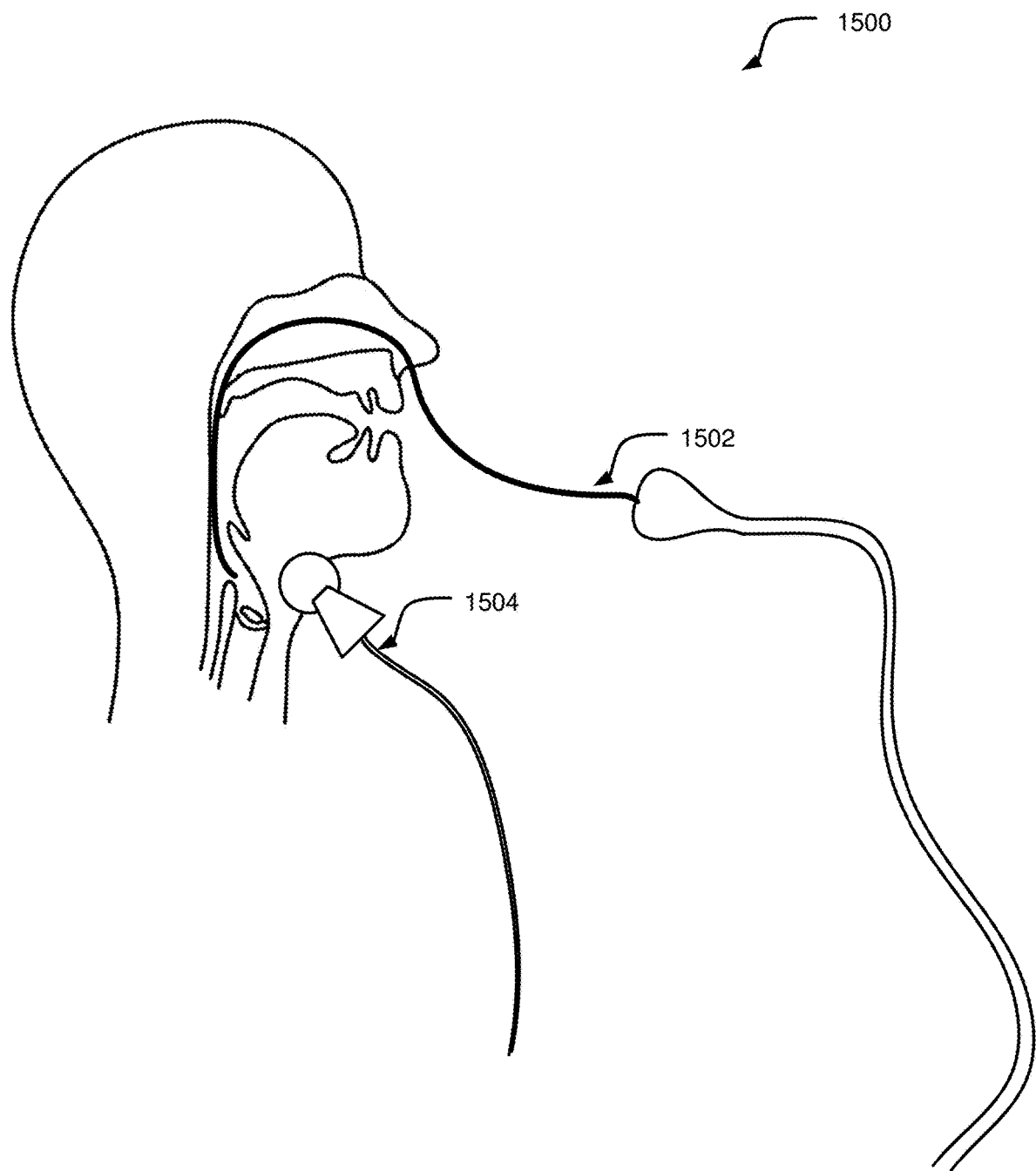
FIG. 15 illustrates an example system for videostroboscopy.

FIG. 15 illustrates an alternative embodiment of a system 1500 for videostroboscopy imaging. In the system 1500, the endoscopic imaging device 1502 includes a flexible tube that can be inserted through the patient's nasal cavity. The microphone 1504 is similar to the microphone 1404 discussed with respect to FIG. 14.

Figure 16:
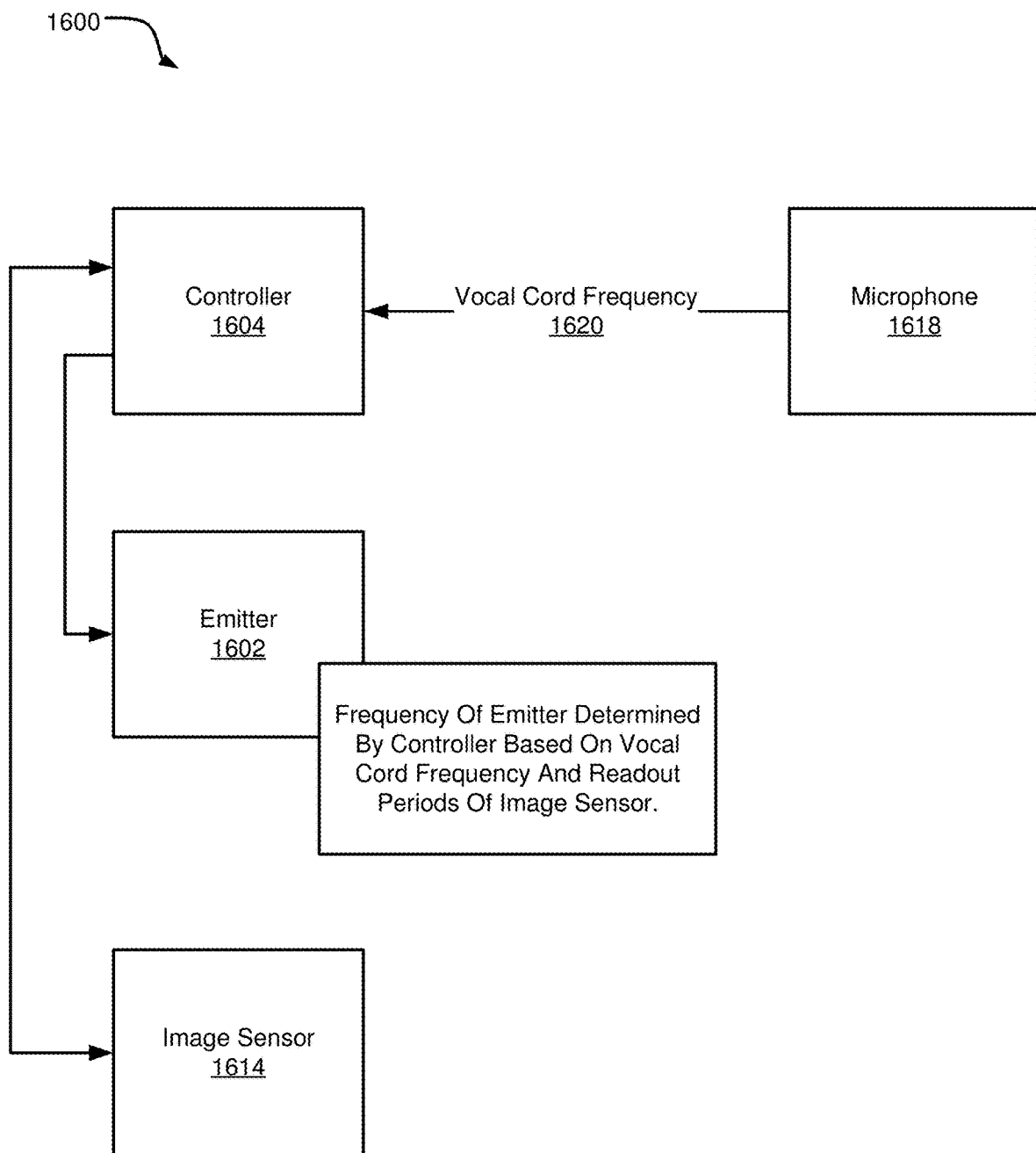
FIG. 16 is a schematic diagram of a system for videostroboscopy with a pulsed endoscopic imaging system.

FIG. 16 is a schematic diagram of a system 1600 for videostroboscopy imaging. The system 1600 includes a controller 1604 in communication with an emitter 1602 and an image sensor 1614. The emitter 1602 is configured to emit pulses of electromagnetic radiation. The image sensor 1614 comprises a pixel array for sensing reflected electromagnetic radiation. The controller 1604 is in direct or indirect communication with a microphone 1618. The microphone 1618 captures sound emitted by a patient.

The microphone 1618 may be in communication with a processor or other computing device configured to calculate the frequency of the vibrations of the patient's vocal cords based on the sound captured by the microphone 1618. The vocal cord frequency 1620 is provided to the controller. In an embodiment, the controller 1604 calculates the vocal cord frequency 1620 based on the sound captured by the microphone 1618. Alternatively, the microphone 1618 itself comprises a processor for calculating the frequency or the microphone 1618 is in communication with some other processor for calculating the frequency, and then the vocal cord frequency 1620 is provided to the controller.

The controller 1604 causes the emitter 1602 to strobe pulses of electromagnetic radiation at the same frequency as the vocal cord frequency 1620. The controller 1604 may cause the emitter 1602 to emit the pulses of electromagnetic radiation at a frequency similar to the vocal cord frequency and/or some multiple of the vocal cord frequency 1620. The controller 1604 causes the emitter 1602 to emit varying wavelengths of electromagnetic radiation for generating a color (RGB or YCbCr) image with hyperspectral, fluorescence, and/or laser mapping imaging data overlaid thereon, as discussed herein.

The controller 1604 times the sequence of readout periods and blanking periods of the image sensor 1614. Depending on how quickly the pixel array of the image sensor 1614 can be read, and depending on the vocal cord frequency 1620, the controller 1604 may cause the image sensor 1614 to capture data for a single combined exposure frame over multiple iterations of readout periods and blanking periods. This is illustrated in FIGS. 12A-12B. The controller 1604 may cause one or more pulses of electromagnetic radiation to be suppressed if those pulses occur during a readout period of the image sensor 1614.

Figure 17A:
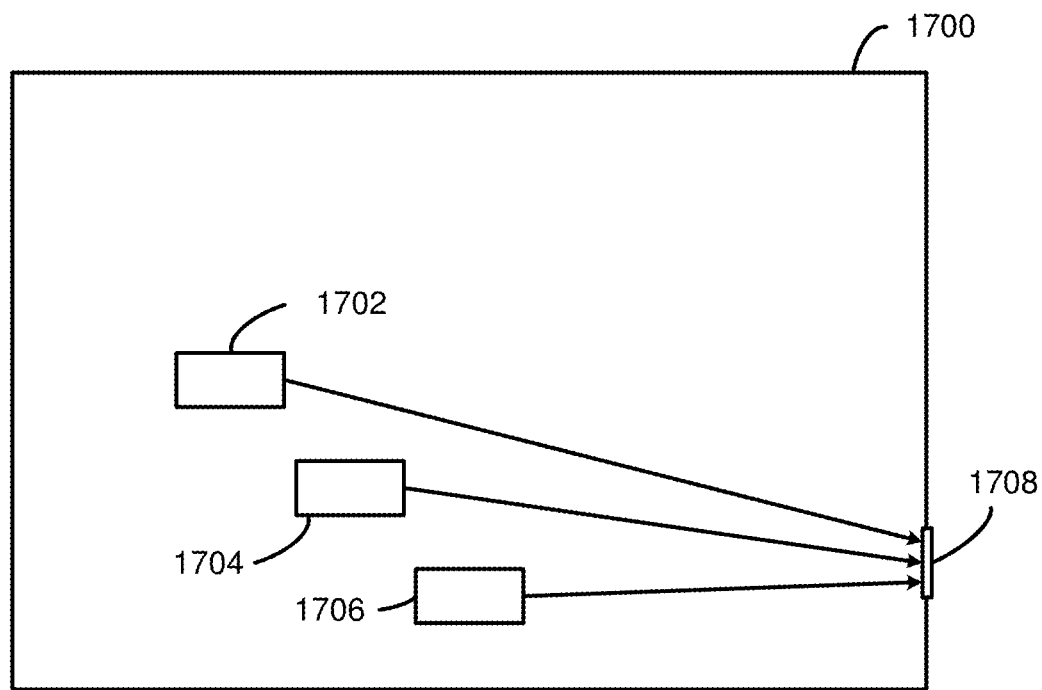
FIGS. 17A-17C illustrate a light source having a plurality of emitters.
Figure 17B:
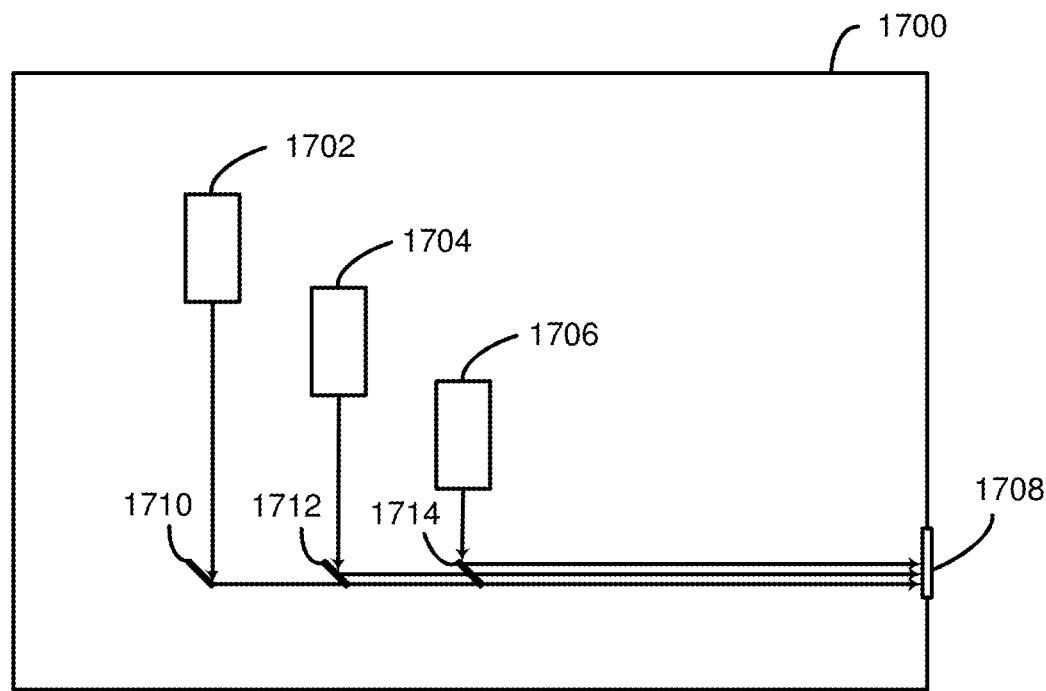
Figure 17C:
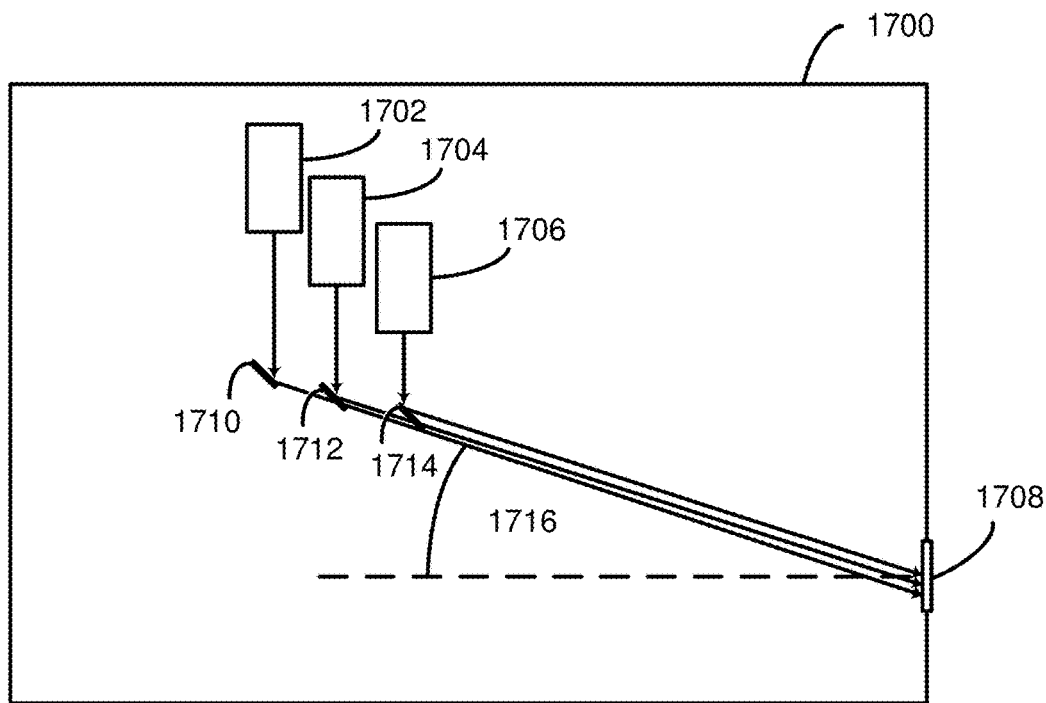

FIGS. 17A-17C each illustrate a light source 1700 having a plurality of emitters. The light source 1700 can collectively be referred to as an "emitter" herein. The plurality of emitters include a first emitter 1702, a second emitter 1704, and a third emitter 1706. Additional emitters may be included, as discussed further below. The emitters 1702, 1704, and 1706 may include one or more laser emitters that emit light having different wavelengths. For example, the first emitter 1702 may emit a wavelength that is consistent with a blue laser, the second emitter 1704 may emit a wavelength that is consistent with a green laser, and the third emitter 1706 may emit a wavelength that is consistent with a red laser. For example, the first emitter 1702 may include one or more blue lasers, the second emitter 1704 may include one or more green lasers, and the third emitter 1706 may include one or more red lasers. The emitters 1702, 1704, 1706 emit laser beams toward a collection region 1708, which may be the location of a waveguide, lens, or other optical component for collecting and/or providing light to a waveguide, such as the jumper waveguide 206 or lumen waveguide 210 of FIG. 2.

In an implementation, the emitters 1702, 1704, and 1706 emit hyperspectral wavelengths of electromagnetic radiation. Certain hyperspectral wavelengths may pierce through tissue and enable a medical practitioner to "see through" tissues in the foreground to identify chemical processes, structures, compounds, biological processes, and so forth that are located behind the tissues in the foreground. The hyperspectral wavelengths may be specifically selected to identify a specific disease, tissue condition, biological process, chemical process, type of tissue, and so forth that is known to have a certain spectral response.

In an implementation where a patient has been administered a reagent or dye to aid in the identification of certain tissues, structures, chemical reactions, biological processes, and so forth, the emitters 1702, 1704, and 1706 may emit wavelength(s) for fluorescing the reagents or dyes. Such wavelength(s) may be determined based on the reagents or dyes administered to the patient. In such an embodiment, the emitters may need to be highly precise for emitting desired wavelength(s) to fluoresce or activate certain reagents or dyes.

In an implementation, the emitters 1702, 1704, and 1706 emit a laser mapping pattern for mapping a topology of a scene and/or for calculating dimensions and distances between objects in the scene. In an embodiment, the endoscopic imaging system is used in conjunction with multiple tools such as scalpels, retractors, forceps, and so forth. In such an embodiment, each of the emitters 1702, 1704, and 1706 may emit a laser mapping pattern such that a laser mapping pattern is projected on to each tool individually. In such an embodiment, the laser mapping data for each of the tools can be analyzed to identify distances between the tools and other objects in the scene.

In the embodiment of FIG. 17B, the emitters 1702, 1704, 1706 each deliver laser light to the collection region 1708 at different angles. The variation in angle can lead to variations where electromagnetic energy is located in an output waveguide. For example, if the light passes immediately into a fiber bundle (glass or plastic) at the collection region 1708, the varying angles may cause different amounts of light to enter different fibers. For example, the angle may result in intensity variations across the collection region 1708. Furthermore, light from the different emitters may not be homogenously mixed so some fibers may receive different amounts of light of different colors. Variation in the color or intensity of light in different fibers can lead to non-optimal illumination of a scene. For example, variations in delivered light or light intensities may result at the scene and captured images.

In one embodiment, an intervening optical element may be placed between a fiber bundle and the emitters 1702, 1704, 1706 to mix the different colors (wavelengths) of light before entry into the fibers or other waveguide. Example intervening optical elements include a diffuser, mixing rod, one or more lenses, or other optical components that mix the light so that a given fiber receive a same amount of each color (wavelength). For example, each fiber in the fiber bundle may have a same color. This mixing may lead to the same color in each fiber but may, in some embodiments, still result in different total brightness delivered to different fibers. In one embodiment, the intervening optical element may also spread out or even out the light over the collection region so that each fiber carries the same total amount of light (e.g., the light may be spread out in a top hat profile). A diffuser or mixing rod may lead to loss of light.

Although the collection region 1708 is represented as a physical component in FIG. 17A, the collection region 1708 may simply be a region where light from the emitters 1702, 1704, and 1706 is delivered. In some cases, the collection region 1708 may include an optical component such as a diffuser, mixing rod, lens, or any other intervening optical component between the emitters 1702, 1704, 1706 and an output waveguide.

FIG. 17C illustrates an embodiment of a light source 1700 with emitters 1702, 1704, 1706 that provide light to the collection region 1708 at the same or substantially same angle. The light is provided at an angle substantially perpendicular to the collection region 1708. The light source 1700 includes a plurality of dichroic mirrors including a first dichroic mirror 1710, a second dichroic mirror 1712, and a third dichroic mirror 1714. The dichroic mirrors 1710, 1712, 1714 include mirrors that reflect a first wavelength of light but transmit (or are transparent to) a second wavelength of light. For example, the third dichroic mirror 1714 may reflect blue laser light provided by the third emitter, while being transparent to the red and green light provided by the first emitter 1702 and the second emitter 1704, respectively. The second dichroic mirror 1712 may be transparent to red light from the first emitter 1702, but reflective to green light from the second emitter 1704. If other colors or wavelengths are included dichroic mirrors may be selected to reflect light corresponding to at least one emitter and be transparent to other emitters. For example, the third dichroic mirror 1714 reflect the light form the third emitter 1706 but is to emitters "behind" it, such as the first emitter 1702 and the second emitter 1704. In embodiments where tens or hundreds of emitters are present, each dichroic mirror may be reflective to a corresponding emitter and emitters in front of it while being transparent to emitters behind it. This may allow for tens or hundreds of emitters to emit electromagnetic energy to the collection region 1708 at a substantially same angle.

Because the dichroic mirrors allow other wavelengths to transmit or pass through, each of the wavelengths may arrive at the collection region 1708 from a same angle and/or with the same center or focal point. Providing light from the same angle and/or same focal/center point can significantly improve reception and color mixing at the collection region 1708. For example, a specific fiber may receive the different colors in the same proportions they were transmitted/reflected by the emitters 1702, 1704, 1706 and mirrors 1710, 1712, 1714. Light mixing may be significantly improved at the collection region compared to the embodiment of FIG. 17B. In one embodiment, any optical components discussed herein may be used at the collection region 1708 to collect light prior to providing it to a fiber or fiber bundle.

FIG. 17C illustrates an embodiment of a light source 1700 with emitters 1702, 1704, 1706 that also provide light to the collection region 1708 at the same or substantially same angle. However, the light incident on the collection region 1708 is offset from being perpendicular. Angle 1716 indicates the angle offset from perpendicular. In one embodiment, the laser emitters 1702, 1704, 1706 may have cross sectional intensity profiles that are Gaussian. As discussed previously, improved distribution of light energy between fibers may be accomplished by creating a more flat or top-hat shaped intensity profile. In one embodiment, as the angle 1716 is increased, the intensity across the collection region 1708 approaches a top hat profile. For example, a top-hat profile may be approximated even with a non-flat output beam by increasing the angle 1716 until the profile is sufficiently flat. The top hat profile may also be accomplished using one or more lenses, diffusers, mixing rods, or any other intervening optical component between the emitters 1702, 1704, 1706 and an output waveguide, fiber, or fiber optic bundle.

Figure 18:
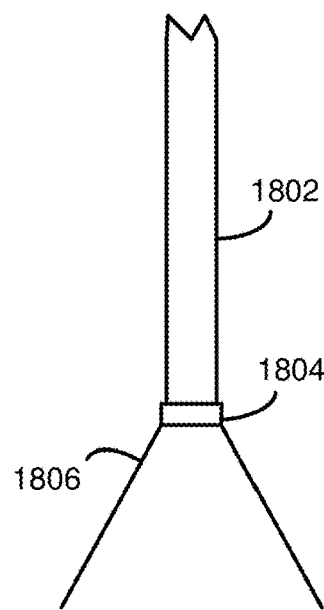
FIG. 18 illustrates a single optical fiber outputting via a diffuser at an output to illuminate a scene in a light deficient environment.

FIG. 18 is a schematic diagram illustrating a single optical fiber 1802 outputting via a diffuser 1804 at an output. In one embodiment, the optical fiber 1802 has a diameter of 500 microns, a numerical aperture of 0.65, and emits a light cone 1806 of about 70 or 80 degrees without a diffuser 1804. With the diffuser 1804, the light cone 1806 may have an angle of about 110 or 120 degrees. The light cone 1806 may be a majority of where all light goes and is evenly distributed. The diffuser 1804 may allow for more even distribution of electromagnetic energy of a scene observed by an image sensor.

In one embodiment, the lumen waveguide 210 includes a single plastic or glass optical fiber of about 500 microns. The plastic fiber may be low cost, but the width may allow the fiber to carry a sufficient amount of light to a scene, with coupling, diffusion, or other losses. For example, smaller fibers may not be able to carry as much light or power as a larger fiber. The lumen waveguide 210 may include a single or a plurality of optical fibers. The lumen waveguide 210 may receive light directly from the light source or via a jumper waveguide. A diffuser may be used to broaden the light output 206 for a desired field of view of the image sensor 214 or other optical components.

Although three emitters are shown in FIGS. 17A-17C, emitters numbering from one into the hundreds or more may be used in some embodiments. The emitters may have different wavelengths or spectrums of light that they emit, and which may be used to contiguously cover a desired portion of the electromagnetic spectrum (e.g., the visible spectrum as well as infrared and ultraviolet spectrums). The emitters may be configured to emit visible light such as red light, green light, and blue light, and may further be configured to emit hyperspectral emissions of electromagnetic radiation, fluorescence excitation wavelengths for fluorescing a reagent, and/or laser mapping patterns for calculating parameters and distances between objects in a scene.

Figure 19:
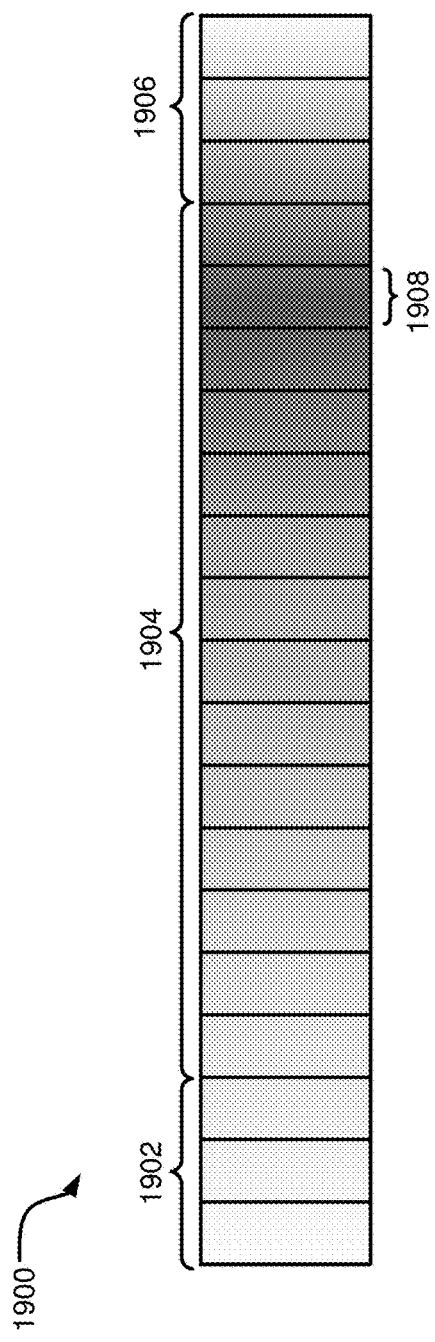
FIG. 19 illustrates a portion of the electromagnetic spectrum divided into a plurality of different sub-spectrums which may be emitted by emitters of a light source in accordance with the principles and teachings of the disclosure.

FIG. 19 illustrates a portion of the electromagnetic spectrum 1900 divided into twenty different sub-spectrums. The number of sub-spectrums is illustrative only. In at least one embodiment, the spectrum 1900 may be divided into hundreds of sub-spectrums, each with a small waveband. The spectrum may extend from the infrared spectrum 1902, through the visible spectrum 1904, and into the ultraviolet spectrum 1906. The sub-spectrums each have a waveband 1908 that covers a portion of the spectrum 1900. Each waveband may be defined by an upper wavelength and a lower wavelength.

Hyperspectral imaging includes imaging information from across the electromagnetic spectrum 1900. A hyperspectral pulse of electromagnetic radiation may include a plurality of sub-pulses spanning one or more portions of the electromagnetic spectrum 1900 or the entirety of the electromagnetic spectrum 1900. A hyperspectral pulse of electromagnetic radiation may include a single partition of wavelengths of electromagnetic radiation. A resulting hyperspectral exposure frame includes information sensed by the pixel array subsequent to a hyperspectral pulse of electromagnetic radiation. Therefore, a hyperspectral exposure frame may include data for any suitable partition of the electromagnetic spectrum 1900 and may include multiple exposure frames for multiple partitions of the electromagnetic spectrum 1900. In an embodiment, a hyperspectral exposure frame includes multiple hyperspectral exposure frames such that the combined hyperspectral exposure frame comprises data for the entirety of the electromagnetic spectrum 1900.

In one embodiment, at least one emitter (such as a laser emitter) is included in a light source (such as the light sources 202, 1700) for each sub-spectrum to provide complete and contiguous coverage of the whole spectrum 1900. For example, a light source for providing coverage of the illustrated sub-spectrums may include at least 20 different emitters, at least one for each sub-spectrum. In one embodiment, each emitter covers a spectrum covering 40 nanometers. For example, one emitter may emit light within a waveband from 500 nm to 540 nm while another emitter may emit light within a waveband from 540 nm to 580 nm. In another embodiment, emitters may cover other sizes of wavebands, depending on the types of emitters available or the imaging needs. For example, a plurality of emitters may include a first emitter that covers a waveband from 500 to 540 nm, a second emitter that covers a waveband from 540 nm to 640 nm, and a third emitter that covers a waveband from 640 nm to 650 nm. Each emitter may cover a different slice of the electromagnetic spectrum ranging from far infrared, mid infrared, near infrared, visible light, near ultraviolet and/or extreme ultraviolet. In some cases, a plurality of emitters of the same type or wavelength may be included to provide sufficient output power for imaging. The number of emitters needed for a specific waveband may depend on the sensitivity of a monochrome sensor to the waveband and/or the power output capability of emitters in that waveband.

The waveband widths and coverage provided by the emitters may be selected to provide any desired combination of spectrums. For example, contiguous coverage of a spectrum using very small waveband widths (e.g., 10 nm or less) may allow for highly selective hyperspectral and/or fluorescence imaging. The waveband widths may allow for selectively emitting the excitation wavelength(s) for one or more particular fluorescent reagents. Additionally, the waveband widths may allow for selectively emitting certain partitions of hyperspectral electromagnetic radiation for identifying specific structures, chemical processes, tissues, biological processes, and so forth. Because the wavelengths come from emitters which can be selectively activated, extreme flexibility for fluorescing one or more specific fluorescent reagents during an examination can be achieved. Additionally, extreme flexibility for identifying one or more objects or processes by way of hyperspectral imaging can be achieved. Thus, much more fluorescence and/or hyperspectral information may be achieved in less time and within a single examination which would have required multiple examinations, delays because of the administration of dyes or stains, or the like.

Figure 20:
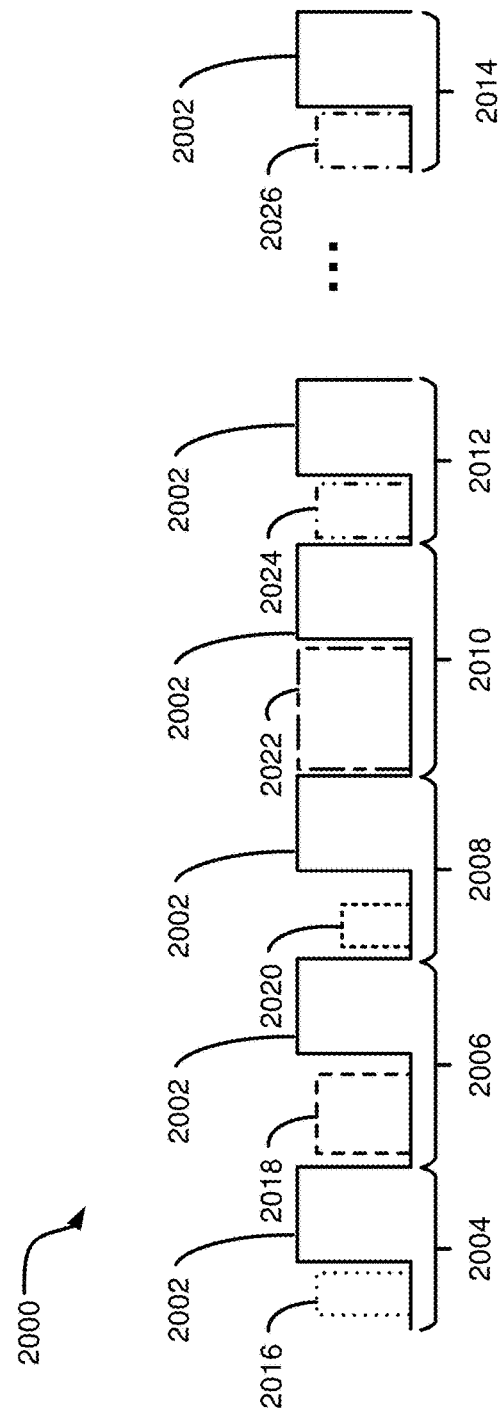
FIG. 20 is a schematic diagram illustrating a timing sequence for emission and readout for generating an image frame comprising a plurality of exposure frames resulting from differing partitions of pulsed light.

FIG. 20 is a schematic diagram illustrating a timing diagram 2000 for emission and readout for generating an image. The solid line represents readout (peaks 2002) and blanking periods (valleys) for capturing a series of exposure frames 2004-2014. The series of exposure frames 2004-2014 may include a repeating series of exposure frames which may be used for generating laser mapping, hyperspectral, and/or fluorescence data that may be overlaid on an RGB video stream. In an embodiment, a single image frame comprises information from multiple exposure frames, wherein one exposure frame includes red image data, another exposure frame includes green image data, and another exposure frame includes blue image data. Additionally, the single image frame may include one or more of hyperspectral image data, fluorescence image data, and laser mapping data. The multiple exposure frames are combined to produce the single image frame. The single image frame is an RGB image with hyperspectral imaging data. The series of exposure frames include a first exposure frame 2004, a second exposure frame 2006, a third exposure frame 2008, a fourth exposure frame 2010, a fifth exposure frame 2012, and an Nth exposure frame 2026.

Additionally, the hyperspectral image data, the fluorescence image data, and the laser mapping data can be used in combination to identify critical tissues or structures and further to measure the dimensions of those critical tissues or structures. For example, the hyperspectral image data may be provided to a corresponding system to identify certain critical structures in a body such as a nerve, ureter, blood vessel, cancerous tissue, and so forth. The location and identification of the critical structures may be received from the corresponding system and may further be used to generate topology of the critical structures using the laser mapping data. For example, a corresponding system determines the location of a cancerous tumor based on hyperspectral imaging data. Because the location of the cancerous tumor is known based on the hyperspectral imaging data, the topology and distances of the cancerous tumor may then be calculated based on laser mapping data. This example may also apply when a cancerous tumor or other structure is identified based on fluorescence imaging data.

In one embodiment, each exposure frame is generated based on at least one pulse of electromagnetic energy. The pulse of electromagnetic energy is reflected and detected by an image sensor and then read out in a subsequent readout (2002). Thus, each blanking period and readout results in an exposure frame for a specific spectrum of electromagnetic energy. For example, the first exposure frame 2004 may be generated based on a spectrum of a first one or more pulses 2016, a second exposure frame 2006 may be generated based on a spectrum of a second one or more pulses 2018, a third exposure frame 2008 may be generated based on a spectrum of a third one or more pulses 2020, a fourth exposure frame 2010 may be generated based on a spectrum of a fourth one or more pulses 2022, a fifth exposure frame 2012 may be generated based on a spectrum of a fifth one or more pulses, and an Nth exposure frame 2026 may be generated based on a spectrum of an Nth one or more pulses 2026.

The pulses 2016-2026 may include energy from a single emitter or from a combination of two or more emitters. For example, the spectrum included in a single readout period or within the plurality of exposure frames 2004-2014 may be selected for a desired examination or detection of a specific tissue or condition. According to one embodiment, one or more pulses may include visible spectrum light for generating an RGB or black and white image while one or more additional pulses are emitted to sense a spectral response to a hyperspectral wavelength of electromagnetic radiation. For example, pulse 2016 may include red light, pulse 2018 may include blue light, and pulse 2020 may include green light while the remaining pulses 2022-2026 may include wavelengths and spectrums for detecting a specific tissue type, fluorescing a reagent, and/or mapping the topology of the scene. As a further example, pulses for a single readout period include a spectrum generated from multiple different emitters (e.g., different slices of the electromagnetic spectrum) that can be used to detect a specific tissue type. For example, if the combination of wavelengths results in a pixel having a value exceeding or falling below a threshold, that pixel may be classified as corresponding to a specific type of tissue. Each frame may be used to further narrow the type of tissue that is present at that pixel (e.g., and each pixel in the image) to provide a very specific classification of the tissue and/or a state of the tissue (diseased/healthy) based on a spectral response of the tissue and/or whether a fluorescent reagent is present at the tissue.

The plurality of frames 2004-2014 is shown having varying lengths in readout periods and pulses having different lengths or intensities. The blanking period, pulse length or intensity, or the like may be selected based on the sensitivity of a monochromatic sensor to the specific wavelength, the power output capability of the emitter(s), and/or the carrying capacity of the waveguide.

In one embodiment, dual image sensors may be used to obtain three-dimensional images or video feeds. A three-dimensional examination may allow for improved understanding of a three-dimensional structure of the examined region as well as a mapping of the different tissue or material types within the region.

In an example implementation, a fluorescent reagent is provided to a patient, and the fluorescent reagent is configured to adhere to cancerous cells. The fluorescent reagent is known to fluoresce when radiated with a specific partition of electromagnetic radiation. The relaxation wavelength of the fluorescent reagent is also known. In the example implementation, the patient is imaged with an endoscopic imaging system as discussed herein. The endoscopic imaging system pulses partitions of red, green, and blue wavelengths of light to generate an RGB video stream of the interior of the patient's body. Additionally, the endoscopic imaging system pulses the excitation wavelength of electromagnetic radiation for the fluorescent reagent that was administered to the patient. In the example, the patient has cancerous cells and the fluorescent reagent has adhered to the cancerous cells. When the endoscopic imaging system pulses the excitation wavelength for the fluorescent reagent, the fluorescent reagent will fluoresce and emit a relaxation wavelength. If the cancerous cells are present in the scene being imaged by the endoscopic imaging system, then the fluorescent reagent will also be present in the scene and will emit its relaxation wavelength after fluorescing due to the emission of the excitation wavelength. The endoscopic imaging system senses the relaxation wavelength of the fluorescent reagent and thereby senses the presence of the fluorescent reagent in the scene. Because the fluorescent reagent is known to adhere to cancerous cells, the presence of the fluorescent reagent further indicates the presence of cancerous cells within the scene. The endoscopic imaging system thereby identifies the location of cancerous cells within the scene. The endoscopic imaging system may further emit a laser mapping pulsing scheme for generating a topology of the scene and calculating dimensions for objects within the scene. The location of the cancerous cells (as identified by the fluorescence imaging data) may be combined with the topology and dimensions information calculated based on the laser mapping data. Therefore, the precise location, size, dimensions, and topology of the cancerous cells may be identified. This information may be provided to a medical practitioner to aid in excising the cancerous cells. Additionally, this information may be provided to a robotic surgical system to enable the surgical system to excise the cancerous cells.

In a further example implementation, a patient is imaged with an endoscopic imaging system to identify quantitative diagnostic information about the patient's tissue pathology. In the example, the patient is suspected or known to suffer from a disease that can be tracked with hyperspectral imaging to observe the progression of the disease in the patient's tissue. The endoscopic imaging system pulses partitions of red, green, and blue wavelengths of light to generate an RGB video stream of the interior of the patient's body. Additionally, the endoscopic imaging system pulses one or more hyperspectral wavelengths of light that permit the system to "see through" some tissues and generate imaging of the tissue that is affected by the disease. The endoscopic imaging system senses the reflected hyperspectral electromagnetic radiation to generate hyperspectral imaging data of the diseased tissue, and thereby identifies the location of the diseased tissue within the patient's body. The endoscopic imaging system may further emit a laser mapping pulsing scheme for generating a topology of the scene and calculating dimensions of objects within the scene. The location of the diseased tissue (as identified by the hyperspectral imaging data) may be combined with the topology and dimensions information that is calculated with the laser mapping data. Therefore, the precise location, size, dimensions, and topology of the diseased tissue can be identified. This information may be provided to a medical practitioner to aid in excising, imaging, or studying the diseased tissue. Additionally, this information may be provided to a robotic surgical system to enable the surgical system to excise the diseased tissue.

Figure 21:
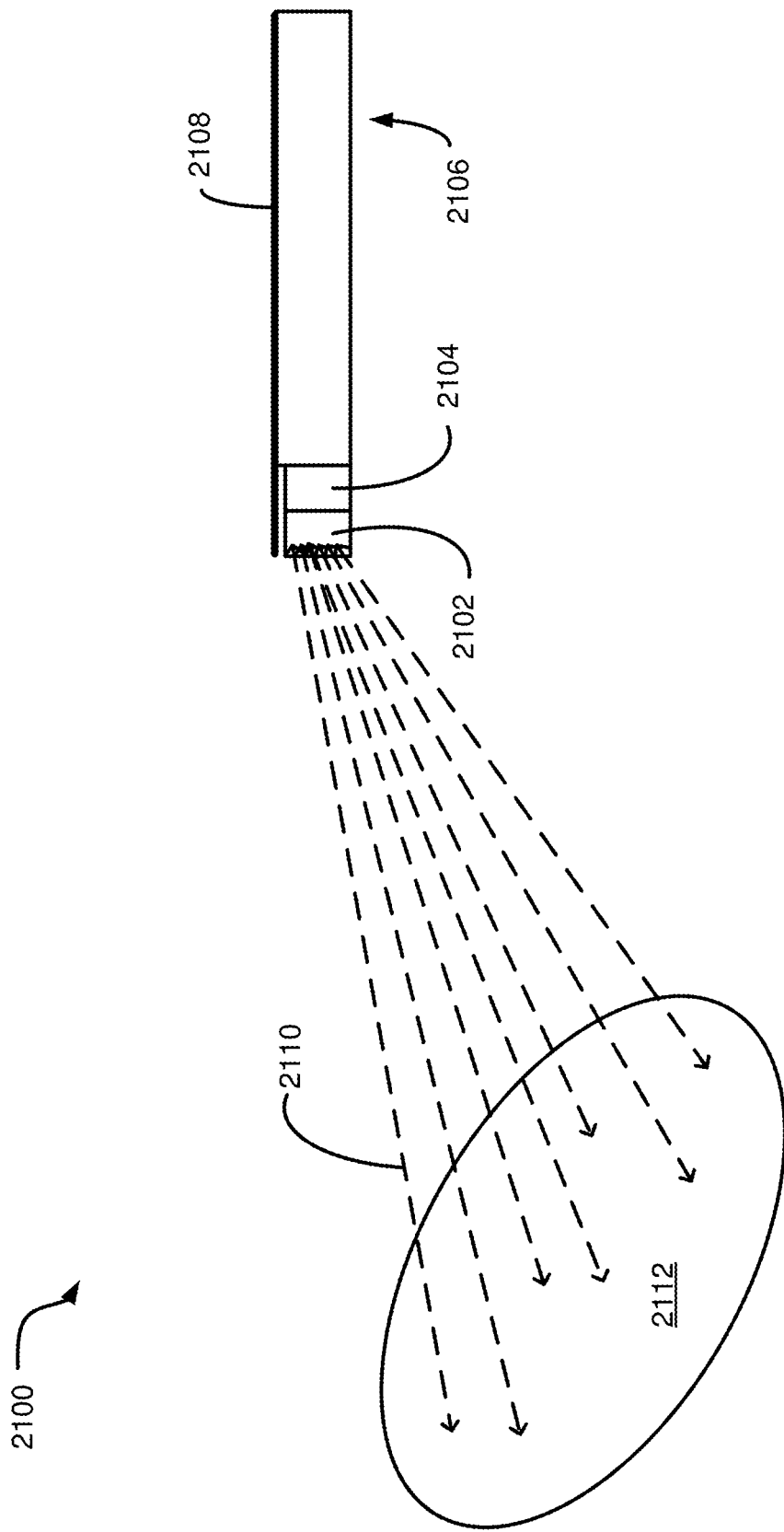
FIG. 21 illustrates an imaging system including a single cut filter for filtering wavelengths of electromagnetic radiation.

FIG. 21 is a schematic diagram of an imaging system 2100 having a single cut filter. The system 2100 includes an endoscope 2106 or other suitable imaging device having a light source 2108 for use in a light deficient environment. The endoscope 2106 includes an image sensor 2104 and a filter 2102 for filtering out unwanted wavelengths of light or other electromagnetic radiation before reaching the image sensor 2104. The light source 2108 transmits light that may illuminate the surface 2112 in a light deficient environment such as a body cavity. The light 2110 is reflected off the surface 2112 and passes through the filter 2102 before hitting the image sensor 2104.

The filter 2102 may be used in an implementation where a fluorescent reagent or dye has been administered. In such an embodiment, the light source 2108 emits the excitation wavelength for fluorescing the fluorescent reagent or dye. Commonly, the relaxation wavelength emitted by the fluorescent reagent or dye will be of a different wavelength than the excitation wavelength. The filter 2102 may be selected to filter out the excitation wavelength and permit only the relaxation wavelength to pass through the filter and be sensed by the image sensor 2104.

In one embodiment, the filter 2102 is configured to filter out an excitation wavelength of electromagnetic radiation that causes a reagent or dye to fluoresce such that only the expected relaxation wavelength of the fluoresced reagent or dye is permitted to pass through the filter 2102 and reach the image sensor 2104. In an embodiment, the filter 2102 filters out at least a fluorescent reagent excitation wavelength between 770 nm and 790 nm. In an embodiment, the filter 2102 filters out at least a fluorescent reagent excitation wavelength between 795 nm and 815 nm. In an embodiment, the filter 2102 filters out at least a fluorescent reagent excitation wavelength between 770 nm and 790 nm and between 795 nm and 815 nm. In these embodiments, the filter 2102 filters out the excitation wavelength of the reagent and permits only the relaxation wavelength of the fluoresced reagent to be read by the image sensor 2104. The image sensor 2104 may be a wavelength-agnostic image sensor and the filter 2102 may be configured to permit the image sensor 2104 to only receive the relaxation wavelength of the fluoresced reagent and not receive the emitted excitation wavelength for the reagent. The data determined by the image sensor 2104 may then indicate a presence of a critical body structure, tissue, biological process, or chemical process as determined by a location of the reagent or dye.

The filter 2102 may further be used in an implementation where a fluorescent reagent or dye has not been administered. The filter 2102 may be selected to permit wavelengths corresponding to a desired spectral response to pass through and be read by the image sensor 2104. The image sensor 2104 may be a monochromatic image sensor such that pixels of the captured image that exceed a threshold or fall below a threshold may be characterized as corresponding to a certain spectral response or fluorescence emission. The spectral response or fluorescence emission, as determined by the pixels captured by the image sensor 2104, may indicate the presence of a certain body tissue or structure, a certain condition, a certain chemical process, and so forth.

Figure 22:
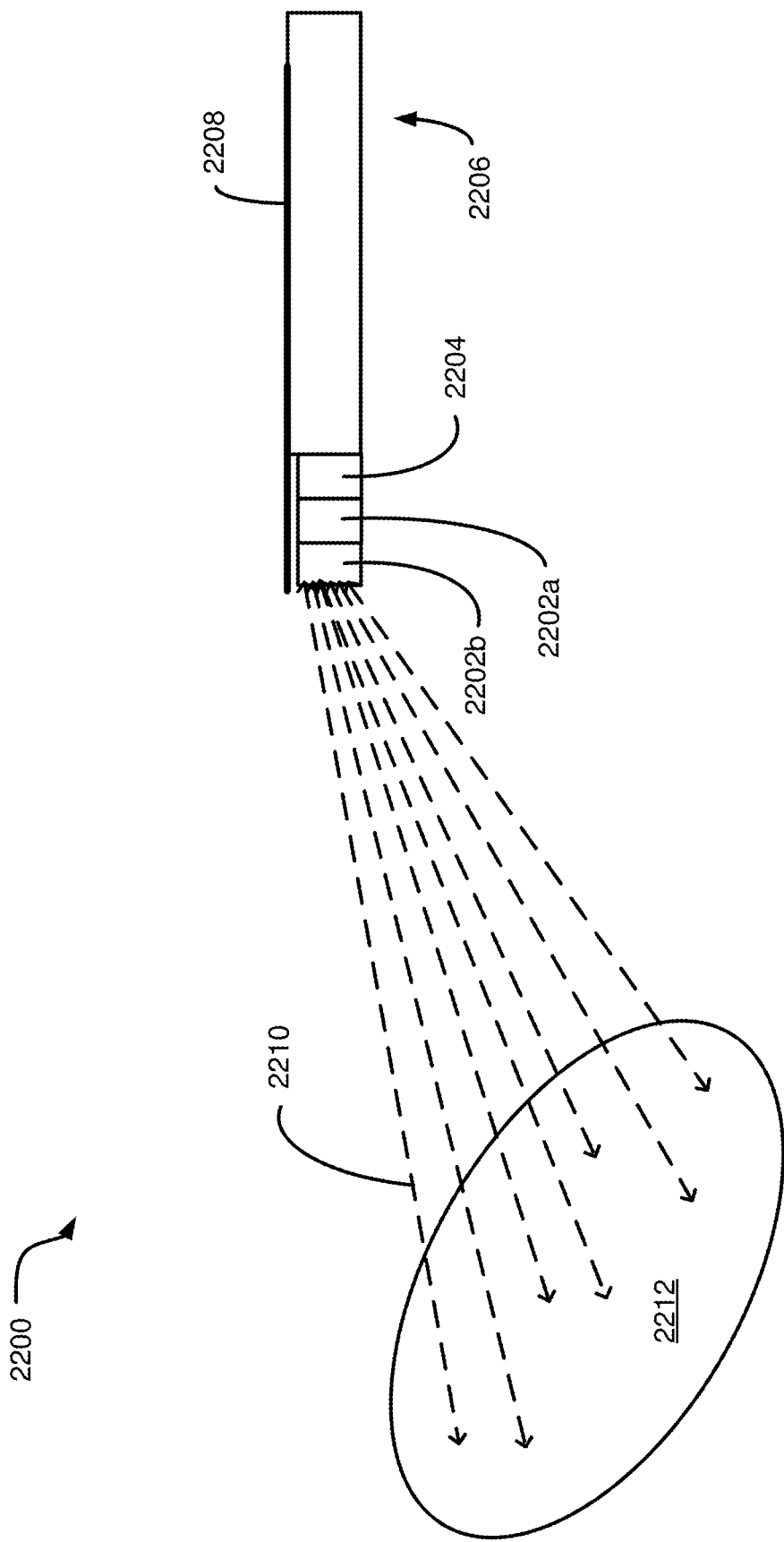
FIG. 22 illustrates an imaging system comprising a multiple cut filter for filtering wavelengths of electromagnetic radiation.

FIG. 22 is a schematic diagram of an imaging system 2200 having multiple cut filters. The system 2200 includes an endoscope 2206 or other suitable imaging device having a light source 2208 for use in a light deficient environment. The endoscope 2206 includes an image sensor 2204 and two filters 2202a, 2202b. It should be appreciated that in alternative embodiments, the system 2200 may include any number of filters, and the number of filters and the type of filters may be selected for a certain purpose e.g., for gathering imaging information of a particular body tissue, body condition, chemical process, and so forth. The filters 2202a, 2202b are configured for preventing unwanted wavelengths of light or other electromagnetic radiation from being sensed by the image sensor 2204. The filters 2202a, 2202b may be configured to filter out unwanted wavelengths from white light or other electromagnetic radiation that may be emitted by the light source 2208.

Further to the disclosure with respect to FIG. 21, the filters 2202a, 2202b may be used in an implementation where a fluorescent reagent or dye has been administered. The filters 2202a, 2202b may be configured for blocking an emitted excitation wavelength for the reagent or dye and permitting the image sensor 2204 to only read the relaxation wavelength of the reagent or dye. Further, the filters 2202a, 2202b may be used in an implementation where a fluorescent reagent or dye has not been administered. In such an implementation, the filters 2202a, 2202b may be selected to permit wavelengths corresponding to a desired spectral response to pass through and be read by the image sensor 2204.

The multiple filters 2202a, 2202b may each be configured for filtering out a different range of wavelengths of the electromagnetic spectrum. For example, one filter may be configured for filtering out wavelengths longer than a desired wavelength range and the additional filter may be configured for filtering out wavelengths shorter than the desired wavelength range. The combination of the two or more filters may result in only a certain wavelength or band of wavelengths being read by the image sensor 2204.

In an embodiment, the filters 2202a, 2202b are customized such that electromagnetic radiation between 513 nm and 545 nm contacts the image sensor 2204. In an embodiment, the filters 2202a, 2202b are customized such that electromagnetic radiation between 565 nm and 585 nm contacts the image sensor 2204. In an embodiment, the filters 2202a, 2202b are customized such that electromagnetic radiation between 900 nm and 1000 nm contacts the image sensor 2204. In an embodiment, the filters 2202a, 2202b are customized such that electromagnetic radiation between 421 nm and 475 nm contacts the image sensor 2204. In an embodiment, the filters 2202a, 2202b are customized such that electromagnetic radiation between 520 nm and 545 nm contacts the image sensor 2204. In an embodiment, the filters 2202a, 2202b are customized such that electromagnetic radiation between 617 nm and 645 nm contacts the image sensor 2204. In an embodiment, the filters 2202a, 2202b are customized such that electromagnetic radiation between 760 nm and 795 nm contacts the image sensor 2204. In an embodiment, the filters 2202a, 2202b are customized such that electromagnetic radiation between 795 nm and 815 nm contacts the image sensor 2204. In an embodiment, the filters 2202a, 2202b are customized such that electromagnetic radiation between 370 nm and 420 nm contacts the image sensor 2204. In an embodiment, the filters 2202a, 2202b are customized such that electromagnetic radiation between 600 nm and 670 nm contacts the image sensor 2204. In an embodiment, the filters 2202a, 2202b are configured for permitting only a certain fluorescence relaxation emission to pass through the filters 2202a, 2202b and contact the image sensor 2204. In an embodiment, a first filter blocks electromagnetic radiation having a wavelength from about 770 nm to about 790 nm, and a second filter blocks electromagnetic radiation having a wavelength from about 795 nm to about 815 nm.

In an embodiment, the system 2200 includes multiple image sensors 2204 and may particularly include two image sensors for use in generating a three-dimensional image. The image sensor(s) 2204 may be color/wavelength agnostic and configured for reading any wavelength of electromagnetic radiation that is reflected off the surface 2212. In an embodiment, the image sensors 2204 are each color dependent or wavelength dependent and configured for reading electromagnetic radiation of a particular wavelength that is reflected off the surface 2212 and back to the image sensors 2204. Alternatively, the image sensor 2204 may include a single image sensor with a plurality of different pixel sensors configured for reading different wavelengths or colors of light, such as a Bayer filter color filter array. Alternatively, the image sensor 2204 may include one or more color agnostic image sensors that may be configured for reading different wavelengths of electromagnetic radiation according to a pulsing schedule such as those illustrated in FIGS. 5-7E, for example.

FIGS. 23A and 23B illustrate a perspective view and a side view, respectively, of an implementation of an imaging sensor 2300 having a plurality of pixel arrays for producing a three-dimensional image. The three-dimensional image sensor may be built on a plurality of substrates and may comprise the plurality of pixel arrays and other associated circuitry, wherein a plurality of pixel columns 2302a forming the first pixel array and a plurality of pixel columns 2302b forming a second pixel array are located on respective substrates 2308a and 2308b, respectively, and a plurality of circuit columns 2306a and 2306b are located on a separate substrate 2304. Also illustrated are the electrical connections and communications between columns of pixels to associated or corresponding column of circuitry.

The plurality of pixel arrays may sense information simultaneously and the information from the plurality of pixel arrays may be combined to generate a three-dimensional image. In an embodiment, an endoscopic imaging system includes two or more pixel arrays that can be deployed to generate three-dimensional imaging. The endoscopic imaging system may include an emitter for emitting pulses of electromagnetic radiation during a blanking period of the pixel arrays. The pixel arrays may be synced such that the optical black pixels are read (i.e., the blanking period occurs) at the same time for the two or more pixel arrays. The emitter may emit pulses of electromagnetic radiation for charging each of the two or more pixel arrays. The two or more pixel arrays may read their respective charged pixels at the same time such that the readout periods for the two or more pixel arrays occur at the same time or at approximately the same time. In an embodiment, the endoscopic imaging system includes multiple emitters that are each individual synced with one or more pixel arrays of a plurality of pixel arrays. Information from a plurality of pixel arrays may be combined to generate three-dimensional image frames and video streams.

Figure 24A:
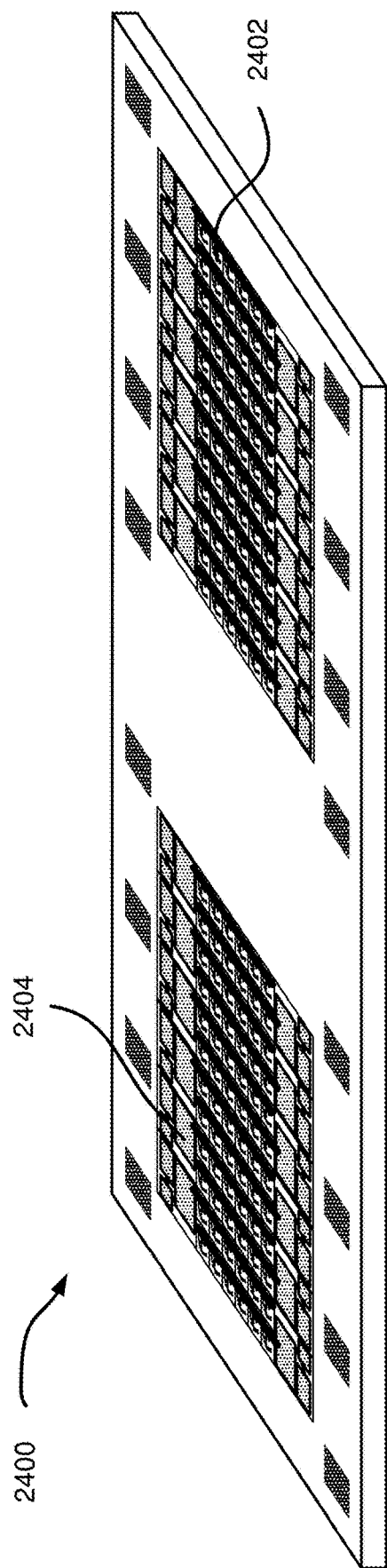
FIGS. 24A and 24B illustrate an implementation having a plurality of pixel arrays for producing a three-dimensional image in accordance with the principles and teachings of the disclosure.
Figure 24B:
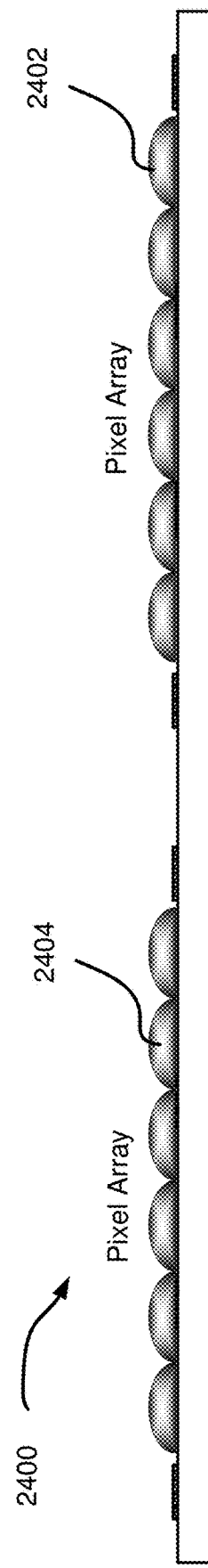

FIGS. 24A and 24B illustrate a perspective view and a side view, respectively, of an implementation of a monolithic sensor 2400 having a plurality of pixel arrays for producing a three-dimensional image in accordance with the teachings and principles of the disclosure. Such an implementation may be desirable for three-dimensional image capture, wherein the two-pixel arrays 2402 and 2404 may be offset during use. In another implementation, a first pixel array 2402 and a second pixel array 2404 may be dedicated to receiving a predetermined range of wave lengths of electromagnetic radiation, wherein the first pixel array is dedicated to a different range of wavelength electromagnetic radiation than the second pixel array.

Figure 25A:
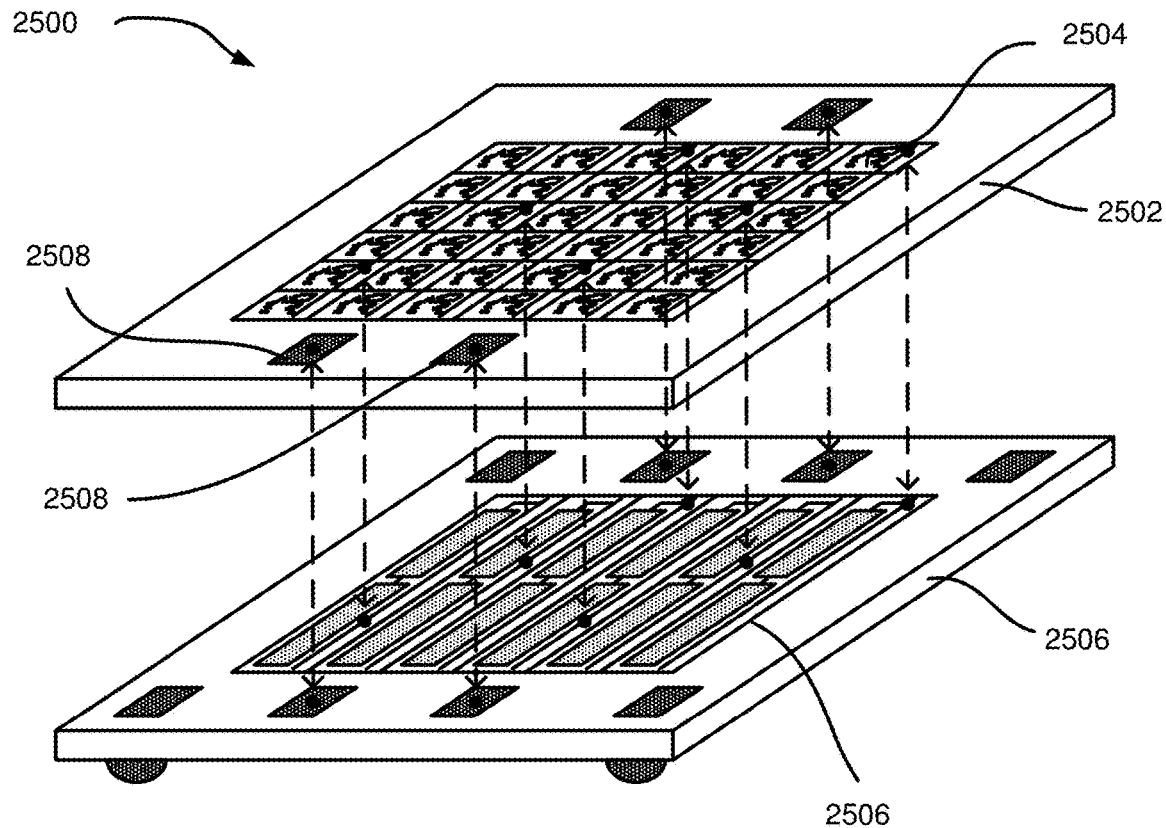
FIGS. 25A and 25B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 25B:
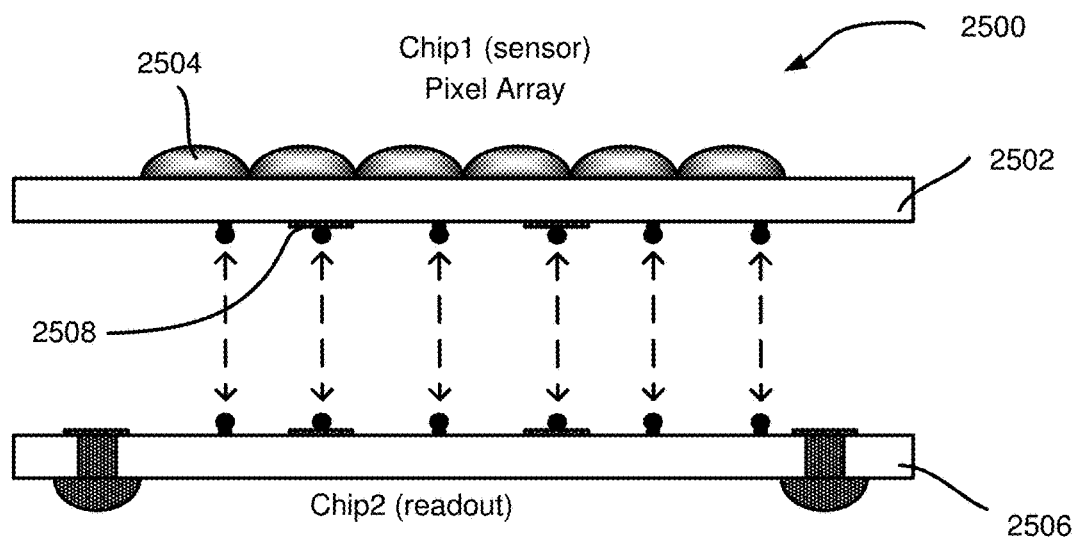

FIGS. 25A and 25B illustrate a perspective view and a side view, respectively, of an implementation of an imaging sensor 2500 built on a plurality of substrates. As illustrated, a plurality of pixel columns 2504 forming the pixel array are located on the first substrate 2502 and a plurality of circuit columns 2508 are located on a second substrate 2506. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 2502 of the two substrates/chips may be processed using an image CMOS process. The first substrate/chip 2502 may be comprised either of a pixel array exclusively or a pixel array surrounded by limited circuitry. The second or subsequent substrate/chip 2506 may be processed using any process and does not have to be from an image CMOS process. The second substrate/chip 2506 may be, but is not limited to, a highly dense digital process to integrate a variety and number of functions in a very limited space or area on the substrate/chip, or a mixed-mode or analog process to integrate for example precise analog functions, or a RF process to implement wireless capability, or MEMS (Micro-Electro-Mechanical Systems) to integrate MEMS devices. The image CMOS substrate/chip 2502 may be stacked with the second or subsequent substrate/chip 2506 using any three-dimensional technique. The second substrate/chip 2506 may support most, or a majority, of the circuitry that would have otherwise been implemented in the first image CMOS chip 2502 (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wire bonds, bump and/or TSV (Through Silicon Via).

It will be appreciated that the teachings and principles of the disclosure may be used in a reusable device platform, a limited use device platform, a re-posable use device platform, or a single use/disposable device platform without departing from the scope of the disclosure. It will be appreciated that in a re-usable device platform an end-user is responsible for cleaning and sterilization of the device. In a limited use device platform, the device can be used for some specified amount of times before becoming inoperable. Typical new device is delivered sterile with additional uses requiring the end-user to clean and sterilize before additional uses. In a re-posable use device platform, a third-party may reprocess the device (e.g., cleans, packages and sterilizes) a single-use device for additional uses at a lower cost than a new unit. In a single use/disposable device platform a device is provided sterile to the operating room and used only once before being disposed of.

EXAMPLES

The following examples pertain to preferred features of further embodiments:

Example 1 is a system. The system includes an emitter for emitting pulses of electromagnetic radiation and an image sensor comprising a pixel array for sensing reflected electromagnetic radiation. The system includes a controller in electronic communication with the emitter and the image sensor. The controller is configured to cause the emitter to emit the pulses of electromagnetic radiation at a strobing frequency, wherein the strobing frequency is determined based on a vibration frequency of vocal cords of a user. The system is such that at least a portion of the pulses of electromagnetic radiation emitted by the emitter comprises electromagnetic radiation having a wavelength from about 770 nm to about 790, and/or from about 795 nm to about 815 nm.

Example 2 is a system as in Example 1, wherein the controller is further configured to continuously determine the vibration frequency of the vocal cords of the user and adjust the strobing frequency of the emitter in accordance with the vibration frequency of the vocal cords.

Example 3 is a system as in any of Examples 1-2, wherein the controller comprises one or more processors for executing instructions stored in non-transitory computer readable storage medium, the instructions comprising: determining the vibration frequency of the vocal cords of the patient; calculating the strobing frequency based on the vibration frequency; causing the emitter to emit the pulses of electromagnetic radiation at the strobing frequency; and suppressing at least a portion of the pulses of electromagnetic radiation emitted by the emitter.

Example 4 is a system as in any of Examples 1-3, wherein the instructions are such that suppressing at least the portion of the pulses of electromagnetic radiation emitted by the emitter comprises one or more of: suppressing a pulse of electromagnetic radiation emitted during a pixel readout portion of a readout period of the image sensor; and suppressing a pulse of electromagnetic radiation emitted during a blanking portion of the readout period of the image sensor; wherein the pulses of electromagnetic radiation are suppressed such that an aggregate amount of illumination which is the sum of the amplitude and the duration of all non-suppressed pulses for a first blanking period of the image sensor is equal to the aggregate amount of illumination in a successive blanking period of the image sensor.

Example 5 is a system as in any of Examples 1-4, further comprising a microphone for sensing sound emitted by the user such that the vibration frequency of the vocal cords of the user can be calculated based on the sound.

Example 6 is a system as in any of Examples 1-5, wherein the controller is configured to suspend a readout period of the image sensor for a suspended period and cause the emitter to emit one or more pulses of electromagnetic radiation during the suspended period.

Example 7 is a system as in any of Examples 1-6, wherein two or more partial exposure frames captured by the image sensor are combined to generate a combined exposure frame, wherein the combined exposure frame comprises data for a single wavelength of electromagnetic radiation.

Example 8 is a system as in any of Examples 1-7, wherein the single wavelength of electromagnetic radiation comprises: a red wavelength of visible light; a green wavelength of visible light; a blue wavelength of visible light; or a hyperspectral wavelength of electromagnetic radiation, wherein the hyperspectral wavelength comprises one or more of the electromagnetic radiation having the wavelength from about 770 nm to about 790 nm, or from about 795 nm to about 815 nm.

Example 9 is a system as in any of Examples 1-8, wherein the combined exposure frame is processed to be substantially artifact free by normalizing the combined exposure frame using digital gain.

Example 10 is a system as in any of Examples 1-9, wherein two or more exposure frames captured by the pixel array of the image sensor are combined to generate a combined exposure frame representing pixel data responsive to a single wavelength of electromagnetic radiation pulsed by the emitter, wherein the combined exposure frame is processed to generate a normalized exposure frame by normalizing using digital gain.

Example 11 is a system as in any of Examples 1-10, wherein the image sensor is configured to generate a plurality of exposure frames, wherein each of the plurality of exposure frames corresponds to one or more pulses of electromagnetic radiation emitted by the emitter.

Example 12 is a system as in any of Examples 1-11, wherein the pixel array of the image sensor senses reflected electromagnetic radiation to generate the plurality of exposure frames during a readout period of the pixel array, wherein the readout period comprises a duration of time when active pixels in the pixel array are read.

Example 13 is a system as in any of Examples 1-12, wherein at least a portion of the pulses of electromagnetic radiation emitted by the emitter is a hyperspectral wavelength for eliciting a spectral response, wherein the hyperspectral wavelength comprises one or more of: electromagnetic radiation having the wavelength from about 513 nm to about 545 nm and electromagnetic radiation having the wavelength from about 900 nm to about 1000 nm; or electromagnetic radiation having the wavelength from about 565 nm to about 585 nm and electromagnetic radiation having the wavelength from about 900 nm to about 1000 nm.

Example 14 is a system as in any of Examples 1-13, wherein the emitter is configured to emit, during a pulse duration, a plurality of sub-pulses of electromagnetic radiation having a sub-duration shorter than the pulse duration.

Example 15 is a system as in any of Examples 1-14, wherein one or more of the pulses of electromagnetic radiation emitted by the emitter comprises electromagnetic radiation emitted at two or more wavelengths simultaneously as a single pulse or a single sub-pulse.

Example 16 is a system as in any of Examples 1-15, wherein at least a portion of the pulses of electromagnetic radiation emitted by the emitter is a hyperspectral emission that results in a hyperspectral exposure frame created by the image sensor, and wherein the controller is configured to provide the hyperspectral exposure frame to a corresponding hyperspectral system that determines a location of a critical tissue structure within a scene based on the hyperspectral exposure frame.

Example 17 is a system as in any of Examples 1-16, wherein the hyperspectral emission comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 18 is a system as in any of Examples 1-17, wherein the controller is further configured to: receive the location of the critical tissue structure from the corresponding hyperspectral system; generate an overlay frame comprising the location of the critical tissue structure; and combine the overlay frame with a color image frame depicting the scene to indicate the location of the critical tissue structure within the scene.

Example 19 is a system as in any of Examples 1-18, wherein sensing the reflected electromagnetic radiation by the pixel array comprises generating a laser mapping exposure frame by sensing reflected electromagnetic radiation resulting from the emitter pulsing the laser mapping pattern, and wherein the controller is further configured to: provide the laser mapping exposure frame to a corresponding laser mapping system that determines a topology of the scene and/or dimensions of one or more objects within the scene; provide the location of the critical tissue structure to the corresponding laser mapping system; and receive a topology and/or dimension of the critical tissue structure from the corresponding laser mapping system.

Example 20 is a system as in any of Examples 1-19, wherein the critical structure comprises one or more of a nerve, a ureter, a blood vessel, an artery, a blood flow, or a tumor.

Example 21 is a system as in any of Examples 1-20, wherein at least a portion of the pulses of electromagnetic radiation emitted by the emitter is the fluorescence excitation wavelength that results in a fluorescence exposure frame created by the image sensor, and wherein the controller is configured to provide the fluorescence exposure frame to a corresponding fluorescence system that determines a location of a critical tissue structure within a scene based on the fluorescence exposure frame.

Example 22 is a system as in any of Examples 1-21, wherein the fluorescence excitation emission comprises one or more of: electromagnetic radiation having a wavelength from about 770 nm to about 790 nm; or the electromagnetic radiation having the wavelength from about 795 nm to about 815 nm.

Example 23 is a system as in any of Examples 1-22, wherein the controller is further configured to: receive the location of the critical tissue structure from the corresponding fluorescence system; generate an overlay frame comprising the location of the critical tissue structure; and combine the overlay frame with a color image frame depicting the scene to indicate the location of the critical tissue structure within the scene.

Example 24 is a system as in any of Examples 1-23, wherein sensing the reflected electromagnetic radiation by the pixel array comprises generating a laser mapping exposure frame by sensing reflected electromagnetic radiation resulting from the emitter pulsing the laser mapping pattern, and wherein the controller is further configured to: provide the laser mapping exposure frame to a corresponding laser mapping system that determines a topology of the scene and/or dimensions of one or more objects within the scene; provide the location of the critical tissue structure to the corresponding laser mapping system; and receive a topology and/or dimension of the critical tissue structure from the corresponding laser mapping system.

Example 25 is a system as in any of Examples 1-24, wherein the critical structure comprises one or more of a nerve, a ureter, a blood vessel, an artery, a blood flow, or a tumor.

Example 26 is a system as in any of Examples 1-25, wherein the controller is configured to synchronize timing of the pulses of electromagnetic radiation during a blanking period of the image sensor, wherein the blanking period corresponds to a time between a readout of a last row of active pixels in the pixel array and a beginning of a next subsequent readout of active pixels in the pixel array.

Example 27 is a system as in any of Examples 1-26, wherein two or more pulses of electromagnetic radiation emitted by the emitter result in two or more instances of reflected electromagnetic radiation that are sensed by the pixel array to generate two or more exposure frames that are combined to form an image frame.

Example 28 is a system as in any of Examples 1-27, wherein the image sensor comprises a first image sensor and a second image sensor such that the image sensor can generate a three-dimensional image.

Example 29 is a system as in any of Examples 1-28, wherein the emitter is configured to emit a sequence of pulses of electromagnetic radiation repeatedly sufficient for generating a video stream comprising a plurality of image frames, wherein each image frame in the video stream comprises data from a plurality of exposure frames, and wherein each of the exposure frames corresponds to a pulse of electromagnetic radiation.

Example 30 is a system as in any of Examples 1-29, wherein the pulses of electromagnetic radiation are emitted in a pattern of varying wavelengths of electromagnetic radiation, and wherein the emitter repeats the pattern of varying wavelengths of electromagnetic radiation.

Example 31 is a system as in any of Examples 1-30, wherein at least a portion of the pulses of electromagnetic radiation comprise a red wavelength, a green wavelength, a blue wavelength, and a hyperspectral wavelength such that reflected electromagnetic radiation sensed by the pixel array corresponding to each of the red wavelength, the green wavelength, the blue wavelength, and the hyperspectral wavelength can be processed to generate a Red-Green-Blue (RGB) image frame comprising an overlay of hyperspectral imaging data, wherein the hyperspectral wavelength of electromagnetic radiation comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 32 is a system as in any of Examples 1-31, wherein at least a portion of the pulses of electromagnetic radiation comprise a luminance emission, a red chrominance emission, a blue chrominance emission, and a hyperspectral emission such that reflected electromagnetic radiation sensed by the pixel array corresponding to each of the luminance emission, the red chrominance emission, the blue chrominance emission, and the hyperspectral emission can be processed to generate a YCbCr image frame comprising an overlay of hyperspectral imaging data, wherein the hyperspectral emission of electromagnetic radiation comprises: the electromagnetic radiation having the wavelength from about 513 nm to about 545 nm and the electromagnetic radiation having the wavelength from about 900 nm to about 1000 nm; or the electromagnetic radiation having the wavelength from about 565 nm to about 585 nm and the electromagnetic radiation having the wavelength from about 900 nm to about 1000 nm.

Example 33 is a system as in any of Examples 1-32, wherein at least a portion of the pulses of electromagnetic radiation emitted by the emitter is a fluorescence excitation wavelength for fluorescing a reagent, wherein the fluorescence excitation wavelength comprises one or more of: the electromagnetic radiation having the wavelength from about 770 nm to about 790 nm; or the electromagnetic radiation having the wavelength from about 795 nm to about 815 nm.

Example 34 is a system as in any of Examples 1-33, wherein at least a portion of the pulses of electromagnetic radiation comprise a red wavelength, a green wavelength, a blue wavelength, and a fluorescence excitation wavelength such that reflected electromagnetic radiation sensed by the pixel array corresponding to each of the red wavelength, the green wavelength, the blue wavelength, and the fluorescence excitation wavelength can be processed to generate a Red-Green-Blue (RGB) image frame comprising an overlay of fluorescence imaging data, wherein the fluorescence wavelength of electromagnetic radiation comprises: electromagnetic radiation having the wavelength from about 770 nm to about 790 nm and/or electromagnetic radiation having the wavelength from about 795 nm to about 815 nm.

Example 35 is a system as in any of Examples 1-34, wherein at least a portion of the pulses of electromagnetic radiation comprise a luminance emission, a red chrominance emission, a blue chrominance emission, and a fluorescence excitation emission such that reflected electromagnetic radiation sensed by the pixel array corresponding to each of the luminance emission, the red chrominance emission, the blue chrominance emission, and the fluorescence excitation emission can be processed to generate a YCbCr image frame comprising an overlay of fluorescence imaging data, wherein the fluorescence wavelength of electromagnetic radiation comprises: electromagnetic radiation having the wavelength from about 770 nm to about 790 nm and/or electromagnetic radiation having the wavelength from about 795 nm to about 815 nm.

Example 36 is a system as in any of Examples 1-35, further comprising a controller in communication with the controller.

Example 37 is a system as in any of Examples 1-36, wherein the pixel array is a two-dimensional array of independent pixels each capable of detecting any wavelength of electromagnetic radiation.

Example 38 is a system as in any of Examples 1-37, further comprising a filter that filters electromagnetic radiation having a wavelength from about 770 nm to about 790 nm.

Example 39 is a system as in any of Examples 1-38, further comprising a filter that filters electromagnetic radiation having a wavelength from about 795 nm to about 815 nm.

Example 40 is a system as in any of Examples 1-39, wherein the image sensor is CMOS image sensor.

Example 41 is a system as in any of Examples 1-40, wherein sensing reflected electromagnetic radiation by the pixel array comprises generating a laser mapping exposure frame by sensing reflected electromagnetic radiation resulting from the emitter pulsing the laser mapping pattern, wherein the laser mapping exposure frame comprises information for determining real time measurements comprising one or more of: a distance from an endoscope to an object; an angle between an endoscope and the object; or surface topology information about the object.

Example 42 is a system as in any of Examples 1-41, wherein the laser mapping exposure frame comprises information for determining the real time measurements to an accuracy of less than 10 centimeters.

Example 43 is a system as in any of Examples 1-42, wherein the laser mapping exposure frame comprises information for determining the real time measurements to an accuracy of less than one millimeter.

Example 44 is a system as in any of Examples 1-43, wherein at least a portion of the pulses of electromagnetic radiation emitted by the emitter comprises a plurality of tool-specific laser mapping patterns for each of a plurality of tools within a scene.

Example 45 is a system as in any of Examples 1-44, wherein the laser mapping pattern emitted by the emitter comprises a first output and a second output that are independent from one another, wherein the first output is for light illumination and the second output is for tool tracking.

Example 46 is a method. The method includes determining a vibration frequency of vocal cords of a patient. The method includes pulsing a plurality of pulses of electromagnetic radiation by an emitter at a strobing frequency that substantially matches the vibration frequency of the vocal cords. The method includes receiving a plurality of exposure frames captured by a pixel array of an image sensor, wherein the pixel array is configured to sense reflected electromagnetic radiation. The method is such that at least a portion of the pulses of electromagnetic radiation emitted by the emitter comprises electromagnetic radiation having a wavelength from about 770 nm to about 790 and/or from about 795 nm to about 815 nm.

Example 46 is a method as in Example 45, further comprising: combining two or more exposure frames of the plurality of exposure frames to generate a combined exposure frame; and processing the combined exposure frame to generate a normalized exposure frame by normalizing the combined exposure frame using digital gain; wherein the two or more exposure frames are sensed by the pixel array in response to a single wavelength of electromagnetic radiation pulsed by the emitter.

Example 47 is a method as in any of Examples 45-46, further comprising: suppressing a pulse of electromagnetic radiation emitted during a pixel readout portion of a readout period of the image sensor; and suppressing a pulse of electromagnetic radiation emitted during a blanking portion of the readout period of the image sensor; wherein the pulses of electromagnetic radiation are suppressed such that an aggregate amount of illumination which is the sum of the amplitude and the duration of all non-suppressed pulses for a first blanking period of the image sensor is equal to the aggregate amount of illumination in a successive blanking period of the image sensor.

Example 48 is a method as in any of Examples 45-47, wherein one or more pulses of electromagnetic radiation emitted by the emitter is a hyperspectral emission that results in a hyperspectral exposure frame created by the image sensor and the method further comprises: providing the hyperspectral exposure frame to a corresponding system that determines a location of a critical tissue structure within a scene based on the hyperspectral exposure frame; receiving the location of the critical tissue structure from the corresponding system; generating an overlay frame comprising the location of the critical tissue structure; and combining the overlay frame with a color image frame depicting the scene to indicate the location of the critical tissue structure within the scene.

Example 49 is a method as in any of Examples 45-48, further comprising suspending a readout period of the image sensor for a suspended period and causing the emitter to emit one or more pulses of electromagnetic radiation during the suspended period.

Example 50 is a method as in any of Examples 45-49, further comprising compiling a video stream comprising image frames, wherein each of the image frames comprises data from two or more of the plurality of exposure frames.

Example 51 is a method as in any of Examples 45-50, further comprising reducing the presence of artifacts in the video stream by disabling the pulsing by the emitter during a readout period of the image sensor.

Example 52 is a method as in any of Examples 45-51, further comprising suppressing pulses of electromagnetic radiation that straddle a readout period and a blanking period of the image sensor.

Example 53 is a method as in any of Examples 45-52, further comprising suspending a sensor readout period a plurality of times per exposure frame and pulsing electromagnetic radiation during each suspension period.

Example 54 is a method as in any of Examples 45-53, further comprising superimposing all exposure frames captured during a readout sequence captured in response to a single wavelength of electromagnetic radiation pulsed by the emitter.

Example 55 is a method as in any of Examples 45-54, further comprising applying a digital gain factor to a subset of rows in a combined exposure frame, wherein the combined exposure frame comprises data from a plurality of partial exposure frames each captured in response to a portion of the pixels in the pixel array being read in response to a single type of wavelength of electromagnetic radiation pulsed by the emitter.

Example 56 is a method as in any of Examples 45-55, further comprising applying a digital gain factor to all rows in a combined exposure frame, wherein the combined exposure frames comprises data corresponding to a single wavelength of electromagnetic radiation emitted by the emitter over the course of multiple pulses of the single wavelength of electromagnetic radiation and multiple readout periods of the image sensor.

Example 57 is a method as in any of Examples 45-56, further comprising generating a plurality of partial exposure frames, wherein each of the plurality of partial exposure frames comprises data read out by a portion of the pixels of the pixel array in response to an emission of a certain wavelength of electromagnetic radiation by the emitter.

Example 58 is a method as in any of Examples 45-57, further comprising superimposing the plurality of partial exposure frames that each correspond to the certain wavelength of electromagnetic radiation.

Example 59 is a method as in any of Examples 45-58, wherein each of the plurality of partial exposure frames is captured during a readout period of the image sensor, and wherein the plurality of partial exposure frames are captured in response to a plurality of pulses of the certain wavelength of electromagnetic radiation.

Example 60 is a method as in any of Examples 45-59, further comprising generating an exposure frame comprising data from a plurality of partial exposure frames captured in response to a certain wavelength of electromagnetic radiation.

Example 61 is a method as in any of Examples 45-60, further comprising superimposing a plurality of exposure frames to generate an image frame, wherein each of the plurality of exposure frames comprises data captured in response to a different wavelength of electromagnetic radiation.

Example 62 is a method as in any of Examples 45-61, wherein the image frame comprises a red exposure frame, a green exposure frame, a blue exposure frame, and one or more of a hyperspectral exposure frame, a fluorescence exposure frame, or a laser mapping exposure frame.

Example 63 is a method as in any of Examples 45-62, further comprising tracking a light deficiency for each row of pixels in the pixel array in a superimposed combined exposure frame.

Example 64 is a method as in any of Examples 45-63, further comprising applying a digital gain to normalize an image frame to be artifact-free.

Example 65 is a method as in any of Examples 45-64, further comprising calculating the frequency of the vocal cords of the patient based on sound data of the patient's voice captured by a microphone.

Example 66 is a method as in any of Examples 45-65, further comprising reading out information captured by the pixel array of the image sensor, wherein at least one of the plurality of pulses of electromagnetic radiation occurs during a readout period of the image sensor.

Example 67 is a method as in any of Examples 45-66, further comprising creating a sensor readout frame for each readout sequence of the image sensor.

Example 68 is a method as in any of Examples 45-67, further comprising superimposing two or more partial exposure frames to generate an exposure frame, wherein each of the two or more partial exposure frames is read out by the pixel array in response to a certain wavelength of electromagnetic radiation being pulsed by the emitter, wherein the certain wavelength of electromagnetic radiation comprises one or more of a red wavelength, a green wavelength, or a blue wavelength of electromagnetic radiation.

Example 69 is a method as in any of Examples 45-68, wherein pulsing the plurality of pulses of electromagnetic radiation comprises pulsing a hyperspectral emission that results in a hyperspectral exposure frame created by the image sensor, and wherein the method further comprises: providing the hyperspectral exposure frame to a corresponding system that determines a location of a critical tissue structure within a scene based on the hyperspectral exposure frame; receiving the location of the critical tissue structure from the corresponding system; generating an overlay frame comprising the location of the critical tissue structure; and combining the overlay frame with a color image frame depicting the scene to indicate the location of the critical tissue structure within the scene.

Example 70 is a method as in any of Examples 45-69, wherein pulsing the plurality of pulses of electromagnetic radiation comprises pulsing a fluorescence excitation emission that results in a fluorescence exposure frame created by the image sensor, and wherein the method further comprises: providing the fluorescence exposure frame to a corresponding system that determines a location of a critical tissue structure within a scene based on the fluorescence exposure frame; receiving the location of the critical tissue structure from the corresponding system; generating an overlay frame comprising the location of the critical tissue structure; and combining the overlay frame with a color image frame depicting the scene to indicate the location of the critical tissue structure within the scene.

It will be appreciated that various features disclosed herein provide significant advantages and advancements in the art. The following claims are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that any features of the above-described arrangements, examples, and embodiments may be combined in a single embodiment comprising a combination of features taken from any of the disclosed arrangements, examples, and embodiments.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) or field programmable gate arrays (FPGAs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system for endoscopic visualization of a scene, the system comprising:
an emitter that emits a plurality of pulses of electromagnetic radiation according to a pulse cycle, wherein the plurality of pulses comprises:

a plurality of strobing pulses; and
a fluorescence excitation pulse comprising electromagnetic radiation within a waveband from about 775 nm to about 815 nm;
an image sensor comprising a pixel array that accumulates electromagnetic radiation and reads out a plurality of exposure frames according to a sensor cycle that comprises a plurality of readout periods and a plurality of blanking periods; and
a controller in electronic communication with the emitter and the image sensor that synchronizes timing of the pulse cycle and the sensor cycle, wherein the controller comprises one or more processors configured to execute instructions comprising:
determining a vibration frequency of a vocal cord of a user;
calculating a strobing frequency based on the vibration frequency;
instructing the emitter to emit the plurality of strobing pulses at the strobing frequency;
identifying, based on synchronization of the pulse cycle and the sensor cycle, at least one strobing pulse that will be emitted during an identified readout period of the image sensor; and
causing the image sensor to suspend pixel readout when the at least one strobing pulse is emitted during the identified readout period.

2. The system of claim 1, wherein the instructions executed by the controller further comprise continuously determining the vibration frequency of the vocal cords of the user and adjusting the strobing frequency of the emitter in accordance with the vibration frequency of the vocal cords.

3. The system of claim 1, further comprising a microphone for sensing sound emitted by the user such that determining the vibration frequency of the vocal cord of the user comprises determining based on the sound.

4. The system of claim 1, wherein the instructions executed by the controller further comprise instructing the emitter to emit the at least one strobing pulse during the identified readout period when the pixel readout of the image sensor is suspended.

5. The system of claim 1, wherein the emitter comprises a plurality of sources of electromagnetic radiation that are independently actuatable, and wherein the plurality of sources comprises:
a visible source, wherein the visible source comprises one or more of a red source, a green source, a blue source, or a white source of electromagnetic radiation; and
an excitation source configured to emit the fluorescence excitation pulse, wherein the excitation source pulses only the electromagnetic radiation within the waveband from about 775 nm to about 815 nm.

6. The system of claim 1, wherein the instructions executed by the controller further comprise:
receiving a fluorescence exposure frame output by the image sensor, wherein the pixel array accumulates the electromagnetic radiation corresponding with the fluorescence exposure frame when the emitter pulses only the fluorescence excitation wavelength; and
processing the fluorescence exposure frame to remove artifacts by normalizing the fluorescence exposure frame using digital gain.

7. The system of claim 1, wherein the instructions executed by the controller further comprise:
receiving a first partial exposure frame, wherein the image sensor suspended readout of the pixel array at least once during a readout period corresponding with the first partial exposure frame;
a receiving a second partial exposure frame, wherein the image sensor suspended readout of the pixel array at least once during a readout period corresponding with the second partial exposure frame; and
generating a combined exposure frame based on data extracted from each of the first partial exposure frame and the second partial exposure frame.

8. The system of claim 7, wherein the instructions executed by the image sensor further comprise normalizing the combined exposure frame to compensate for one or more of:
dark regions within the combined exposure frame comprising a light deficiency compared with a computed reference level; or
bright regions within the combined exposure frame comprising excess light with respect to the computed reference level.

9. The system of claim 8, wherein the dark regions within the combined exposure frame comprise the light deficiency due to the image sensor suspending the readout of the pixel array during the readout period for one of the first partial exposure frame or the second partial exposure frame when reading out pixels corresponding with the dark regions; and
wherein the bright regions within the combined exposure frame comprise the excess light due to the image sensor reading out pixels corresponding with the bright regions during the readout period for each of the first partial exposure frame and the second partial exposure.

10. The system of claim 1, wherein the fluorescence excitation wavelength comprises one or more of:
electromagnetic radiation only within a waveband about 770 nm to about 795 nm; or
electromagnetic radiation only within a waveband about 790 nm to about 815 nm.

11. The system of claim 1, wherein the plurality of strobing pulses comprises electromagnetic radiation within a visible waveband of the electromagnetic spectrum.

12. The system of claim 1, wherein the image sensor outputs a fluorescence exposure frame in response to the emitter pulsing the fluorescence excitation pulse; and
wherein the instructions executed by the controller further comprise providing the fluorescence exposure frame to a corresponding system that determines one or more of a location or an identity of a tissue structure within the scene based on pixel values from the fluorescence exposure frame.

13. The system of claim 1, wherein the emitter comprises two or more independently actuatable fluorescence excitation sources tuned to emit the fluorescence excitation pulse, and wherein the two more fluorescence excitation sources comprise:
a first excitation source tuned to pulse only electromagnetic radiation within a waveband from about 775 nm to about 795 nm; and
a second excitation source tuned to pulse only electromagnetic radiation within a waveband from about 790 nm to about 815 nm.

14. The system of claim 13, wherein the instructions executed by the controller further comprise:
receiving a fluorescence exposure frame sensed by the image sensor in response to the emitter cycling on one or more of the first excitation source or the second excitation source;

providing the fluorescence exposure frame to a corresponding system trained to identify a tissue structure within the scene based on pixel values from the fluorescence exposure frame;
receiving the identification of the tissue structure from the corresponding system; and
generating an overlay frame comprising a highlight of the tissue structure overlaid on color imaging data.

15. The system of claim 14, wherein the tissue structure comprises one or more of a nerve, a ureter, a blood vessel, an artery, a blood flow, or a tumor.

16. The system of claim 1, wherein the pulse cycle comprises a pattern of varying wavelengths of electromagnetic radiation, and wherein the emitter repeats the pattern of varying wavelengths of electromagnetic radiation.

17. The system of claim 1, wherein the plurality of pulses of electromagnetic radiation comprises:
a plurality of visible emissions comprising electromagnetic radiation within a visible waveband of the electromagnetic spectrum; and
a plurality of the fluorescence excitation pulse;
wherein the reflected electromagnetic radiation accumulated by the pixel array corresponding to each of the plurality of visible emission and the plurality of the fluorescence excitation pulse is processed to generate a Red-Green-Blue (RGB) image frame comprising an overlay of fluorescence imaging data.

18. The system of claim 1, wherein at least a portion of the pulses of electromagnetic radiation comprises:
a luminance emission comprising electromagnetic radiation within a wavelength band selected for identifying luminance data;
a red chrominance emission comprising electromagnetic radiation within a wavelength band selected for identifying red chrominance data;
a blue chrominance emission comprising electromagnetic radiation within a wavelength band selected for identifying blue chrominance data; and
the fluorescence excitation pulse;
wherein the electromagnetic radiation accumulated by the pixel array corresponding to each of the luminance emission, the red chrominance emission, the blue chrominance emission, and the excitation emission pulse is processed to generate a YCbCr image frame comprising an overlay of fluorescence imaging data.

19. The system of claim 1, wherein the instructions executed by the controller are such that causing the image sensor to suspend the pixel readout when the at least one strobing pulse is emitted during the identified readout period comprises freezing a clock of the image sensor.

20. The system of claim 1, wherein the instructions executed by the controller are such that causing the image sensor to suspend the pixel readout when the at least one strobing pulse is emitted during the identified readout period comprises freezing a vertical decoder of the image sensor.

21. The system of claim 1, further comprising a flexible endoscope configured to be inserted into one or more of an oral cavity or a nasal cavity or a patient, and wherein the image sensor is disposed at a distal end of the flexible endoscope.

22. The system of claim 1, wherein the pulse cycle comprises:
a plurality of visible pulses comprising electromagnetic radiation within a visible waveband of the electromagnetic spectrum; and
a plurality of the fluorescence excitation pulse;
wherein the pulse cycle alternates at least a portion of the plurality of visible pulses and the plurality of the fluorescence excitation pulse such that the emitter pulses only one of the visible waveband or the electromagnetic radiation within the waveband from about 775 nm to about 815 nm at one time.

23. The system of claim 1, wherein the pulse cycle comprises:
the plurality of strobing pulses; and
a plurality of the fluorescence excitation pulse;
wherein at least one of the plurality of the fluorescence excitation pulse overlaps with at least one strobing pulse of the plurality of strobing pulses.

24. The system of claim 1, wherein the fluorescence excitation pulse is emitted for an excitation pulse duration;
wherein at least a portion of the plurality of strobing pulses is emitted for a strobing pulse duration; and
wherein the excitation pulse duration is longer than the strobing pulse duration.

25. The system of claim 1, wherein the plurality of strobing pulses comprises white light.

* * * * *